(12) United States Patent
Ririe et al.

(10) Patent No.: US 10,875,026 B2
(45) Date of Patent: Dec. 29, 2020

(54) DEVICES AND METHODS FOR RAPID PCR

(71) Applicant: BIOFIRE DEFENSE, LLC, Salt Lake City, UT (US)

(72) Inventors: Kirk Max Ririe, Salt Lake City, UT (US); David E. Jones, Layton, UT (US); Christopher Paul Pasko, Salt Lake City, UT (US); Anson Cole Chamberlain, American Fork, UT (US); Derek David, Salt Lake City, UT (US); Aaron Wernerehl, Salt Lake City, UT (US); Jonathan Allen Bruns, Salt Lake City, UT (US)

(73) Assignee: BioFire Defense, LLC, Salt Lake City, UT (US)

( * ) Notice: Subject to any disclaimer, the term of this patent is extended or adjusted under 35 U.S.C. 154(b) by 0 days.

(21) Appl. No.: 16/078,637

(22) PCT Filed: Feb. 21, 2017

(86) PCT No.: PCT/US2017/018748
§ 371 (c)(1),
(2) Date: Aug. 21, 2018

(87) PCT Pub. No.: WO2017/147085
PCT Pub. Date: Aug. 31, 2017

(65) Prior Publication Data
US 2019/0046989 A1 Feb. 14, 2019

Related U.S. Application Data

(60) Provisional application No. 62/298,311, filed on Feb. 22, 2016, provisional application No. 62/330,701, filed on May 2, 2016, provisional application No. 62/409,829, filed on Oct. 18, 2016.

(51) Int. Cl.
*B01L 7/00* (2006.01)
*C12Q 1/686* (2018.01)
*B01L 3/00* (2006.01)

(52) U.S. Cl.
CPC ........... *B01L 7/525* (2013.01); *B01L 3/50273* (2013.01); *C12Q 1/686* (2013.01); *B01L 2200/0647* (2013.01); *B01L 2300/0816* (2013.01); *B01L 2300/0864* (2013.01); *B01L 2300/0867* (2013.01); *B01L 2300/18* (2013.01); *B01L 2300/1816* (2013.01); *B01L 2300/1822* (2013.01); *B01L 2300/1827* (2013.01); *B01L 2300/1861* (2013.01); *B01L 2400/0481* (2013.01)

(58) Field of Classification Search
CPC ...... B01L 3/50273; B01L 7/525; C12Q 1/686
See application file for complete search history.

(56) References Cited

U.S. PATENT DOCUMENTS

| 5,827,480 | A | 10/1998 | Haff et al. | |
|---|---|---|---|---|
| 2006/0088931 | A1* | 4/2006 | Ririe | B01L 3/502 435/304.1 |
| 2006/0110763 | A1 | 5/2006 | Kopp | |
| 2007/0254372 | A1 | 11/2007 | Bickel et al. | |
| 2007/0298429 | A1* | 12/2007 | Gumbrecht | B01L 3/5027 435/6.19 |
| 2008/0280331 | A1 | 11/2008 | Davies et al. | |
| 2009/0142745 | A1 | 6/2009 | Breidenthal et al. | |
| 2010/0056383 | A1* | 3/2010 | Ririe | B01L 3/50273 506/7 |
| 2010/0291634 | A1* | 11/2010 | Chun | C12Q 21/6853 435/91.2 |
| 2011/0076674 | A1 | 3/2011 | Blaschke-Bonkowsky | |
| 2013/0157349 | A1 | 6/2013 | Ririe et al. | |
| 2015/0231591 | A1 | 8/2015 | Murayama | |

FOREIGN PATENT DOCUMENTS

| CN | 102994369 | | 3/2013 |
|---|---|---|---|
| WO | WO 2006047777 | * | 5/2006 |
| WO | 2007100500 | | 9/2007 |
| WO | 2015069743 | | 5/2015 |

OTHER PUBLICATIONS

International Search Report and Written Opinion, United States International Search Authority, PCT/US2017/018748, dated Jun. 7, 2017.

* cited by examiner

*Primary Examiner* — Narayan K Bhat
(74) *Attorney, Agent, or Firm* — Workman Nydegger

(57) ABSTRACT

Instruments, methods, and kits are disclosed for performing fast thermocycling.

12 Claims, 41 Drawing Sheets

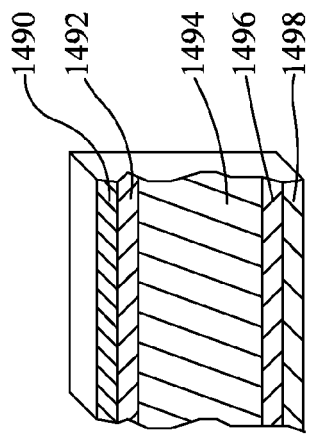
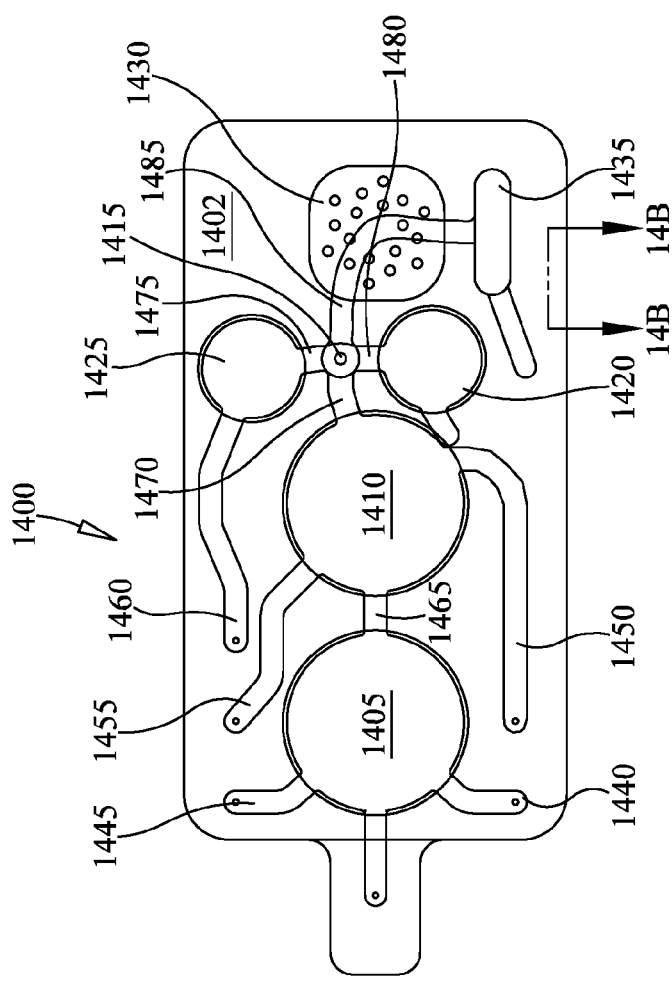
FIG. 14B
FIG. 14A

DEVICES AND METHODS FOR RAPID PCR

CROSS REFERENCE TO RELATED APPLICATIONS

This application claims priority to PCT Application No. PCT/US2017/018748, filed Feb. 21, 2017, entitled "DEVICES AND METHODS FOR RAPID PCR", which claims the benefit of and priority to U.S. Provisional Application Nos. 62/298,311, filed Feb. 22, 2016, U.S. Prov. App. Ser. No. 62/330,701, filed May 2, 2016, and U.S. Prov. App. Ser. No. 62/409,829, filed Oct. 18, 2016. All the aforementioned applications are incorporated by reference herein in their entirety.

GOVERNMENT INTEREST

This invention was made with government support under W911QY-13-D-0080 awarded by the U.S. Department of Defense. The government has certain rights in the invention.

BACKGROUND

1. Technical Field

Embodiments of the present disclosure relate generally to methods and devices for amplifying nucleic acids.

2. Background

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms or viruses and the low levels of organism or virus present in some pathological specimens. It is often impractical to run large panels of PCR assays, one for each possible causative organism or viruses, most of which are expected to be negative. The problem may be exacerbated when pathogen nucleic acid is at low concentration and requires a large volume of sample to gather adequate reaction templates. In some cases there is inadequate sample to assay for all possible etiological agents. A solution is to run "multiplex PCR" wherein the sample is concurrently assayed for multiple targets in a single reaction. While multiplex PCR has proven to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. Closed systems such as the FilmArray® (BioFire Diagnostics, LLC, Salt Lake City, Utah) reduce handling, thereby diminishing contamination risk.

PCR may be conceptually divided into 3 reactions, each usually assumed to occur over time at each of three temperatures. Such an "equilibrium paradigm" of PCR is easy to understand in terms of three reactions (denaturation, annealing, and extension) occurring at 3 temperatures over 3 time periods each cycle. However, this equilibrium paradigm does not fit well with physical reality. Instantaneous temperature changes do not occur; it takes time to change the sample temperature. Furthermore, individual reaction rates vary with temperature, and once primer annealing occurs, polymerase extension immediately follows. More accurate, particularly for rapid PCR, is a kinetic paradigm where reaction rates and temperature are always changing. Holding the temperature constant during PCR is not necessary as long as the products denature and the primers anneal. Under the kinetic paradigm of PCR, product denaturation, primer annealing, and polymerase extension may temporally overlap and their rates continuously vary with temperature. Under the equilibrium paradigm, a cycle is defined by 3 temperatures each held for a time period, whereas the kinetic paradigm requires transition rates and target temperatures. Illustrative time/temperature profiles for the equilibrium and kinetic paradigms are shown in FIGS. 5a-5b. However, it is understood that these temperature profiles are illustrative only and that in some implementations of PCR, the annealing and extension steps are combined so that only 2 temperatures are needed.

When PCR was first popularized in the late 1980s, the process was slow. A typical protocol was one minute for denaturation at 94° C., two minutes for annealing at 55° C., and three minutes for extension at 72° C. When the time for transition between temperatures was included, 8 minute cycles were typical, resulting in completion of 30 cycles in four hours. Twenty-five percent of the cycling time was spent in temperature transitions. As cycling speeds increased, the proportion of time spent in temperature transitions also increased and the kinetic paradigm became more and more relevant. During rapid cycle PCR, the temperature is usually changing. For rapid cycle PCR of short products (<100 bps), 100% of the time may be spent in temperature transition and no holding times are necessary. For rapid cycle PCR of longer products, a temperature hold at an optimal extension temperature may be included.

In isolation, the term "rapid PCR" is both relative and vague. A one-hour PCR is rapid compared to four hours, but slow compared to 15 minutes. Furthermore, PCR protocols can be made shorter if one starts with higher template concentrations or uses fewer cycles. A more specific measure is the time required for each cycle. Thus, "rapid cycle PCR" (or "rapid cycling") was defined in 1994 as 30 cycles completed in 10-30 minutes, resulting in cycles of 20-60 seconds each. This actual time of each cycle is longer than the sum of the times often programmed for denaturation, annealing and extension, as time is needed to ramp the temperatures between each of these stages. Initial work in the early 1990s established the feasibility of rapid cycling using capillary tubes and hot air for temperature control. Over the years, systems have become faster, and the kinetic requirements of denaturation, annealing, and extension have become clearer.

Rapid protocols use momentary or "0" second holds at the denaturation and annealing temperatures. That is, the temperature-time profiles show temperature spikes for denaturation and annealing, without holding the top and bottom temperatures. Denaturation and annealing can occur very quickly.

Conclusions from this early work were: 1) denaturation of PCR products is very rapid with no need to hold the denaturation temperature, 2) annealing of primers can occur very quickly, particularly with higher primer concentrations, and annealing temperature holds may not be necessary, and 3) the required extension time depends on PCR product length and polymerase concentration. Also, rapid cycle PCR is not only faster, but better in terms of specificity and yield as long as the temperature was controlled precisely.

One way to decrease cycle time is to introduce variations to the PCR protocol to ease the temperature cycling requirements. Longer primers with higher Tms allow higher annealing temperatures. By limiting the product length and its Tm, denaturation temperatures can be lowered to just above the product Tm. In combination, higher annealing and lower denaturation temperatures decrease the temperature range required for successful amplification. Reducing 3-step cycling (denaturation, annealing, and extension) to 2-steps (denaturation and a combined annealing/extension step) also simplifies the temperature cycling requirements. Two-step cycling can, however, compromise polymerase extension rates if the combined annealing/extension step is performed at temperatures lower than the 70 to 80° C. temperature optimum where the polymerase is most active, particularly with fast ramp rates. Polymerase extension rates are log-linear with temperature until about 70-80° C., with a reported maximum of 60-120 bp/s.

Even with protocol variations, amplification efficiency and yield are often poor when cycle times are <20 seconds when compared to control reactions. These efforts towards faster PCR appear dominated by engineering with little focus on the biochemistry. As cycle times decrease from 20 seconds towards 2 seconds, PCR yield decreases and finally disappears, reflecting a lack of robustness even with simple targets at high copy number.

Recently, a system has been reported using thin walled capillaries and water baths to thermocycle or using induction heating (US 2015/0118715; WO 2015/069743, herein incorporated in their entireties by reference) at speeds of less than 10 seconds per cycle, and in some embodiments less than one second per cycle. Adjustments in chemistry for this "extreme PCR", wherein polymerase and primer concentration are increased, permit the polymerase chain reaction to proceed at such fast rates.

In one example of extreme PCR, the polymerase is provided at a concentration of at least 0.5 µM and primers are each provided at a concentration of at least 2 µM, and in some examples the primer concentration is 2.5 µM or more. By non-limiting example, annealing time may be defined by annealing time=k1/[primer], wherein k1 is a constant and [primer] is the concentration of each primer, and time at the elongation temperature may be defined by elongation time=k2(extension length)/([polymerase]*(polymerase speed)), wherein k2 is a proportionality constant, [polymerase] is the concentration of the polymerase, and polymerase speed is a rate of polymerase incorporation of bases in nucleotides. In another example of extreme PCR, the polymerase to primer ratio is illustratively (about 0.03 to about 0.4 polymerase):(total primer concentration), and the polymerase concentration is at least 0.5 µM. It is noted that polymerase Unit definitions can be confusing. For native Taq polymerase, 0.4 U/10 µl is about 1.5 nM under typical rapid cycling conditions.

While improvements in chemistry are reported in WO 2013/177429, the device requires large water baths, and it is ideally placed inside a water-resistant cabinet. Rapid temperature cycling having cycle times of 10 seconds or less using the chemistry of WO 2013/177429 in commercial instrumentation would be desired. It would also be desirable to perform such rapid temperature cycling in a closed container.

The present invention addresses various issues relating to fast PCR, including contamination risks by providing devices, kits, and methods for fast PCR, illustratively in a closed container.

BRIEF SUMMARY

Described herein are devices (instruments and systems) and methods for rapid amplification of nucleic acids in a flexible sample container. In an illustrative embodiment, a flexible sample container may include a first-stage chamber fluidly connected to a second-stage reaction zone, the second-stage reaction zone comprising a plurality of second-stage reaction wells. Conventionally, thermocycling devices for nucleic acid amplification include a heater that raises and lowers the temperature of a sample to accomplish a number of cycling of annealing, elongation, and denaturation. In contrast, the devices described herein may include a temperature control element that includes a first temperature zone and a second temperature zone. In one example, the temperatures of the first temperature zone and the second temperature zone may be held constant, wherein, illustratively, one zone may be held at an elongation temperature and the other zone may be held at a denaturation temperature. Alternatively, the first temperature zone and the second temperature zone may be thermally cycled in a limited range (e.g., a 5-20° C. range). The temperature control unit and various portions of a flexible sample container may be aligned to accomplish temperature cycling for nucleic acid amplification. Other components of the device described in detail herein may work cooperatively with the temperature control unit to accomplish thermal cycling. Because the temperatures of the first temperature zone and the second temperature zone are held constant or are cycled in a narrow range, the temperature changes for nucleic acid amplification can be accomplished more quickly.

In one embodiment, a method of thermal cycling is described. The method includes (a) providing a sample container comprising a first-stage chamber fluidly connected to a second-stage reaction zone, the second-stage reaction zone comprising a plurality of second-stage reaction wells, (b) introducing a sample into the sample container, and (c) inserting the sample container into an instrument, the instrument comprising a temperature control element. The method further includes (d) aligning the temperature control element and the first-stage chamber to effect thermal cycling of the sample in the first-stage chamber, (e) after effecting thermal cycling of the sample in the first-stage chamber, moving at least a fraction of a product derived from the sample from the first-stage chamber into the plurality of second-stage reaction wells in the second-stage reaction zone, and (f) aligning the temperature control element and the second-stage reaction zone to effect thermal cycling of the fraction of the sample in the second-stage reaction zone.

In one aspect, the temperature control element may include one or more heater or cooler devices such as, but not limited to, Peltier devices, resistance heaters, induction heaters, electromagnetic heaters, thin film heaters, printed element heaters, positive temperature coefficient heaters, and combinations thereof. In one aspect, the temperature control element comprises a first temperature zone and a second temperature zone, wherein the first temperature zone is hotter than the second temperature zone.

In one aspect, aligning the temperature control element and the second-stage reaction zone in step (f) includes repeatedly translating the temperature control element relative to the second-stage reaction zone. In another aspect, aligning the temperature control element and the second-stage reaction zone in step (f) includes repeatedly translating the second-stage reaction zone relative to the temperature control element.

In one aspect, the instrument further includes a wiper element, and step (d) further includes aligning the wiper element with the temperature control element and the first-stage chamber such that rotational movement of the wiper element moves a first portion of the sample from thermal control of the first temperature zone to thermal control of the second temperature zone, while simultaneously moving a second portion of the sample from thermal control of the second temperature zone to thermal control of the first temperature zone.

In one aspect, the sample container includes a sample preparation zone fluidly connected to the first-stage chamber, and, prior to step (d), the method further includes: introducing the sample into the sample preparation zone, contacting the sample preparation zone with a lysis apparatus to produce a lysate, recovering nucleic acids from the lysate, and moving the recovered nucleic acids into the first-stage chamber. In another aspect, recovering nucleic acids from the sample further includes: contacting the lysate with a plurality of magnetic beads, deploying a magnet to separate the magnetic beads from the lysate, washing the magnetic beads, recapturing the magnetic beads with the magnet, contacting the magnetic beads with an elution buffer to release the nucleic acids from the magnetic beads, and recapturing the magnetic beads with the magnet and separating the eluted nucleic acids from the magnetic beads.

In one aspect, the step (f) of the method includes aligning the second nucleic acid amplification zone with the first temperature zone and then the second temperature zone of the temperature control element to thermocycle the sample in the second nucleic acid amplification zone.

In one aspect, the steps of the method may be are completed in 20 minutes or less, 15 minutes or less, or, preferably, 10 minutes or less. In another aspect, each thermal cycle of the first and second nucleic acid amplification zones is completed in 8 seconds or less, 6 seconds or less, or, preferably, 4 seconds or less.

In another embodiment, an instrument for thermocycling a sample provided in a flexible sample container is described. The instrument includes a first heater adjacent to a first portion of the flexible sample container for adjusting a first portion of the sample to a first temperature, a second heater adjacent to a second portion of the flexible sample container for adjusting a second portion of the sample to a second temperature, the second temperature different from the first temperature, and a wiper element that moves the first portion of the sample to the second portion of the flexible sample container while moving the second portion of the sample to the first portion of the flexible sample container such that portions of the sample are under control of each of the heaters simultaneously. In one aspect, the wiper element includes a blade that divides the sample into at least two discrete sections comprising at least a first section and a second section, such that the first portion is contained in the first section and the second portion is contained in the second section. In one aspect, the wiper element repeatedly moves portions of the sample to opposite portions of the sample container to thermocycle the sample.

In an embodiment, another instrument for thermocycling a sample is described. The instrument includes a receptacle for positioning a flexible sample container having at least a first reaction chamber in the instrument, and a heater assembly that includes a first heater element and a second heater element, and a translator mechanically coupled to at least one of the receptacle, the flexible sample container, or the heater assembly to laterally align the first reaction chamber relative to the first and second heater elements of the heater assembly such that the first reaction chamber is under temperature control of at least one of the first or the second heater elements. Wherein the instrument is configured to repeatedly align the first reaction chamber with the first heater element and then the second heater element for thermocycling a fluid sample in the at least one reaction chamber.

In yet another embodiment, a thermocycling system is described. The thermocycling system includes a receptacle for receiving a flexible sample container therein, the flexible sample container having a first-stage chamber including a sample to be thermocycled therein, a heater element that includes at least a first temperature zone and a second temperature zone positioned on a first side of the flexible sample container, and a wiper element positioned on a second side of the sample container, the wiper element being configured for contacting the first-stage chamber to divide the sample into at least a first portion and a second portion. Wherein one or more of the receptacle, the heater element, the wiper element, or the flexible sample container are movable such that movement aligns the first-stage chamber relative to the wiper element and the first and second temperature zones of the heater element, and wherein the wiper element is configured to rotate adjacent to the first-stage chamber to move the first portion of the sample to the second portion while moving the second portion of the sample to the first portion such that the first and second portion are under temperature control of the first and second temperature zones of the heater element.

In yet another embodiment, another instrument for thermocycling a sample is described. The instrument includes a receptacle for positioning a flexible sample container in the instrument. In one embodiment, the flexible sample container includes a first-stage chamber and a second-stage reaction chamber having an array of second-stage reaction wells. The instrument further includes a heater element comprising at least a first temperature zone and a second temperature zone, wherein one or more of the receptacle, the sample container, or the heater element are movable such that movement aligns the first-stage chamber and the second-stage reaction chamber relative to the heater element, and wherein the receptacle and the heater element are configured to allow the heater element to heat first the first-stage chamber and second the second-stage reaction chamber to effect thermal cycling and nucleic acid amplification in the first-stage chamber and then the second-stage reaction chamber.

In one aspect, the instrument further includes a wiper element having at least one blade configured to contact the first-stage chamber and divide the first-stage chamber into at least a first volume and a second volume. Wherein the heater element is aligned beneath the first-stage chamber such that the first volume is positioned over the first temperature zone and a second volume is positioned over the second temperature zone, and wherein the wiper element is configured to rotate to move the first volume to the second temperature zone while moving the second volume to the first temperature zone such that first and second volumes are under control of each of the temperature zones.

In yet another embodiment, yet another instrument for thermocycling a sample is described. The instrument includes a receptacle for positioning a flexible sample container in the instrument. In one aspect, the flexible sample container includes at least one reaction chamber. The instrument further includes a heater assembly that includes a first heater element, a second heater element, and a third heater element. Wherein the first and third heater elements are held at a temperature higher than the second heater element, and wherein the instrument is configured to align the at least one reaction chamber with the first heater element, the second heater element, and the third heater element for thermocycling a fluid sample in the at least one reaction chamber. In one aspect, the first and third heater elements are set at a temperature in a range of about 90° C.-110° C. and the second heater element is set to a temperature of about 55° C.-65° C.

In still yet another embodiment, a polymerase chain reaction method using the instrument described in the previous paragraph is included. The method includes (a) providing the sample container comprising the at least one reaction chamber, (b) introducing a sample into the reaction chamber, wherein the sample includes a target nucleic acid, at least one primer for amplifying the target nucleic acid, and a thermostable DNA polymerase, (c) inserting the sample container into the instrument, (d) aligning the first heater element with the reaction chamber, then aligning the second heater element with the reaction chamber, and then aligning third heater element with the reaction chamber. Wherein the first and third heater elements are set at a denaturation temperature and the second heater is set at an annealing temperature, and wherein step (d) comprises one cycle of denaturation, annealing, and elongation/denaturation. The method further includes repeating step (d) for a selected number of cycles (at least once) to accomplish nucleic acid amplification.

In still yet another embodiment, yet another instrument for amplifying nucleic acids is described. The nucleic acids are provided in a sample container wherein the nucleic acids are configured in an array. The instrument includes an opening for receiving the sample container, a plurality of heaters, each heater provided at a different temperature, and a mover for moving the heaters sequentially to a position adjacent to the opening, such that only the heater in the position controls temperature of the nucleic acids in the sample container. In one aspect, the sample container further includes components for amplifying nucleic acids, and the plurality of heaters includes at least a first heater at an annealing temperature and a second heater at a denaturation temperature. In another aspect, the plurality of heaters further includes a third heater at an elongation temperature.

In still yet another embodiment, yet another method for performing PCR is described. The method includes (a) providing a PCR mixture in a sample vessel the PCR mixture having a volume, (b) thermocycling for a first number of cycles, each of the first number of cycles having a first cycle time, (c) reducing the volume of the PCR mixture in the sample container to a second volume, the second volume being smaller than the first volume, and (d) thermocycling for a second number of cycles, each of the second number of cycles having a second cycle time, the second cycle time being shorter than the first cycle time. In one aspect, the method further includes (e) reducing the volume of the PCR mixture in the sample container to a third volume, the third volume being smaller than the second volume, and (f) thermocycling for a third number of cycles, each of the second number of cycles having a third cycle time, the third cycle time being shorter than the second cycle time.

In still yet another embodiment, yet another method of amplifying nucleic acids in a sample is described. The method includes introducing a fluid sample into a sample compartment of a container, the fluid sample containing a target nucleic acid and reagents for amplifying the target nucleic acid, introducing the container into a heating apparatus, the heating apparatus including a first heater, a second heater, and a mover (e.g., a wiper or a squisher) for moving the fluid sample within the sample compartment, the first heater being set to a first temperature and the second heater being set to a second temperature, the first temperature being greater than the second temperature, a first part of the sample compartment being disposed proximal to the first heater so that the first heater exhibits thermal control on the first part of the sample compartment and a second part of the sample compartment being disposed proximal to the second heater so that the second heater exhibits thermal control on the second part of the sample compartment, and selectively moving at least a portion of the fluid sample between the first part of the sample compartment and the second part of the sample compartment, such that portions of the sample are under control of each of the heaters simultaneously.

In still yet another embodiment, yet another method of amplifying nucleic acids in a sample is described. The method includes (a) introducing a fluid sample into a first compartment of a container, the fluid sample comprising a target nucleic acid and reagents for amplifying the target nucleic acid, wherein the first compartment is under control of a first heater that is set at a temperature that is below an annealing temperature (a low annealing temperature), (b) raising the temperature of the first heater to the annealing temperature, (c) moving the fluid sample into a second compartment of a container, wherein the second compartment is under control of a second heater that is set at a temperature that is above an elongation temperature (a high elongation temperature), and lowering the temperature of the first heater to the low annealing temperature subsequent to moving the fluid sample into the second compartment, (d) lowering the temperature of the second heater to the elongation temperature, (e) raising the temperature of the second heater to at least a denaturation temperature, and (f) repeating steps (a) through (e). In one aspect, when step (a) is repeated, the temperature of the second heater is moved to the high elongation temperature. In another aspect, step (e) includes raising the temperature of the second heater to a temperature above the denaturation temperature, and step (a) is repeated as soon as the fluid sample reaches the denaturation temperature.

In still yet another embodiment, yet another instrument is provided for thermocycling a sample provided in a flexible sample container having at least a first-stage chamber. In one embodiment, the instrument includes a receptacle for positioning the flexible sample container in the instrument and a heater element that includes at least a first temperature zone and a second temperature zone. Wherein one or more of the receptacle or the heater element are movable such that movement positions the first-stage chamber relative to the first temperature zone and the second temperature zone of the heater element, and wherein the receptacle and the heater element are configured to allow the first temperature zone and the second temperature zone to control the temperature of the first-stage chamber to effect thermal cycling and nucleic acid amplification therein.

In one aspect, the heater element may be positionable beneath the first-stage chamber such that a first portion of the sample may be positioned over the first temperature zone and a second portion of the sample may be positioned over the second temperature zone. The instrument further includes a mixing component having a wiper with at least one blade that may be configured to contact the first-stage chamber and to rotate to move the first portion of the sample to the second temperature zone while moving the second portion of the sample to the first temperature zone such that first and second portions of the sample may be under control of each of the temperature zones to effect thermal cycling and nucleic acid amplification of the contents of the first-stage chamber.

In another aspect, the flexible sample container may include a sample preparation zone where, for example, cells in a sample may be lysed and nucleic acids may be recovered for amplification in the first-stage chamber. In another aspect, the flexible sample container may include a second nucleic acid amplification zone downstream from the first-stage chamber. The second nucleic acid amplification zone may be configured to receive a portion of a diluted amplification product from the first-stage chamber and further amplify the diluted amplification product in an array of wells with specific primer sets selected for assaying the contents of the sample.

In still yet another embodiment, yet another instrument for amplifying nucleic acids in a sample is described. The instrument includes an opening for receiving a flexible sample container, the flexible sample container comprising at least one reaction zone, and a plurality of heaters, wherein each of the heaters is configured to be set at a different temperature, and wherein the heaters are positioned on a substantially planar mount such that each heater can be sequentially aligned with the at least one reaction zone to heat or cool a sample therein. In one aspect, the substantially planar mount comprises a circular mount that is configured to be rotated adjacent to the flexible sample container.

The instruments and methods described herein may include or be configured for automated sample preparation, first-stage PCR, second-stage PCR, and automated analysis of the second-stage PCR product in the flexible sample container. For instance, one or more of the receptacle, the heater element, or the mixing component may be positionable relative to the flexible sample container for heated and chilled sample preparation, first-stage PCR, and second stage PCR.

In still yet another embodiment a flexible sample container is described. The flexible sample container includes a reaction chamber having an array of reaction wells, wherein each of the wells of the array is fluidly connected to a selectively openable and selectively sealable fill channel and fill hole. In one aspect, the fill hole is fluidly connected to a well filling channel that flows adjacent to and over a well of the array, wherein the well filling channel is formed by making a cutout in a layer adjacent to the well of the array and another cutout in a second layer. In another aspect, the fill hole is fluidly connected to a well filling channel that flows into a well of the array, wherein the well filling channel is formed by making a cutout in a layer that fluidly connects the fill hole to the well of the array.

Additional features and advantages of the embodiments of the invention will be set forth in the description which follows or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 14A shows a flexible pouch useful for self-contained PCR.

FIG. 14B shows a partial cross-sectional view of the pouch of 14A along the line B-B.

FIG. 25 depicts the increase in florescence in the wells of the second-stage PCR array as a function of cycle number. FIGS. 26 and 27 depict the results of a melting experiment to ensure that the product being amplified is the correct product. FIG. 26 is a raw melting curve and FIG. 27 depicts a negative first derivative (dF/dt) of the melting curve.

FIG. 28 illustrates the temperature response with an 8 sec. cycle time (4 sec. holds at each temperature), FIG. 29 illustrates another temperature response experiment with an 8 sec. cycle time, FIG. 30 illustrates the temperature response with an 4 sec. cycle time (2 sec. holds at each temperature), and FIG. 31 illustrates the temperature response with a 2 sec. cycle time (1 sec. holds at each temperature).

DETAILED DESCRIPTION

Figure 1:
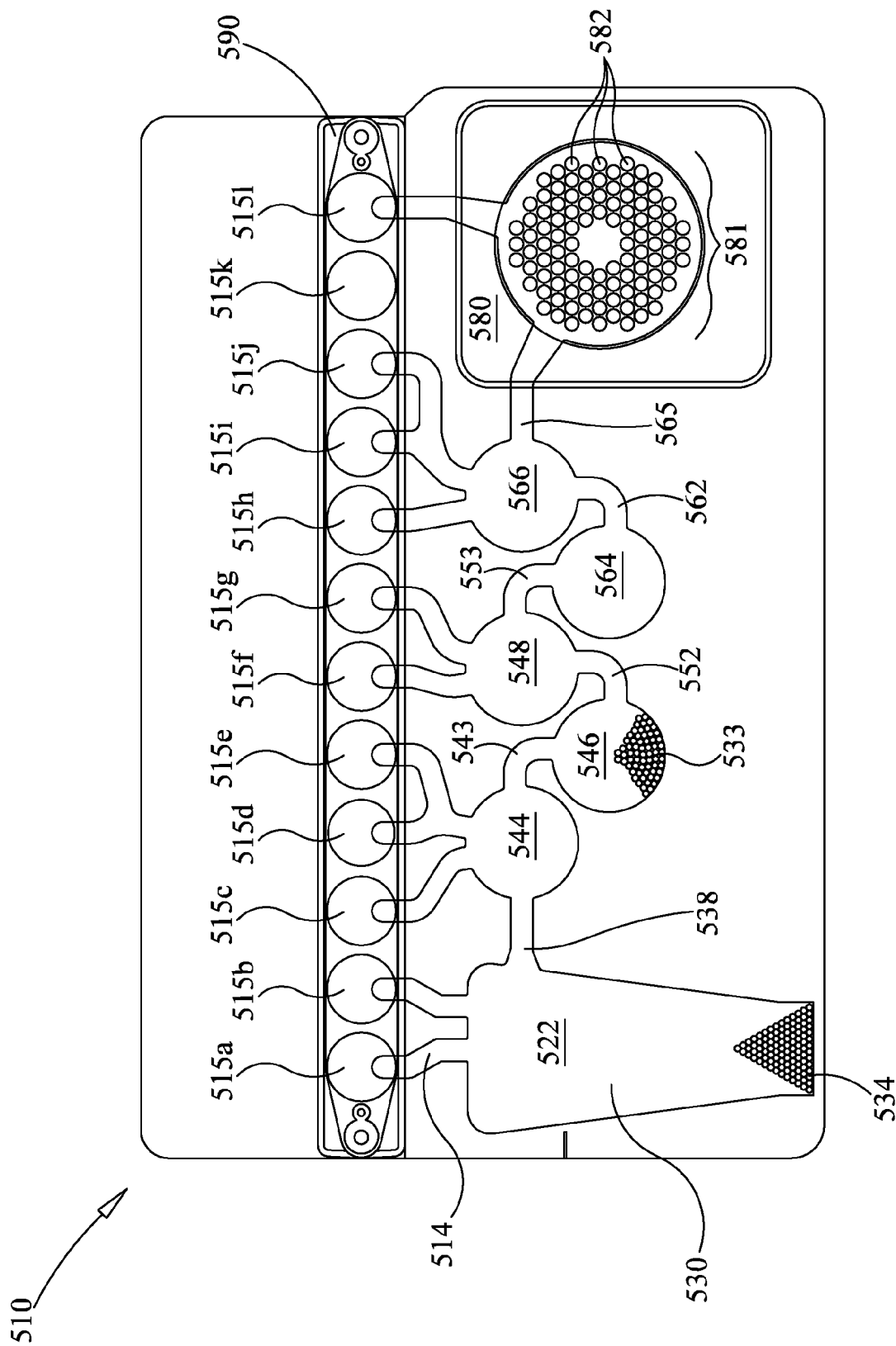
FIG. 1 shows a flexible pouch useful for self-contained PCR.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference for in their entirety. In case of a conflict in terminology, the present specification is controlling.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an," and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present inventive concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatuses, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within that implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a non-naturally occurring nucleic acid, which is assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids. Samples may also include environmental samples such as, but not limited to, soil, water (fresh water, waste water, etc.), air monitoring system samples (e.g., material captured in an air filter medium), surface swabs, and vectors (e.g., mosquitos, ticks, fleas, etc.).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, mRNA, rRNA, cDNA, gDNA, ssDNA, dsDNA, or any combination thereof.

By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant typically to occur at about a melting temperature (Tm) minus 5° C. (i.e. 5° below the Tm of the probe). Functionally, high stringency conditions are used to identify nucleic acid sequences having at least 80% sequence identity.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, reaction time may be used where measurements are made in cycles, doubling time, or crossing point (Cp), and additional reaction time may be added where additional PCR cycles are added in the embodiments described herein. It is understood that protocols may need to be adjusted accordingly.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; and U.S. patent application Ser. No. 2014-0283945, herein incorporated by reference. However, it is understood that such pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art. While the terms "sample well", "amplification well", "amplification container", or the like are used herein, these terms are meant to encompass wells, tubes, and various other reaction containers, as are used in these amplification systems. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels 515*a* through 515*l*, which also serve as reagent reservoirs or waste reservoirs. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 1 is similar to that of U.S. Pat. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510 is suitable for use in the FilmArray® instrument (BioFire Diagnostics, LLC, Salt Lake City, Utah). However, it is understood that the pouch embodiment is illustrative only.

While other containers may be used, illustratively, pouch 510 may be formed of two layers of a flexible plastic film or other flexible material such as polyester, polyethylene terephthalate (PET), polycarbonate, polypropylene, polymethylmethacrylate, mixtures, combinations, and layers thereof that can be made by any process known in the art, including extrusion, plasma deposition, and lamination. For instance, each layer can be composed of one or more layers of material of a single type or more than one type that are laminated together. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, DuPont, Wilmington, Del.) of about 0.0048 inch (0.1219 mm) thick and polypropylene films of 0.001-0.003 inch (0.025-0.076 mm) thick perform well. Illustratively, pouch 510 may be made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of the pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material. Thus, it is understood that when the terms "flexible pouch" or "flexible sample container" or the like are used, only portions of the pouch or sample container need be flexible.

Illustratively, a plastic film may be used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton Wis.), illustratively regulated at an operating temperature of 195° C., the pneumatic press works like a printing press, melting the sealing surfaces of plastic film only where the die contacts the film. Likewise, the plastic film(s) used for pouch 510 may be cut and welded together using a laser cutting and welding device. Various components, such as PCR primers (illustratively spotted onto the film and dried), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction may be hydrated by an aqueous sample. If the aqueous sample has been heated prior to hydration, this creates the conditions for a true hot-start PCR and reduces or eliminates the need for expensive chemical hot-start components. In another embodiment, components may be provided in powder or pill form and are placed into blisters prior to final sealing.

Pouch 510 may be used in a manner similar to that described in U.S. Pat. No. 8,895,295. In one illustrative embodiment, a 300 µl mixture comprising the sample to be tested (100 µl) and lysis buffer (200 µl) may be injected into an injection port (not shown) in fitment 590 near entry channel 515a, and the sample mixture may be drawn into entry channel 515a. Water may also be injected into a second injection port (not shown) of the fitment 590 adjacent entry channel 515l, and is distributed via a channel (not shown) provided in fitment 590, thereby hydrating up to eleven different reagents, each of which were previously provided in dry form at entry channels 515b through 515l. Illustrative methods and devices for injecting sample and hydration fluid (e.g. water or buffer) are disclosed in U.S. patent application Ser. No. 2014-0283945, herein incorporated by reference in its entirety, although it is understood that these methods and devices are illustrative only and other ways of introducing sample and hydration fluid into pouch 510 are within the scope of this disclosure. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed. For more information on various configurations of pouch 510 and fitment 590, see U.S. Pat. No. 8,895,295, already incorporated by reference.

After injection, the sample may be moved from injection channel 515a to lysis blister 522 via channel 514. Lysis blister 522 is provided with beads or particles 534, such as ceramic beads or other abrasive elements, and is configured for vortexing via impaction using rotating blades or paddles provided within the FilmArray® instrument. Bead-milling, by shaking, vortexing, sonicating, and similar treatment of the sample in the presence of lysing particles such as zirconium silicate (ZS) beads 534, is an effective method to form a lysate. It is understood that, as used herein, terms such as "lyse," "lysing," and "lysate" are not limited to rupturing cells, but that such terms include disruption of non-cellular particles, such as viruses.

Figure 2:
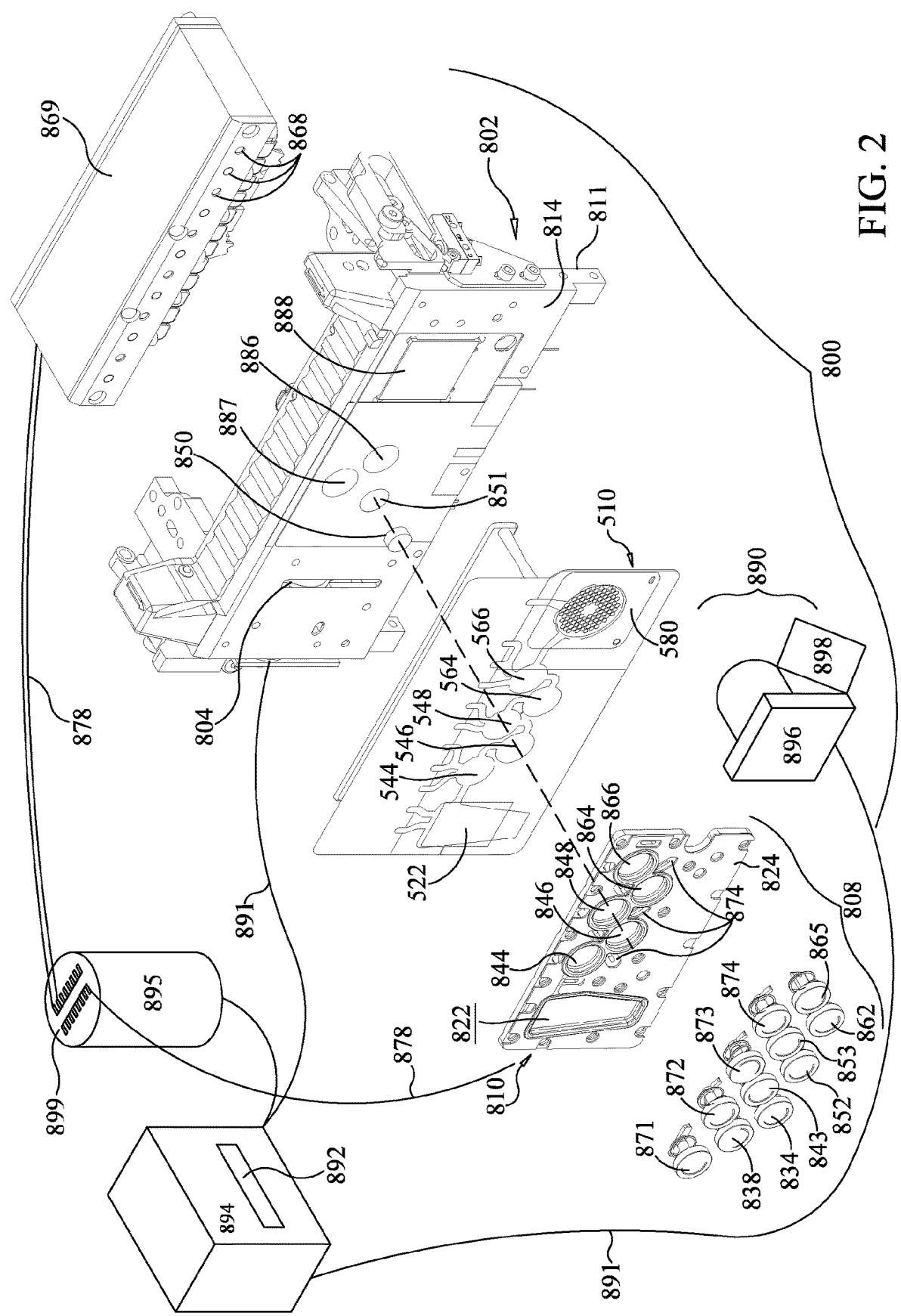
FIG. 2 is an exploded perspective view of an instrument for use with the pouch of FIG. 1, including the pouch of FIG. 1, according to an example embodiment of the present invention.
Figure 4:
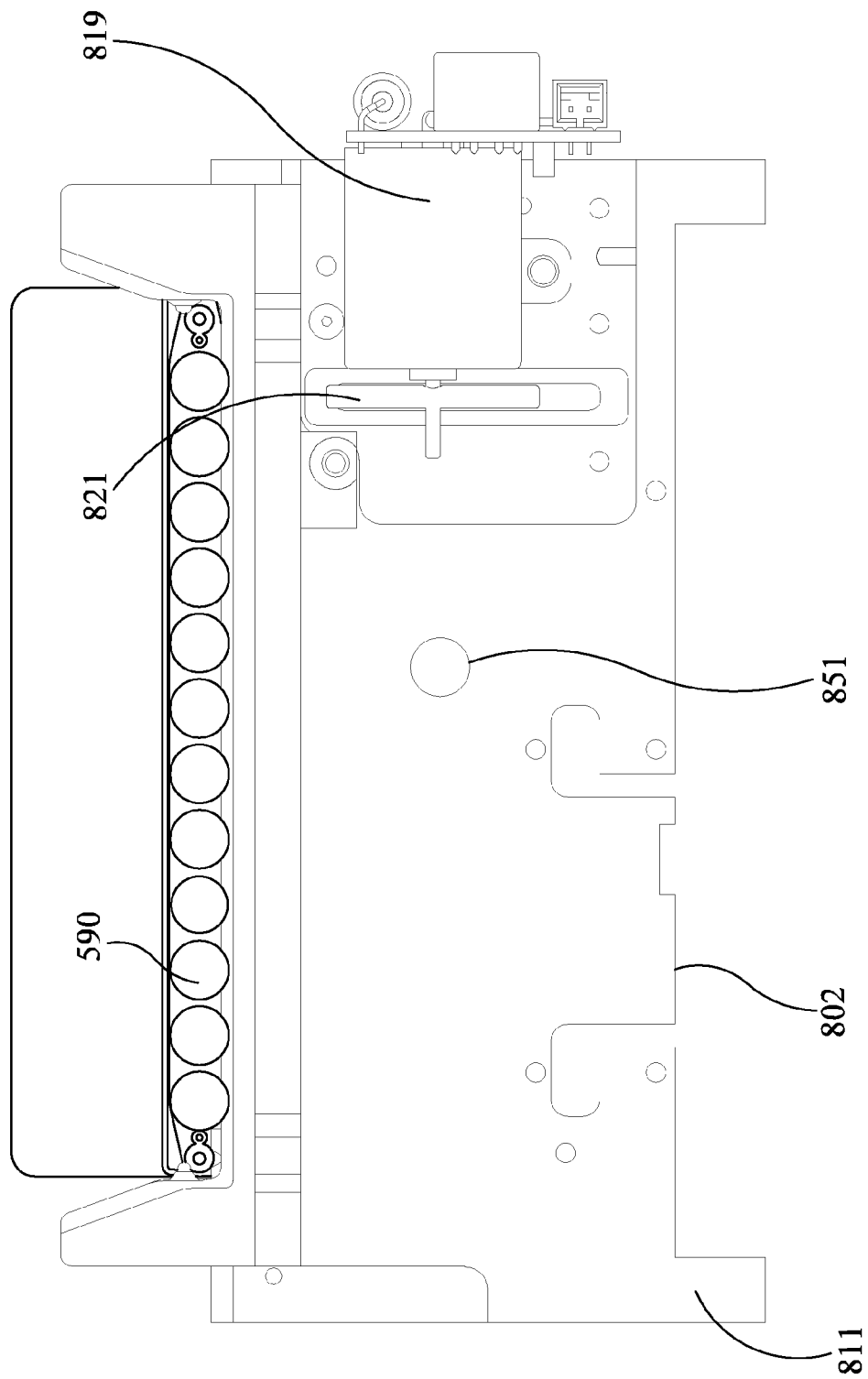
FIG. 4 shows a motor used in one illustrative embodiment of the instrument of FIG. 2.
Figure 5B:
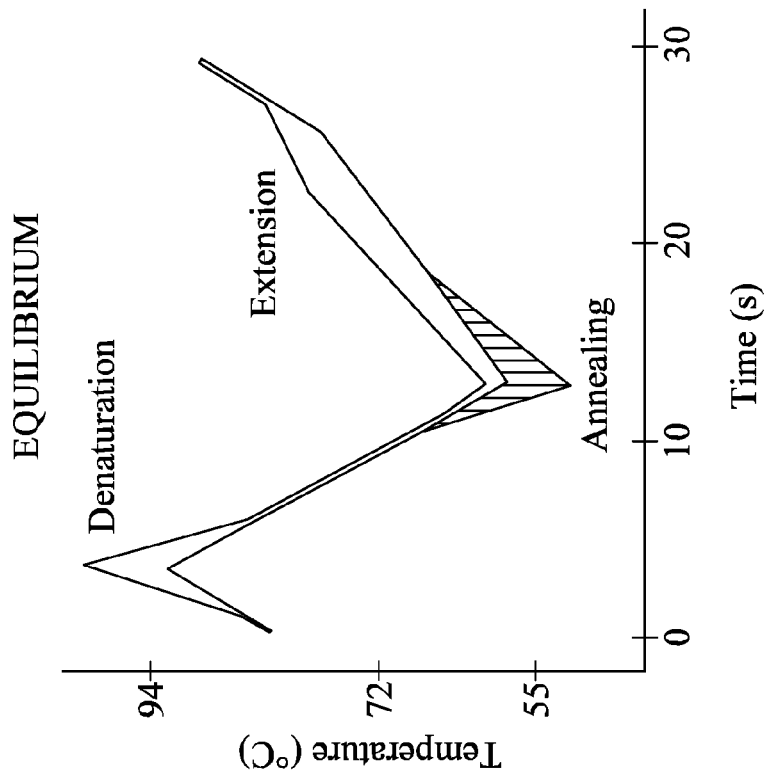
FIGS. 5A-5B show illustrative profiles for an equilibrium paradigm (FIG. 5*a*) and a kinetic paradigm (FIG. 5*b*) of PCR. Solid black represents denaturation, striped represents annealing, and solid white represents extension of the nucleic acids during thermal cycling.
Figure 5A:
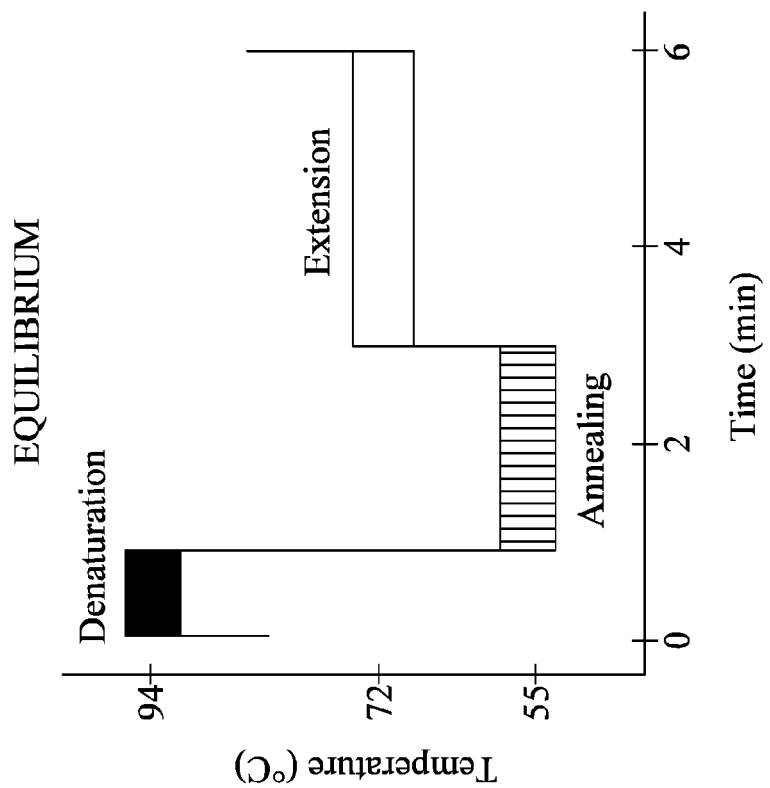

FIG. 4 shows a bead beating motor 819, comprising blades 821 that may be mounted on a first side 811 of support member 802, of instrument 800 shown in FIG. 2. Blades may extend through slot 804 to contact pouch 510. It is understood, however, that motor 819 may be mounted on other structures of instrument 800. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample. In some embodiments, chemicals or heat may be used in addition to or instead of mechanical lysis.

Once the sample material has been adequately lysed, the sample is moved to a nucleic acid extraction zone, illustratively through channel 538, blister 544, and channel 543, to blister 546, where the sample is mixed with a nucleic acid-binding substance, such as silica-coated magnetic beads 533. Alternatively, magnetic beads 533 may be rehydrated, illustratively using fluid provided from one of the entry channel 515c-515e, and then moved through channel 543 to blister 544, and then through channel 538 to blister 522. The mixture is allowed to incubate for an appropriate length of time, illustratively approximately 10 seconds to 10 minutes. A retractable magnet located within the instrument adjacent blister 546 captures the magnetic beads 533 from the solution, forming a pellet against the interior surface of blister 546. If incubation takes place in blister 522, multiple portions of the solution may need to be moved to blister 546 for capture. The liquid is then moved out of blister 546 and back through blister 544 and into blister 522, which is now used as a waste receptacle. One or more wash buffers from one or more of injection channels 515c to 515e are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533.

After washing, elution buffer stored at injection channel 515f is moved to blister 548, and the magnet is retracted. The solution is cycled between blisters 546 and 548 via channel 552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

First-stage PCR master mix from injection channel 515g is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target, and first-stage multiplex PCR is performed. If RNA targets are present, an RT step may be performed prior to or simultaneously with the first-stage multiplex PCR. First-stage multiplex PCR temperature cycling in the FilmArray® instrument is illustratively performed for 15-20 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in US2015/0118715, herein incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515i. Alternatively, a dilution buffer from 515i may be moved to blister 566 then mixed with the amplified sample in blister 564 by moving the fluids back and forth between blisters 564 and 566. If desired, dilution may be repeated several times, using dilution buffer from injection channels 515j and 515k, or injection channel 515k may be reserved, illustratively, for sequencing or for other post-PCR analysis, and then adding second-stage PCR master mix from injection channel 515h to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is pre-loaded with a specific PCR primer pair. If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously or individually thermal cycled, illustratively with one or more Peltier devices, although other means for thermal cycling are known in the art.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, wells 582 of array 581 may be provided without a signal, with results reported through subsequent processing.

Figure 3:
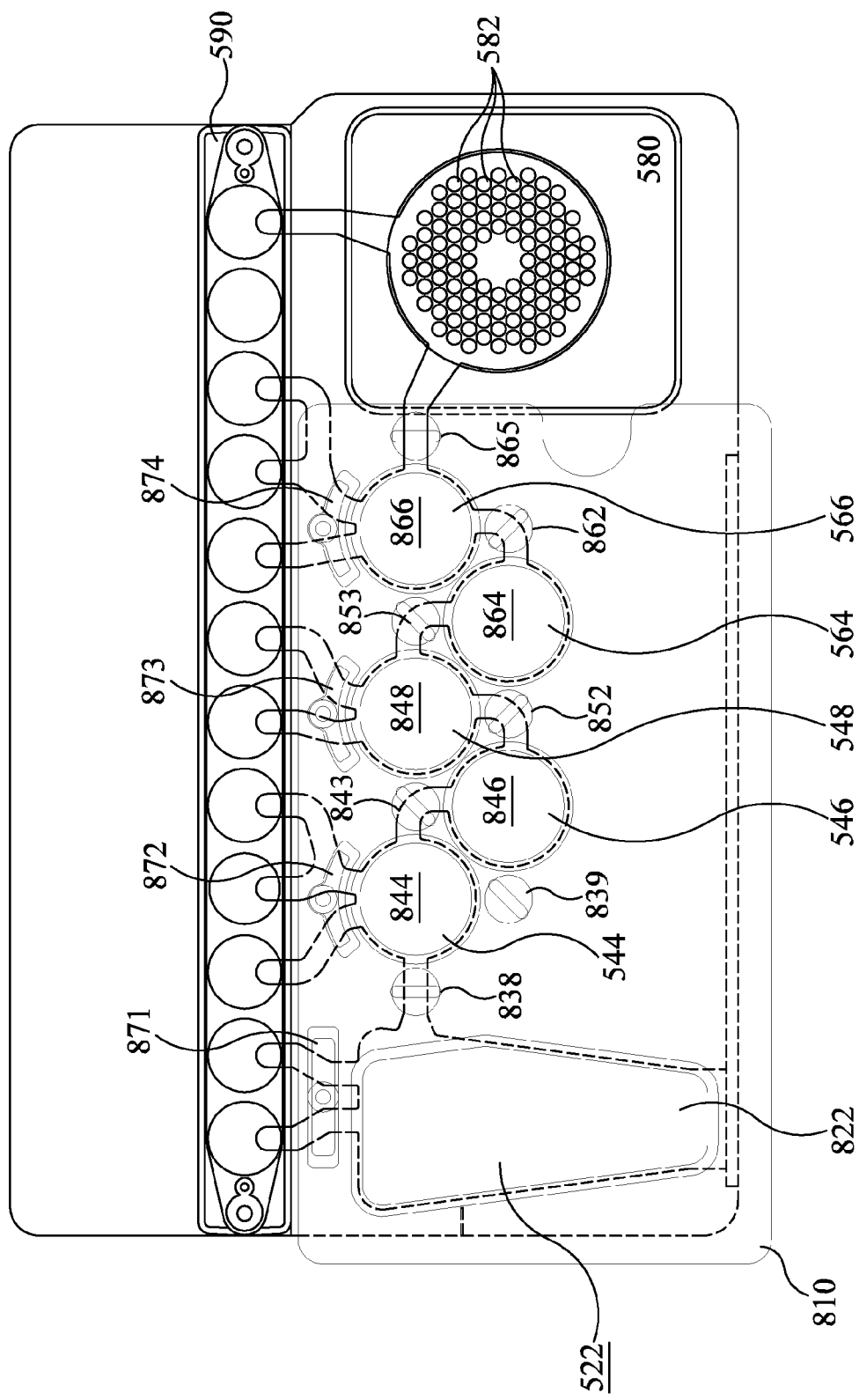
FIG. 3 shows a partial cross-sectional view of the instrument of FIG. 2, including the bladder components of FIG. 2, with the pouch of FIG. 1 shown in dashed lines.

When pneumatic pressure is used to move materials within pouch 510, in one embodiment, a "bladder" may be employed. The bladder assembly 810, a portion of which is shown in FIGS. 2-3, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of this invention. Alternatively, an array or mechanical actuators and seals may be used to seal channels and direct movement of fluids between blisters. A system of mechanical seals and actuators that may be adapted for the instruments described herein is described in detail in U.S. Prov. App. Ser. No. 62/368,095, the entirety of which is incorporated herein by reference.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of Taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 2-3 show an illustrative plurality of pistons or hard seals 838, 843, 852, 853, and 865 that correspond to channels 538, 543, 553, and 565 of pouch 510, as well as seals 871, 872, 873, 874 that minimize backflow into fitment 590. When activated, hard seals 838, 843, 852, 853, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch 510 could be transitioned such that a small number of actuators could be used for several of the processing stations including sample disruption, nucleic-acid capture, first and second-stage PCR, and processing stations for other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

Turning back to FIG. 2, each pneumatic actuator is connected to compressed air source 895 via valves 899. While only several hoses 878 are shown in FIG. 2, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention. Similar pneumatic control may be provided in the embodiments of FIGS. 12-16, for control of fluids in pouch 1400, or other actuators, servos, or the like may be provided.

Several other components of instrument 810 are also connected to compressed gas source 895. A magnet 850, which is mounted on a second side 814 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is fully retracted, magnet 850 does not significantly affect any magnetic beads 533 present in blister 546. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required. It is understood that similar magnets and methods for activating the magnets may be used in the embodiments of FIGS. 12-16.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown.

A pair of temperature control elements are mounted on a second side 814 of support 802. As used herein, the term "temperature control element" refers to a device that adds heat to or removes heat from a sample. Illustrative examples of a temperature control element include, but are not limited to, heaters, coolers, Peltier devices, resistance heaters, induction heaters, electromagnetic heaters, thin film heaters, printed element heaters, positive temperature coefficient heaters, and combinations thereof. A temperature control element may include multiple heaters, coolers, Peltiers, etc. In one aspect, a given temperature control element may include more than one type of heater or cooler. For instance, an illustrative example of a temperature control element may include a Peltier device with a separate resistive heater applied to the top and/or the bottom face of the Peltier. While the term "heater" is used throughout the specification, it is understood that other temperature control elements may be used to adjust the temperature of the sample.

As discussed above, first-stage heater 886 may be positioned to heat and cool the contents of blister 564 for first-stage PCR. As seen in FIG. 2, second-stage heater 888 may be positioned to heat and cool the contents of second-stage blisters 582 of array 581 of pouch 510, for second-stage PCR. It is understood, however, that these heaters could also be used for other heating purposes, and that other heaters may be included, as appropriate for the particular application.

Figure 18:
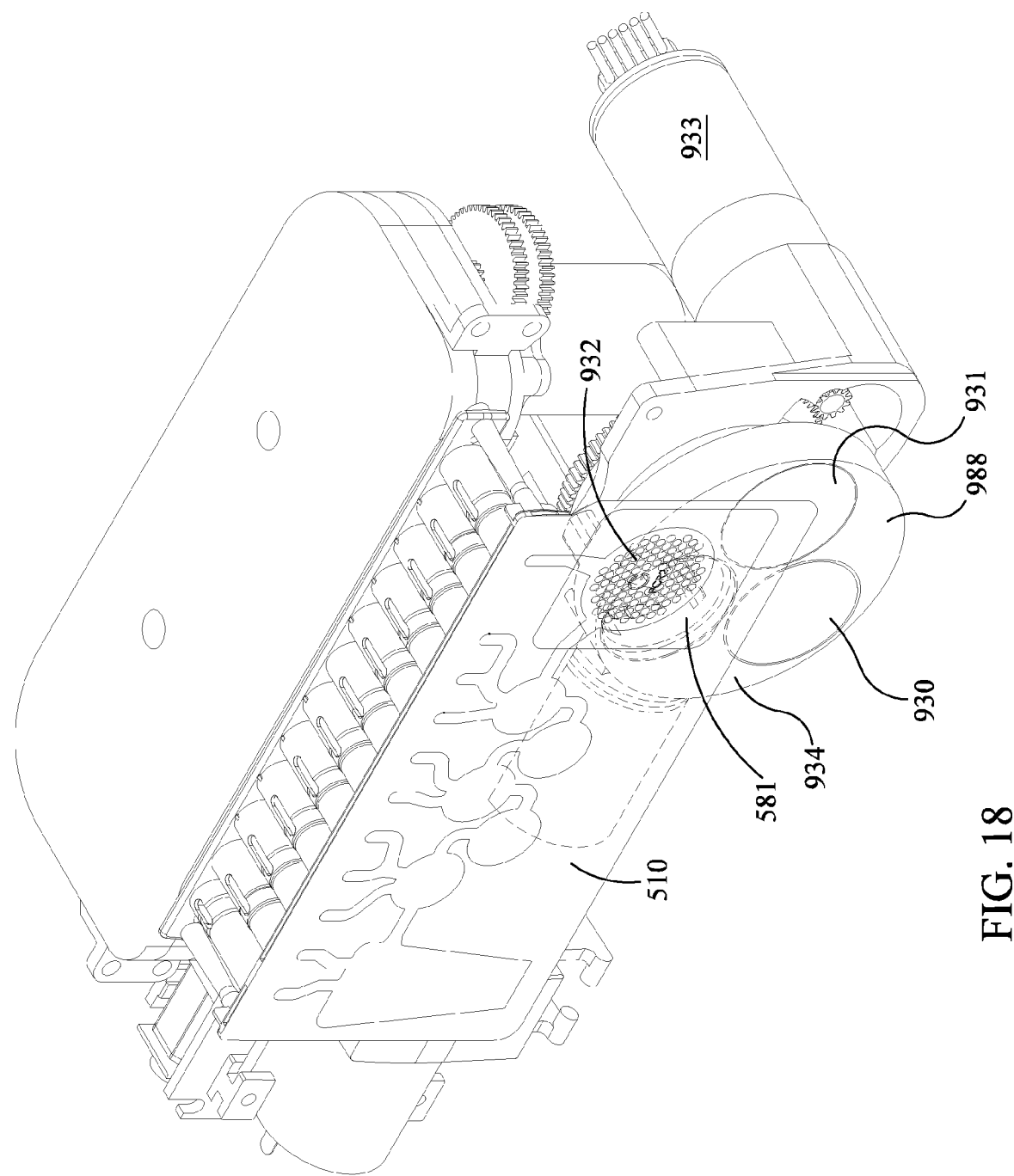
FIG. 18 is a perspective view of an alternative heating embodiment for second-stage PCR for the instrument of FIG. 2

As discussed above, while Peltier devices, which thermocycle between two or more temperatures, are effective for PCR, it may be desirable in some embodiments to maintain heaters at a constant temperature. Illustratively, this can be used to reduce run time, by eliminating time needed to transition the heater temperature beyond the time needed to transition the sample temperature. Also, such an arrangement can improve the electrical efficiency of the system as it is only necessary to thermally cycle the smaller sample and sample vessel, not the much larger (more thermal mass) Peltier devices. FIG. 18 shows an alternative embodiment for second-stage heater 888, which is replaced by heater assembly 988. Illustratively, heater assembly 988 includes three heaters 930, 931, and 932, set in an illustratively circular mount 934, driven circularly by motor 933, so that one heater at a time contacts array 581 as each heater is moved sequentially into position adjacent array 581. Types of suitable heaters have been discussed above, with reference to first-stage PCR. Illustratively, heater 930 may be set at an annealing temperature, illustratively 60° C., heater 931 may be set at an elongation temperature, illustratively 72° C., and heater 932 may be set at a denaturation temperature, illustratively 94° C. However, it is understood that these temperatures are illustrative only, and that other temperatures and other numbers of heaters may be used. Two heaters may be sufficient for many applications. In this embodiment, heaters 930, 931, 932 move to contact array 581. Mount 934 may move in one direction only, with each of heaters 930, 931, 932 contacting array 581 in order, or mount may move in both clockwise and counterclockwise directions, illustratively changing direction after each PCR cycle.

Figure 6:
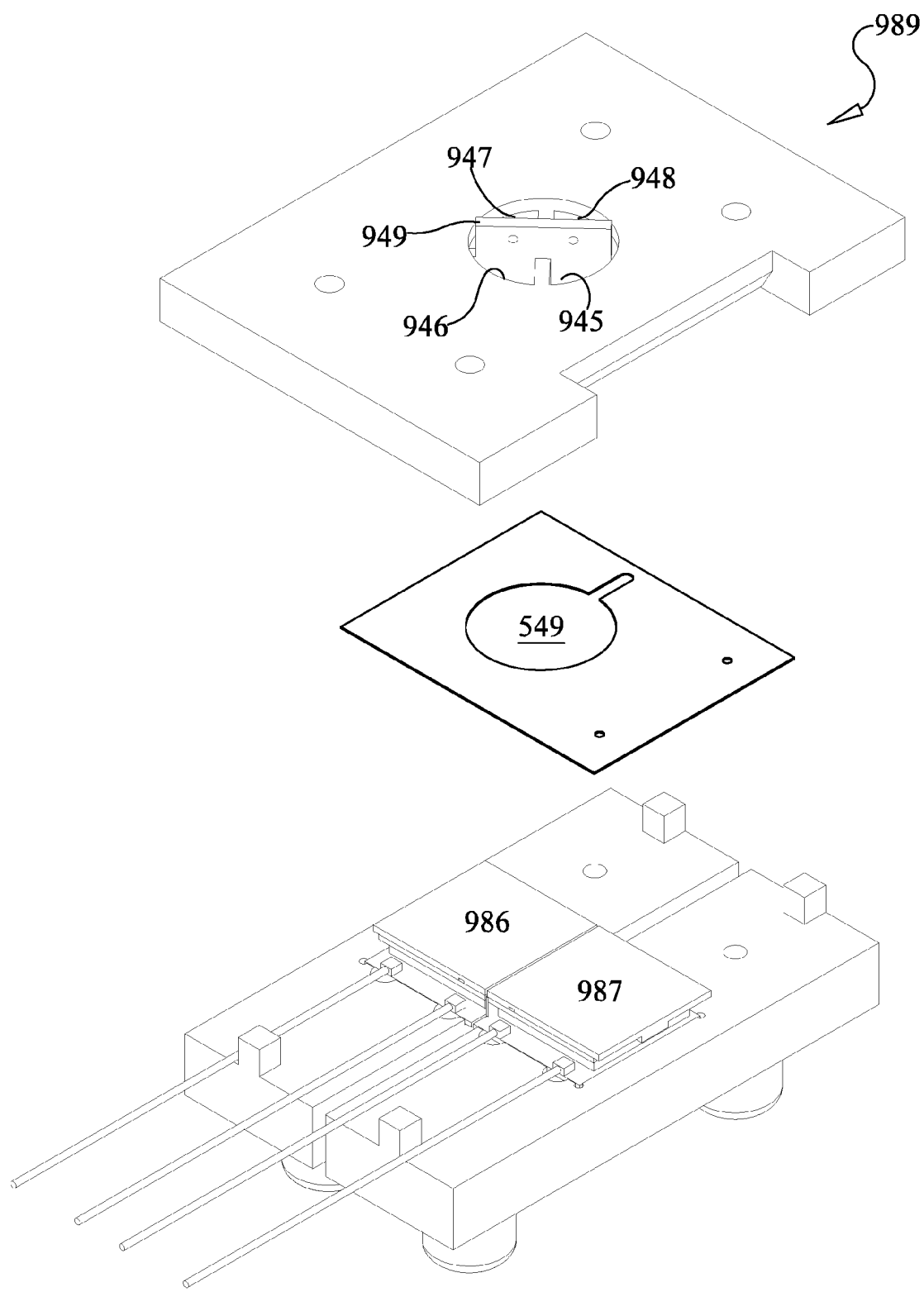
FIG. 6 is an exploded view of an alternative heating embodiment for first-stage PCR for the instrument of FIG. 2.
Figure 7:
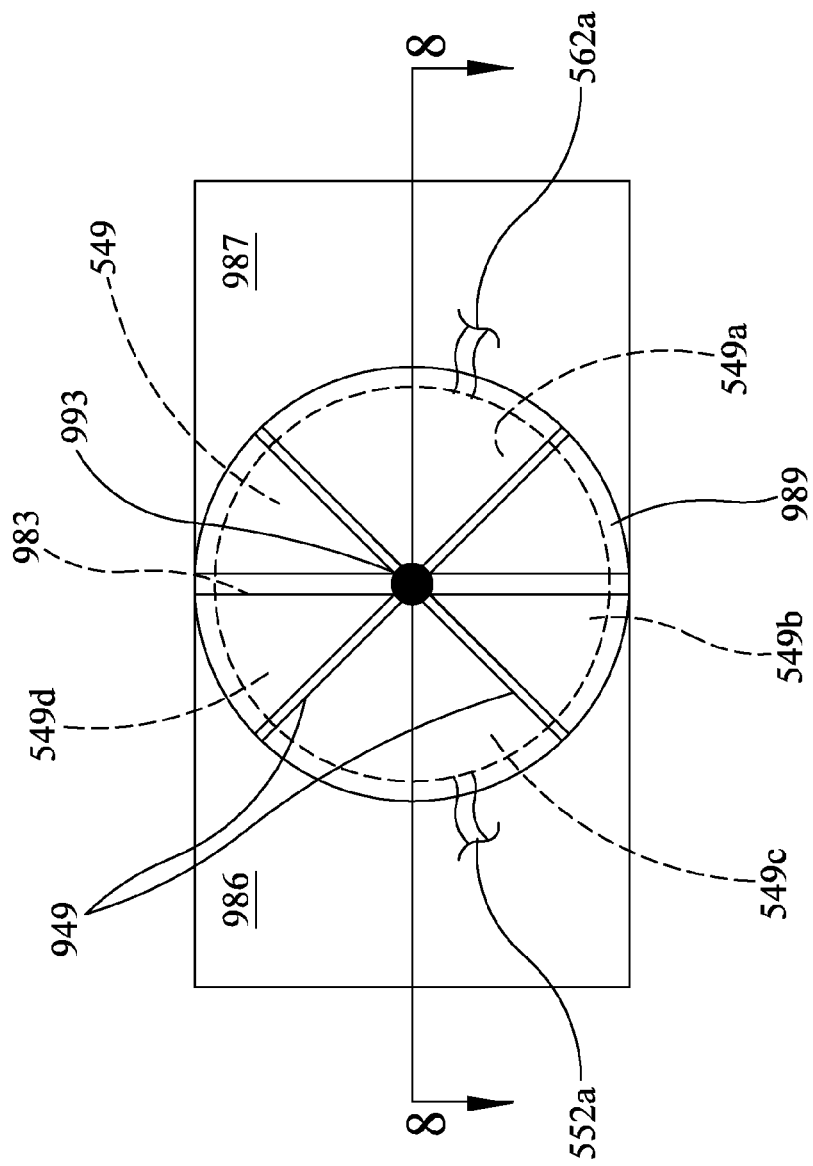
FIG. 7 is a top view of the heating format of FIG. 6.

While heaters 930, 931, 932 are provided in mount 934 and are moved relative to array 581, it is understood that this is illustrative only, and that two or more stationary heaters may be provided, and array 581 may be rotated relative to the heaters, as with the embodiment shown in FIGS. 6-8 for first stage PCR. Likewise, the heaters may be arranged linearly as in the embodiments illustrated in, for example, FIGS. 12A-13B and FIG. 17. In such an example, thermocycling may be accomplished by translating the heaters relative to the array or by translating the array relative to the heaters.

When fluorescent detection is desired, an optical array 890 may be provided. As shown in FIG. 2, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible. The embodiment for second-stage heaters shown in FIG. 18 provides the heaters on the opposite side of pouch 510 from that shown in FIG. 2. Such orientation is illustrative only and may be determined by spatial constraints within the instrument. Provided that second-stage reaction zone 580 is provided in an optically transparent material, photodetectors and heaters may be on either side of array 581.

As shown, a computer 894 controls valves 899 of compressed air source 895, and thus controls all of the pneumatics of instrument 800. In addition, many of the pneumatic systems in the instrument may be replaced with mechanical actuators, pressure applying means, and the like in other embodiments. Computer 894 also controls heaters 886 and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

Other prior art instruments teach PCR within a sealed flexible container. See, e.g., U.S. Pat. Nos. 6,645,758 and 6,780,617, and U.S. patent application Ser. No. 2014/0038272, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. Still, it is understood that the pouch contents could be removed for further testing.

FIG. 2 shows an illustrative instrument 800 that could be used with pouch 510. Instrument 800 includes a support member 802 that could form a wall of a casing or be mounted within a casing. Instrument 800 may also include a second support member (not shown) that is optionally movable with respect to support member 802, to allow insertion and withdrawal of pouch 510. Illustratively, a lid may cover pouch 510 once pouch 510 has been inserted into instrument 800. In another embodiment, both support members may be fixed, with pouch 510 held into place by other mechanical means or by pneumatic pressure.

In the illustrative example, heaters 886 and 888 are mounted on support member 802. However, it is understood that this arrangement is illustrative only and that other arrangements are possible. Illustrative heaters include Peltiers and other block heaters, resistance heaters, electromagnetic heaters, and thin film heaters, as are known in the art, to thermocycle the contents of blister 864 and second-stage reaction zone 580. Bladder plate 810, with bladders 822, 844, 846, 848, 864, 866, hard seals 838, 843, 852, 853, and seals 871, 872, 873, 874 form bladder assembly 808, which may illustratively be mounted on a moveable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 3.

By thermocycling heaters 886, 888, run time for the PCR portions necessarily needs to be at least as long as the heater takes to get to a suitable temperature at each transition. It is understood that run time could be reduced if the temperature of the heaters do not need to be changed. FIGS. 6-8 show another embodiment for the first-stage PCR amplification. In this illustrative embodiment, blisters 548 and 564 may be replaced with a single blister 549, and the illustrative instrument may be provided with a temperature control element that includes heaters 986 and 987. However, it is understood that one of blisters 548 or 564 may be used and smaller heaters 986, 987 may be used, or that blister 549 may be used by itself in combination with other embodiments that may or may not include components for cell lysis and/or additional amplification. Heaters 986, 987 may be Peltier devices, resistance heaters, induction heaters, electromagnetic heaters, thin film heaters, printed element heaters, positive temperature coefficient heaters, other heaters as are known in the art, or combinations of heater types (e.g., a heater element that includes a Peltier thermoelectric heater/cooler device and a resistive heater). However, unlike heater 886 that is provided to thermocycle between an annealing and a denaturation temperature, in one example, heater 986 may be provided at a suitable denaturation temperature, illustratively 94° C., and heater 987 may be provided at a suitable annealing temperature, illustratively 60° C., although other illustrative denaturation and annealing temperatures may be used, as are known in the art. In some embodiments, it may be desirable to set heater 986 higher than 94° C. and set heater 987 at a temperature lower than 60° C., as fluid may be circulated through control of each of these heaters quickly as the fluid reaches temperature, thereby increasing ramp rate. Such embodiments may be suited for use with enhanced primer and polymerase concentrations. Illustratively, an insulating spacer 983 may be provided between heater 986 and heater 987. Any suitable insulating material may be used, including foam, plastic, rubber, air, vacuum, glass, or any other suitable material illustratively of low conductivity. In embodiments where heaters 986 and 987 are held at a generally constant temperature, run time and energy usage may be substantially reduced.

In the illustrative example, a wiper head 910 comprising a wiper 989 engages top surface 549b of blister 549. When fluid is moved into blister 549, wiper 989 is moved so that body 913 of wiper 989 forces blister 549 into contact with heaters 986, 987, so that a portion of blister 549 is in contact with each of the heaters, to permit thermal transfer from each of the heaters to a portion of blister 549. One or more blades 949 may then be used to move the sample 572 from one area of blister 549 to another area of blister 549.

Figure 8A:
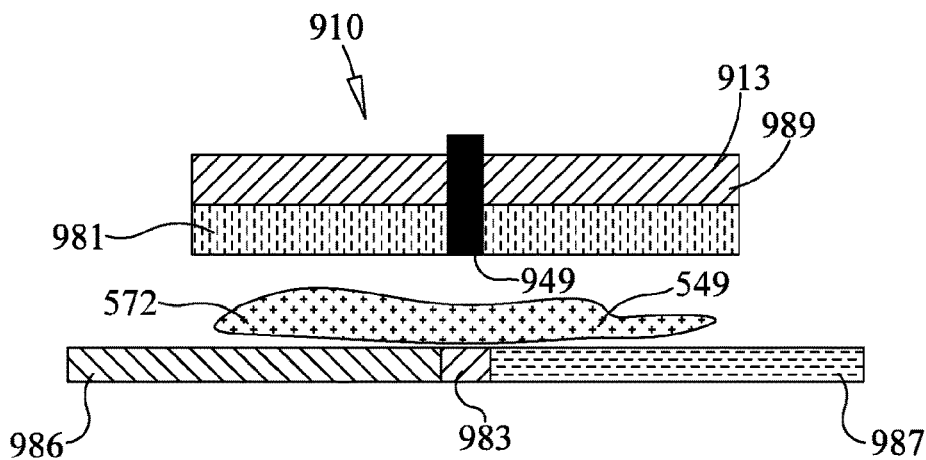
FIGS. 8A-8D show a cross-sectional view of FIG. 7 and also illustrate how a wiper may contact a fluid-filled blister, according to one embodiment of the present disclosure.
Figure 8B:
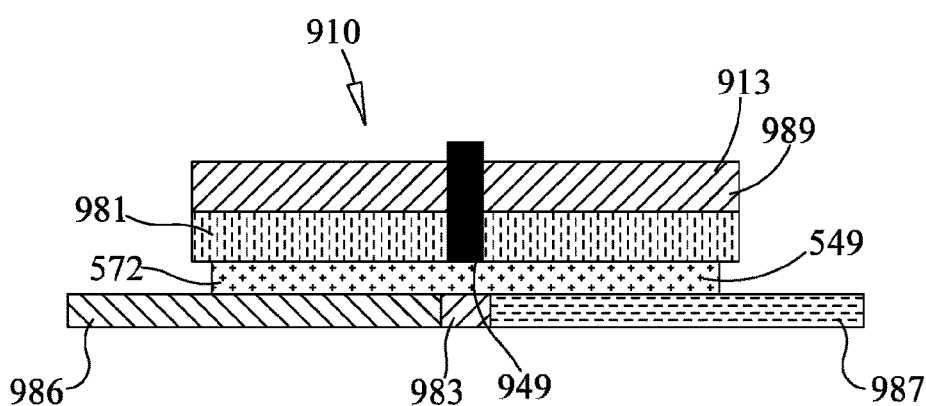

Often when a fluid enters a compartment, the fluid may remain near the entry to that compartment or the contents of a compartment may not be fully mixed. This is schematically illustrated in FIG. 8A where the illustrated blister 549 has adopted an irregular shape and may not be in good contact with the heaters 986 and 987. Depending on the volume of the blister 549, the volume of sample 572 added, the contents of the sample, etc., the fluid 572 may be irregularly shaped with the bulk of the fluid collected near where the sample is injected into the blister. This may be particularly true where the compartment is expandable and is partially or fully collapsed prior to the addition of the fluid, or in other situations when the fluid may be less than sufficient to fill the compartment completely. One can imagine an embodiment wherein sample 572 enters blister 549 through channel 552a and remains near channel 552a so that engagement of blade 949 traps most or all of sample 572 in section 549c. Accordingly, it may be desirable to spread the fluid across the compartment prior to engagement of a blade. Thus, as illustrated in FIG. 8B, wiper head 910 may lowered until it contacts the blister 549 to spread sample 572 across blister 549 to evenly distribute the fluid 572 in the blister 549, to cause the blister 549 to adopt a regular shape, and to press the blister 549 into good, consistent contact with the heaters 986 and 987.

In one embodiment, the wiper head 910 may be provided with a pressure member 981 that places pressure on blister 549 and spreads sample 572 across blister 549. Illustratively, use of member 981 has several benefits. One is that more of sample 572 may be spread across heaters 986, 987 in a thinner layer, thus increasing the surface area to volume ratio, which should improve heat transfer to and from sample 572. Likewise, since the fluid is being rapidly thermocycled—i.e., the liquid of sample 572 is rapidly being raised and lowered in temperature by heaters 986 and 987, spreading the liquid into a thin layer in blister 549 may decrease the dwell time at any given temperature and allow more of the sample to hit the target temperature more quickly. Also, depending on the shape of wiper 989, as discussed below, pressure from member 981 onto blister 549 spreads sample 572 so that engagement of blade 949 of wiper 989 divides the sample 572 in blister 549 into relatively even or proportional volumes. Pressure from member 981 prior to engagement of blade 949 would force some of sample 572 into each of the sections of blister 549.

In one embodiment, member 981 is compressible or semi-compressible (e.g., formed of or comprising a compressible or semi-compressible material). Such materials include compressible or semi-compressible foams, plastics, or rubbers, or may be a more solid material but have a spring-loaded, elastomeric, or other biasing member or force between member 981 and wiper body 913, such that when sample 572 is moved into blister 549, sample 572 is spread across blister 549 but member 981 compresses appropriately to permit sufficient space for sample 572. Other compressible or semi-compressible materials may be used as are known in the art. Alternatively, member 981 may be substantially rigid and set to a position such as to provide only a sufficient space between member 981 and heaters 986, 987 to force the sample 572 to spread across blister 549.

Figure 8C:
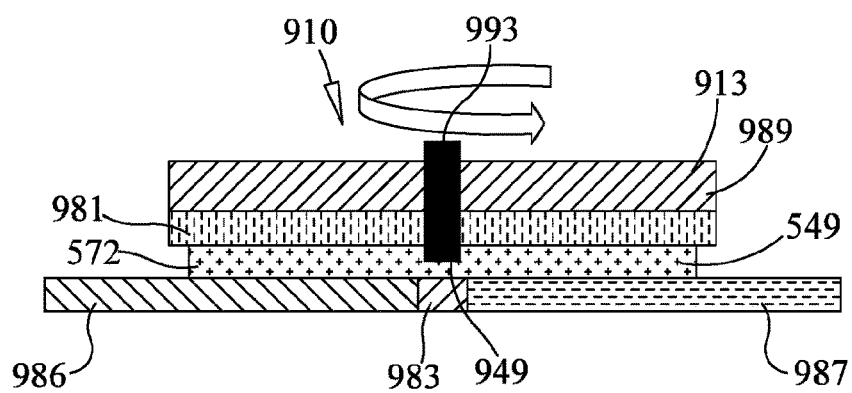
Figure 8D:
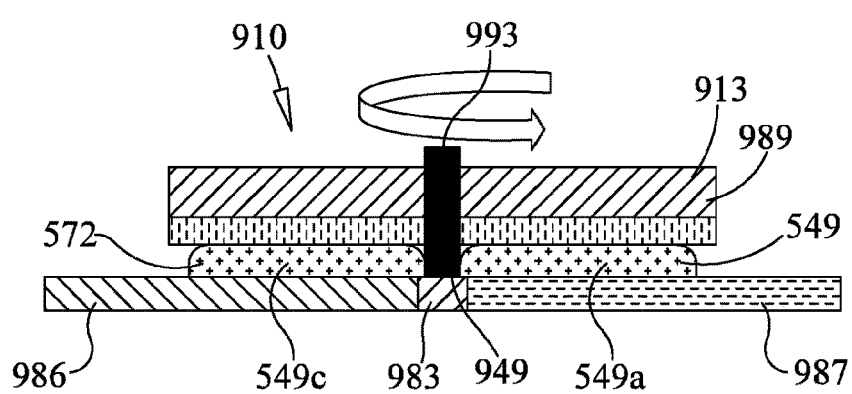

In the illustrative embodiment, wiper 989 has an x-shaped blade 949 that extends through member 981 and divides wiper 989 into four sections 945, 946, 947, 948, as illustrated in FIG. 6. As illustrated in FIGS. 8C and 8D, the wiper 989 and the blade 949 may contact the blister in at least two modes. As illustrated in FIG. 8C, the wiper 989 may be lowered until member 981 is compressed partially and the blade 949 impinges partially on the blister 549. If the wiper head 910 is rotated in the mode of FIG. 8C, the action of the blade 949 can be used to provide a stirring action to thoroughly mix the contents 572 of the blister 549.

If the wiper head is lowered further, as illustrated in FIG. 8D, such that member 981 is further compressed and the blade 949 fully impinges in the blister 549, then the blade may divide the blister into discrete sections. For example, with an x-shaped blade 949, as illustrated in FIG. 7, the blade 949 may contact blister 549 with enough pressure such that blade 949 divides blister 549 into corresponding four sections, 549a, 549b. 549c, 549d. Rotation of wiper 989 around axis 993 forces fluid within blister 549 into a circular motion around blister 549. In one embodiment, blade 949 allows portions of the fluid to be heated by each of the heaters 986 and 987 simultaneously, and moves portions of fluid from temperature control of one heater while permitting other portions of fluid to be under control of the other heater. Member 981 compresses the contents of blister 549. Thus, in addition to spreading out the fluid 572 in the blister 549 and improving contact between the blister 549 and the heaters 986 and 987, member 981 may also plunge the contents of blister 549 to another blister. For example, after first-stage thermal cycling is complete, an exit channel may be opened, which opens a path for fluid to flow out of the blister as member 981 returns to its original shape. In one embodiment, fluid may only flow out of the quadrant of the blister that is fluidly connected with the channel. Wiper 989 may be rotated so that each quadrant is connected with the exit channel in turn.

Illustratively, blade 949 may be a rubber or elastomeric material, or a non-stick material such as Teflon or Delrin having enough stiffness to divide blister 549 into sections and to move fluid within blister 549, but not puncture or tear blister 549, although it is understood that such materials are illustrative only and that other materials may be used, as are known in the art. Blade 949 alternatively may be replaced by rollers or other configurations to allow movement of fluid within blister 549. Wiper head 910, including wiper 989 and blade 949, may be moved into position and rotated by any motor, cam, crank, gear mechanism, hydraulics, pneumatics, or other means, as are known in the art. Such movement may be continuous or wiper 989 and blade 949 may be moved step-wise with pauses, illustratively 0.1 seconds to a minute or more, thus holding portions of the sample in control of each of the heaters 986, 987 before being moved to its next position and holding different portions of the sample in control of each of the heaters 986, 987. The motion of wiper 989 may be circular, in a clockwise or counter-clockwise motion, or may reverse directions, alternating between clockwise and counter-clockwise. It is understood that wiper body 913 and blade 949 may be a single fixed unit and move as a single fixed unit, or body 913 may be moved into and out of contact with blister 549 independently of movement of blade 949. It is also understood that the circular shape of blister 549 and rotational motion is illustrative only, and that other sample vessel shapes are possible, as are non-rotational movement of the blade or rollers, such as linear, curvilinear, and semi-circular motions. Additional features of a specific embodiment of a wiper are described with reference to FIGS. 11A-B.

As discussed above, wiper 989 is provided with an x-shaped blade 949, thereby partitioning wiper into four segments 945, 946, 947, 948, as best seen in FIG. 6, and similarly dividing blister 549 into four segments 549a, 549b, 549c, and 549d, as best seen in FIG. 7. However, it is understood that this is illustrative only, and that any shape of blade 949 may be used, including a single linear blade illustratively substantially corresponding to a diameter of blister 549, a single or multiple non-linear blade including an s-shaped blade or a spiral blade, a single blade corresponding to a radius of blister 549 (similar to a clock hand), and multiple blades that divide blister 549 into multiple segments. It is understood that blades that divide blister 549 into multiple similar segments likely provide more controlled heating between different segments where entire segments will be at the annealing and denaturation temperatures at one time, whereas s-shaped, spiral, and radial blades may generate multiple vortexes, eddies, and varied mixing patterns, to move the sample across the thermal surface created by heaters 986, 987. It is also understood that less blade material allows for more of the sample to be in close contact with the heaters, while more blade material better controls fluid movement. Whatever the blade pattern, it is understood that portions of the fluid in blister 549 will be at the annealing temperature, while other portions will be at the denaturation temperature, and yet other portions may be in transition between the temperatures, all within a single sample container. The choice of shape for blade 949 may depend on size and thickness of the blister and size of the heaters, and the desirability of using wiper 989 for expelling material from blister 549 once first-stage thermal cycling has been completed.

In the illustrative embodiment, heaters 986, 987 provide a flat surface against which blister 549 may be pressed. However, it is understood that this is illustrative only, and heaters 986, 987 may provide a textured surface to aid in mixing for sample uniformity.

In the illustrative embodiment, heaters 986 and 987 are each provided at fixed temperatures, illustratively 94° C. and 60° C. respectively. However, it may be desirable to adjust the temperature of heaters 986 and 987 during use, in some embodiments. For example, it may be desirable to increase the temperature of one or both heaters when the sample is first introduced to blister 549, to compensate for a cooler temperature of the fluid as it enters blister 549. In another example applicable to the following discussion, it may be desirable to "overdrive" the heaters to allow the heaters to achieve the target temperature of the fluid in the blister more rapidly. For instance, if the target temperatures for thermocycling are 94° and 60°, then the heaters may be set above the high temperature (e.g., in a range of 95-110° C.) and below the lower temperature (e.g., in a range of 59-50° C. to more rapidly heat and cool the fluid in the sample. Additionally, while two heaters are shown, any number of heaters may be used. One illustrative example uses three heaters, with one set at a denaturation temperature, one set at an annealing temperature, and the third set at an elongation temperature. In another illustrative example, a first heater may be larger than a second heater, so that the sample stays at the first temperature for a longer portion of the cycle. Moreover, it is understood that blister 549 and its contents may remain stationary, and heaters 986, 987 may be rotated or translated laterally.

Illustratively, fluid may enter blister 549 through channel 552a from a nucleic acid extraction zone, illustratively similar to blister 546 of the pouch of FIG. 1, and channel 552a may then be closed. Member 981 then presses on blister 549, promoting contact of blister 549 with heaters 986 and 987, and then blade 949 is moved toward heaters 986, 987 and divides blister 549 into segments 549a, 549b, 549c, and 549d. As wiper 989 is rotated, sample in each of the four segments 549a, 549b, 549c, and 549d is moved from contact with heater 986 to contact with heater 987, and back again. The amount of time needed to heat and cool the sample in each of the segments is dependent on a number of factors, including thickness of film on blister 549, thickness of the fluid layer within blister 549, mixing of the sample within blister 549, and amount of contact with the heaters. However, it is understood that one full revolution of wiper 989 generally corresponds to one cycle of PCR in this illustrative embodiment.

With certain assays, target nucleic acids may be present in very small quantities. Accordingly, it may be necessary to start with a substantial volume of sample in blister 549 in order to have enough copies of the target nucleic acid present. Illustratively, blister 549 contains 10 μL to 1 mL of fluid, illustratively between 25 μL and 200 μL, but other volumes may be appropriate depending on the configuration of the system. Optionally, after a few cycles, illustratively after 2 to 10 cycles, when the amount of target nucleic acid has been somewhat amplified, channel 552a (or another channel) may be opened, and body 913 may be moved closer to heaters 986, 987 to squeeze blister 549, thereby expelling a portion of the fluid from blister 549 through channel 552a. Channel 552a may then be closed. At least a portion of the sample may also be expelled by motion of blade 949, particularly if blade 949 may be shaped to force at least a portion of the sample outward, such as with an s-shaped blade. Illustratively, 5%, 10%, 15%, 20%, 25%, 30%, 35%, 40%, 45% or 50% or more of the sample volume may be removed, or any amount in between. If a compressible or semi-compressible member 981 is used, it is understood that the motion of body 913 toward heaters 986, 987 may need to be adjusted to compensate for this compression to achieve the appropriate reduction in sample volume. Since the volume of fluid in blister 549 is now reduced, less time may be needed in contact with each of the heaters 986, 987 to bring the fluid to the appropriate temperature and the speed of the wiper 989 rotation may be increased, thereby reducing cycle times. Illustratively, when the sample volume is reduced by 50%, cycling time may be reduced by 25 to 50%. In one example, the sample volume was reduced by 50% and the cycling time was reduced by about 35%. After a few more cycles, an additional reduction in volume, with corresponding reduction in cycle time may take place. Multiple reductions, illustratively one to five reductions may take place. It is understood that efficient reactions essentially double the target sequence each cycle. Thus, in some embodiments, losing some sample volume in early cycles to gain faster run time may be a good trade-off.

Figure 9A:
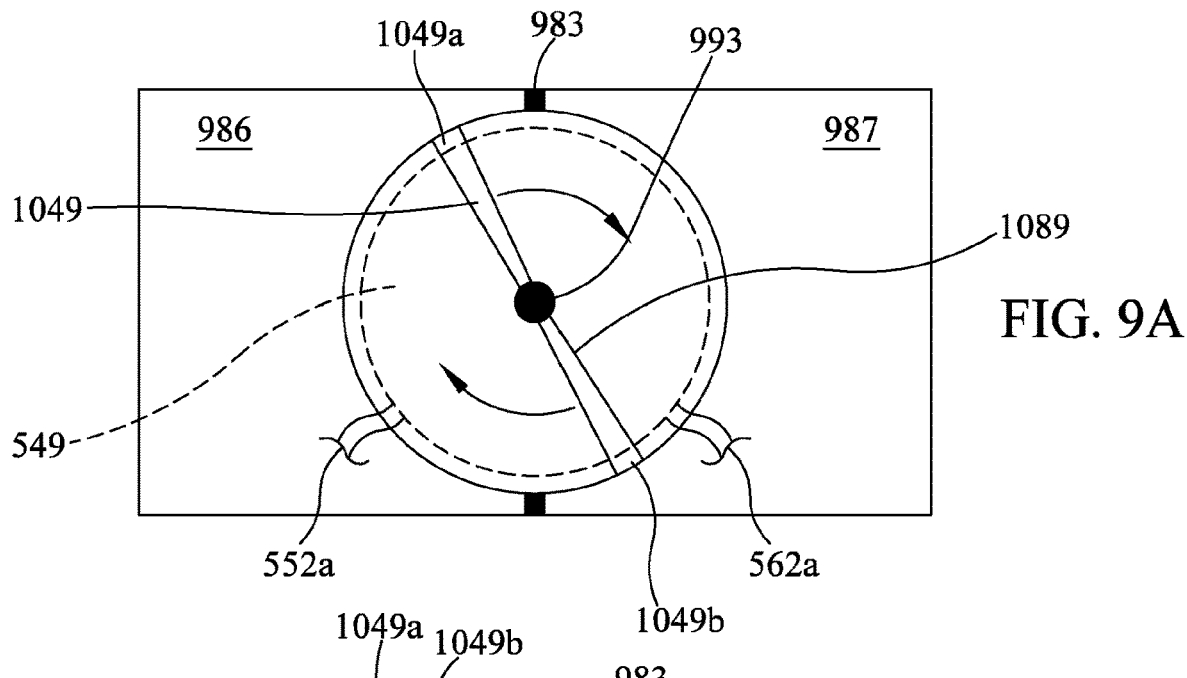
FIGS. 9A-9C are similar to FIG. 7 but showing an alternate embodiment of a wiper.
Figure 9B:
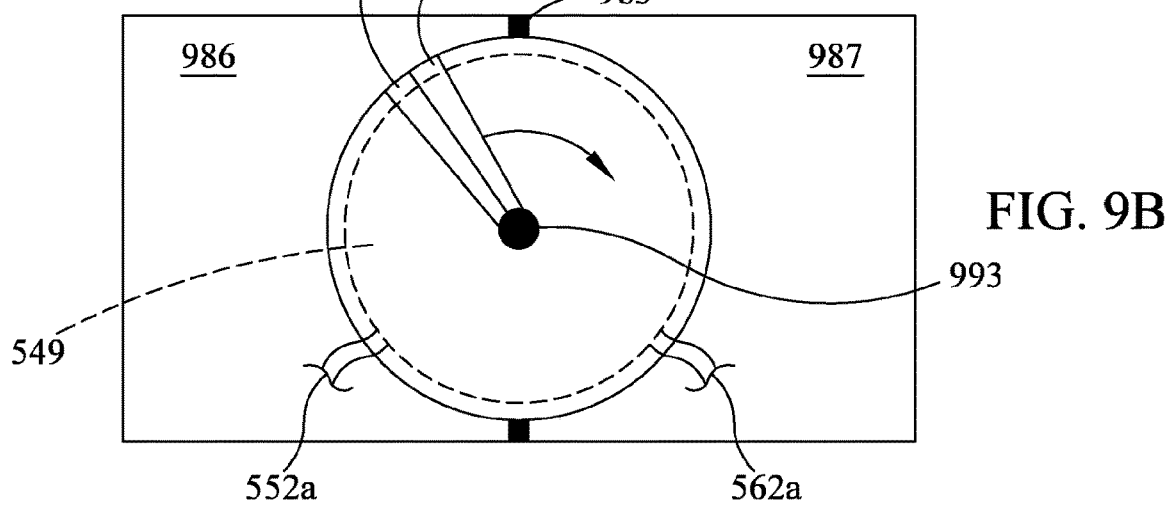
Figure 9C:
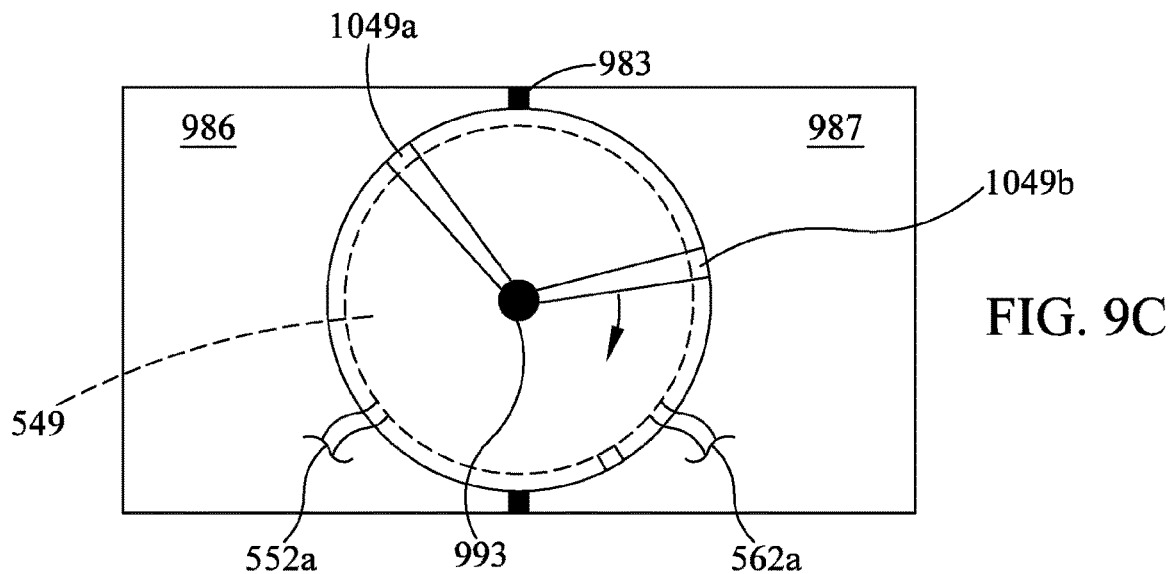

FIGS. 9a-9c show another embodiment that may be employed (e.g. to reduce the volume of sample 572 or to expel fluid from blister 549). In this embodiment, wiper 1089 is provided with blade 1049 that has two arms, 1049a and 1049b. As shown in FIG. 9a, the two arms 1049a and 1049b are provided in a linear arrangement, thus dividing blister 549 into two substantially equal halves. As shown by the arrows, blade 1049 may be moved in a clockwise direction, although, as discussed above, other motions are possible. However, in this embodiment arms 1049a and 1049b may be moved independently. To reduce the volume, arm 1049b may be rotated toward arm 1049a to reach a desired location. This movement may be made with or without moving body 913 away from heaters 986, 987. If wiper 1089 is retracted from heaters 986, 987 during this movement, body 913 may be moved back toward heaters 986, 987 after the movement is complete. Once arms 1049a and 1049b are in a desired position, as best shown in FIG. 9b, channel 552a may be opened, and blades 1049a and 1049b may be moved apart from each other, illustratively by moving blade 1049b in the direction shown by the arrow in FIG. 9b to get to the position in FIG. 9c. While about 100 degrees of rotation is shown in FIG. 9c, this is illustrative only, and the amount of rotation may be adjusted to achieve the appropriate reduction in volume or emptying of the blister. It is understood that one or both of arms 1049a and 1049b may be moved to achieve this reduction in volume.

Channel 552a may then be sealed, arms 1049a and 1049b may be moved back to their linear arrangement, and thermocycling may continue.

It is understood that reductions in volume and reductions in cycle time may be used with any of the embodiments disclosed herein or with other embodiments using a wide variety of sample vessels and heating configurations. It is also understood that this method of reducing volume and decreasing cycle time may be combined with the introduction of fresh PCR components. Such may be useful when a combined RT-PCR reaction is desired or where such addition may include primers for nested amplification or for use with universal primers.

Once thermal cycling is complete, channel 562a may be opened. Illustratively, particularly when blade 949 is curved the direction of wiper 989 may be used to pump fluid from blister 549 into channel 562a. Alternatively, blister 549 may be a stand-alone container for thermocycling a sample, such that blister 549 is sealed after receiving a PCR reaction. Blister 549 may be used for any of a variety of sample types that require thermocycling.

Figure 10:
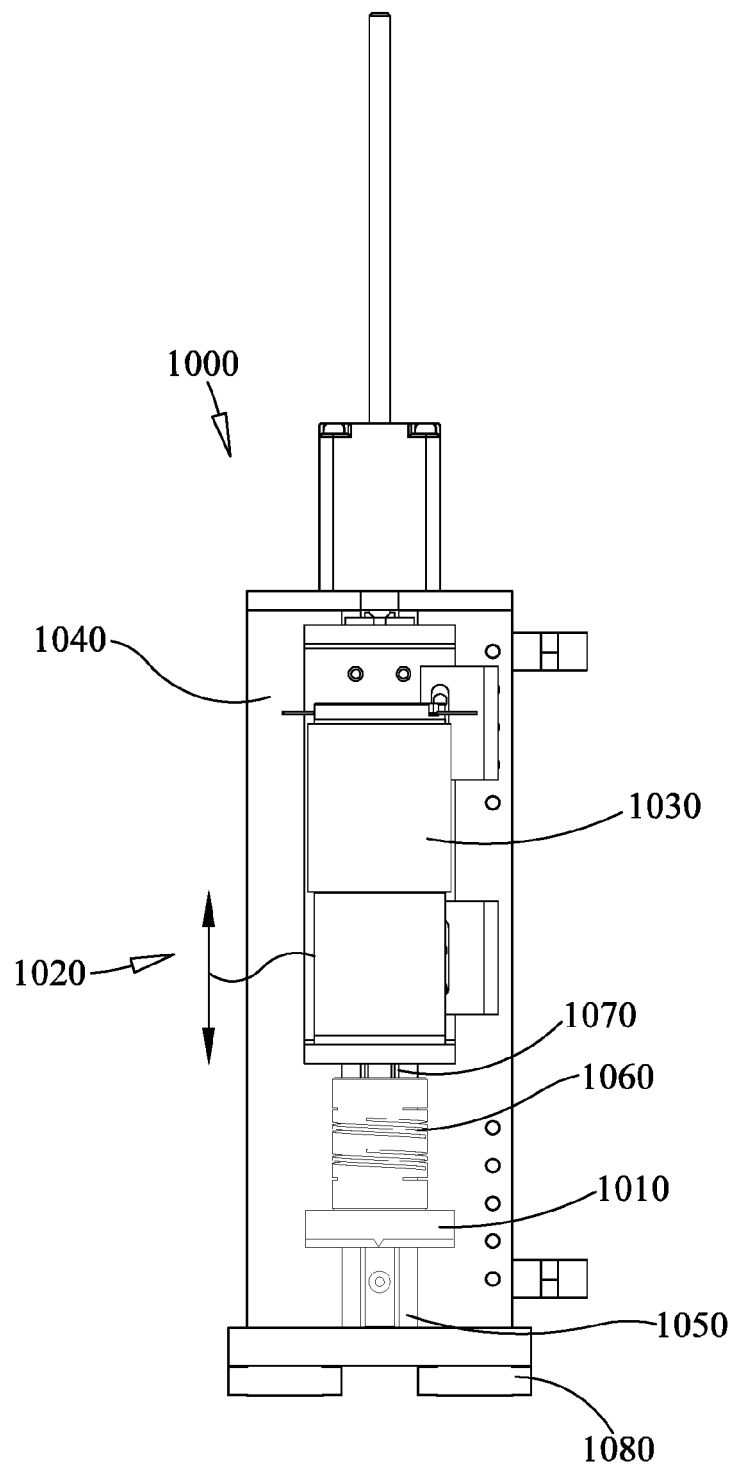
FIG. 10 illustrates an embodiment of a wiper system that can be used with the thermocycling embodiments illustrated in FIGS. 6-9C.

FIG. 10 illustrates an embodiment of a wiper system 1000 that can be used with the heater devices illustrated in FIGS. 6-9C for, for example, moving the contents of a blister between two heat zones for thermocycling. The wiper system 1000 includes a wiper head 1010 that may be attached to a rotary motor 1030 via shaft 1070 and connector 1060. Rotary motor 1030 may be coupled to support 1040; motor 1030 and wiper head 1010 can be raised and lowered as indicated by arrows 1020 on support 1040 on, for example, rail 1050. Wiper system 1000 may be mounted above heaters 986, 987 (shown in FIGS. 6-7), with space for a sample blister to be inserted therebetween.

In one embodiment, wiper system 1000 may be mounted in an instrument such that a blister in a sample vessel may be placed below base 1080. In one example, the head 1010 and motor 1030 assembly may be lowered past the base 1080 to contact a fluid-filled blister. Motor 1030 can be rotated so that the wiper head 1010 can move the contents of the fluid-filled blister. If the fluid-filled blister is in contact with a heater device (e.g., heaters 986 and 987) having separate heated zones (e.g., a zone at 94° C. and a separate zone at 60° C.), the motor 1030 and wiper head 1010 can be lowered so that the blade(s) of the wiper head 1010 divide the blister into separate, discrete volumes and used to move the contents of the fluid-filled blister for thermal cycling for PCR, as described above in reference to FIGS. 6-9C.

In addition to the thermal cycling devices described above, the heater and mixer systems described herein can also be used for automated sample preparation in an enclosed pouch. For instance, as will be described in greater detail below, heating a blister like 549 with one or both of heaters 986 and 987 while blending the contents of a sample preparation blister with mixer system 1000 can be used to lyse cells (e.g., bacterial and mammalian cells) and release the nucleic acids therein. Alternatively or in addition, a blister may include a chaotropic agent, a detergent, and/or lysis beads (see, e.g., lysis blister 522 of pouch 510 of FIG. 1). Likewise, heating and cooling with thermoelectric cooling devices (i.e., Peltier devices) and mixing can be used to increase the efficiency of other sample preparation processes. For example, nucleic acids bind more efficiently to magnetic beads (e.g., magnetic beads 533 of FIG. 1) at lower temperatures (e.g., ~0-10° C.) and are eluted more efficiently from the magnetic beads at higher temperatures (e.g., ~60-90° C.). Thus, lysing may illustratively occur when blister 549 is in contact with heater/cooler 986, while magnetic bead binding may illustratively occur when blister 549 is in contact with heater/cooler 987, and these heaters may move laterally, as discussed below with respect to FIGS. 12-13.

Figure 11B:
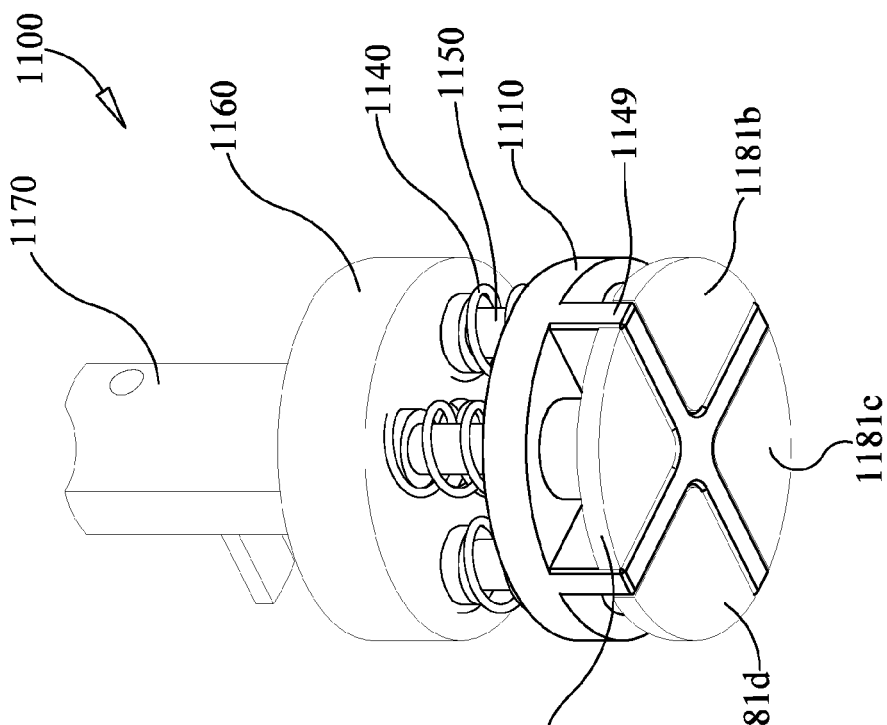
FIGS. 11A and 11B illustrate a wiper head according to one embodiment of the present disclosure.
Figure 11A:
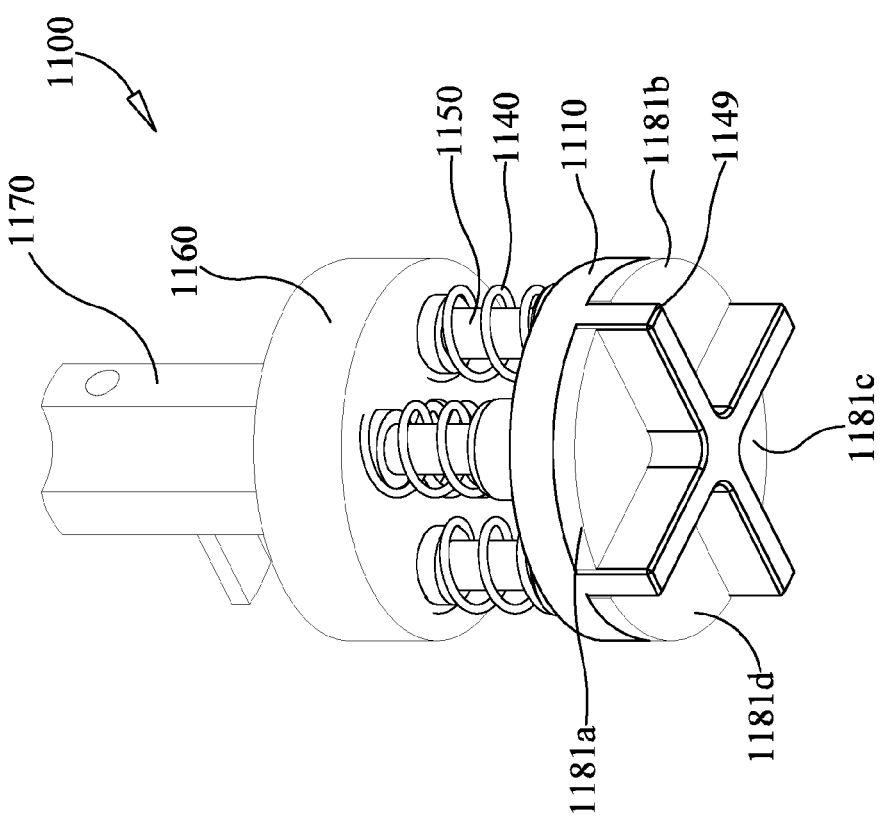

Referring now to FIGS. 11A and 11B, an embodiment of a wiper head 1100 that may be included on the wiper system of FIG. 10 is illustrated. The wiper head 1100 may, for instance, be attached to the shaft 1070 of the wiper system 1000 of FIG. 10 via the chuck 1170 that is at the distal end of the wiper head. The proximal end of the wiper head 1100 includes a wiper body 1110 with wiper blades 1149. The wiper head 1100 may also include spring members 1140, and a pins, screws, or the like 1150 that couple the upper portion of an upper body 1160 to the wiper body 1110. In one embodiment, the wiper head may be configured such that the spring members 1140 can regulate the amount pressure that the wiper head 1110 and wiper blade 1149 can exert on a fluid-filled blister.

The illustrated wiper body 1110 may also illustratively include pressure members 1181a-1181d that are disposed in the quadrants between the wiper blades 1149. In one embodiment, the pressure members 1181a-1181d may work together to function like pressure member 981 described in relation to FIGS. 8A-8D. That is, pressure members 1181a-1181d may be positioned relative to the wiper blades 1149 such that the pressure members 1181a-1181d can apply a consistent, predictable pressure when the wiper blades 1149 are brought into contact with a fluid-filled blister. However, in reference to FIG. 11B, another embodiment is illustrated where the pressure members 1181a-1181d may be deployed, moved, or lowered relative to the wiper blades 1149 to apply pressure to a fluid filled blister. In the illustrated example, the pressure members 1181a-1181d may be deployed by lowering the wiper head 1100 until the blades 1149 and the pressure members 1181a-1181d present a substantially flat surface against the fluid filled blister. In one embodiment, the pressure members 1181a-1181d may be deployed by lowering the wiper head 1100 past the point that the wiper blades 1149 contact the blister; continuing to lower the wiper head 1100 can compress the wiper blades 1149 up and/or press the pressure members 1181a-1181d down. The spring members 1140 may be configured to regulate the amount of pressure on the blades 1149 and the plunger head 1110 is needed to deploy the pressure members. Lowering the wiper head 1100 down until the wiper blades and the pressure members form a substantially planar surface may, for instance, be used to spread liquid uniformly within a blister or to plunge liquid from one blister to another. In another embodiment (not shown), the pressure members may be deployed to an intermediate position by a similar mechanism to, for example, exert pressure on a fluid-filled blister to improve contact between the blister and an underlying heater. In one or more embodiments, the wiper head 1100 may include multiple spring member types associated with the wiper blade(s) 1149 and/or the pressure members 1181a-1181d to modulate or regulate the amount of pressure that the blades 1149 and the pressure members 1181a-1181d can apply to a fluid-filled blister.

Figure 12A:
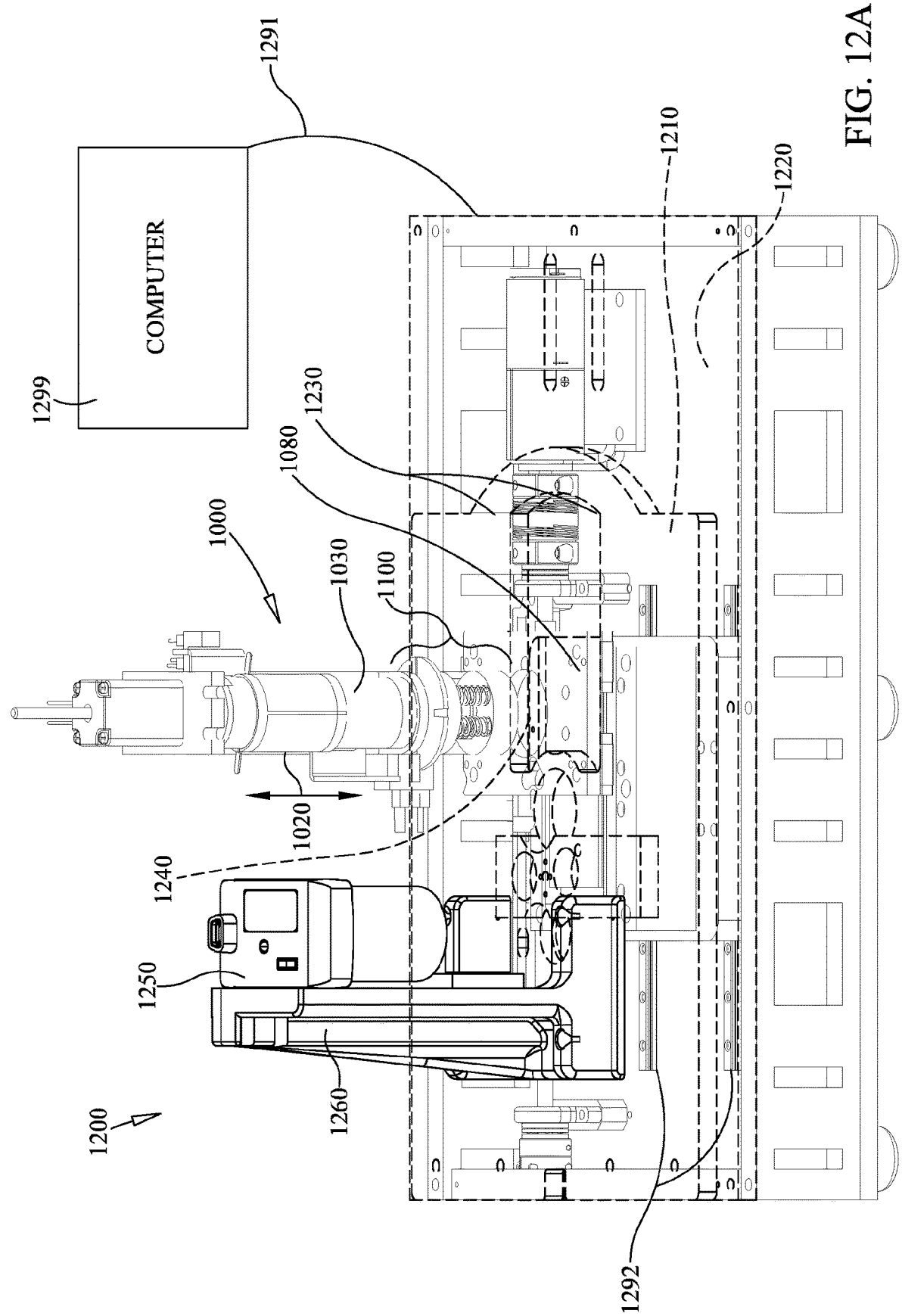
FIGS. 12A and 12B illustrate a thermocycling instrument that incorporates a wiper system and a heater that includes at least two temperature zones, according to one embodiment of the present disclosure.
Figure 12B:
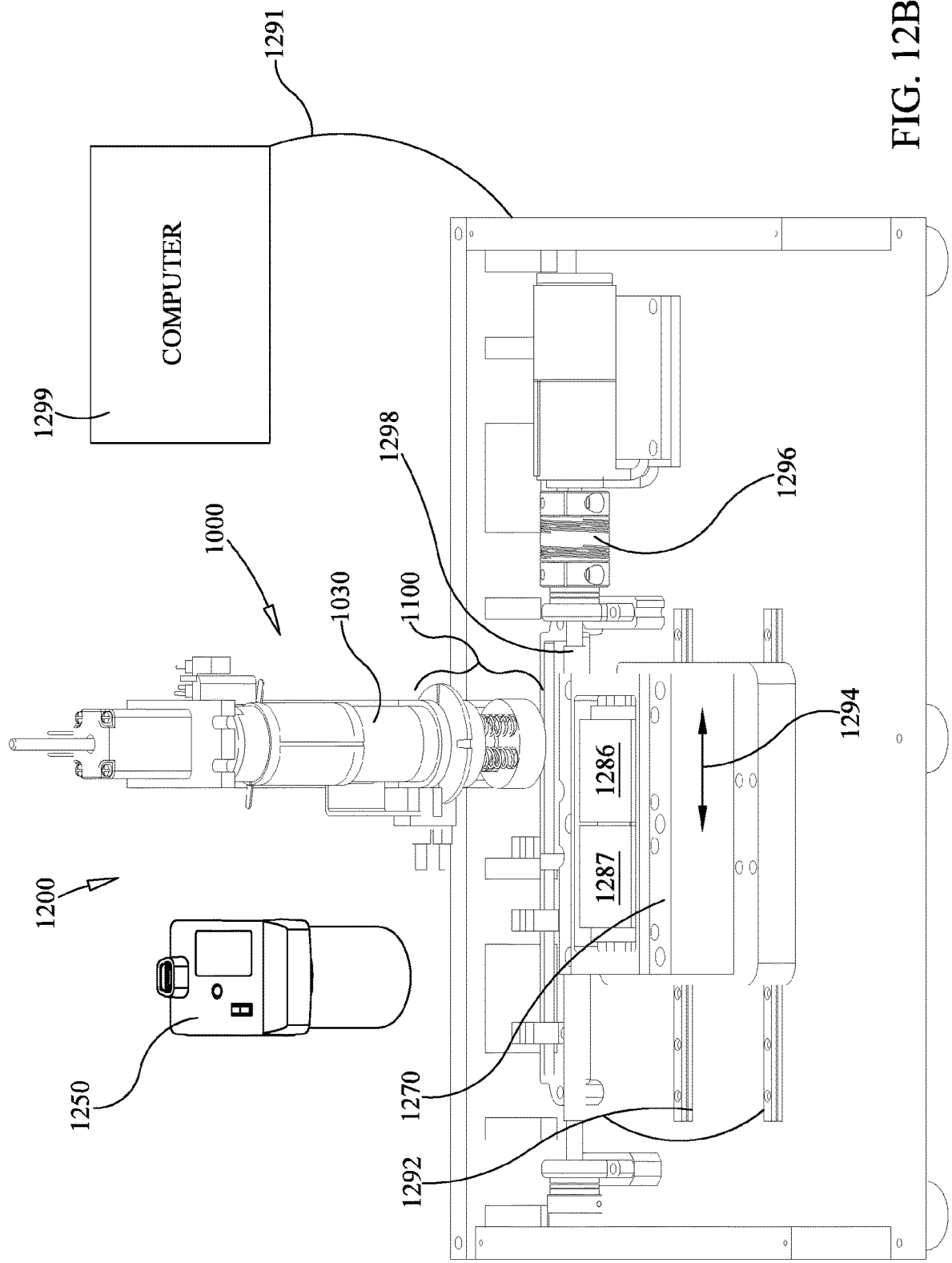

Referring now to FIGS. 12A and 12B, an instrument 1200 is illustrated that includes features of the wiper system 1000 discussed in reference to FIG. 10, the wiper head 1100 discussed in reference to FIGS. 11A and 11B, and many of the features of the heaters 986 and 987 of FIG. 6. In the illustrative example, the instrument 1200 includes a hinged cover 1210 and a chassis cover 1220. The hinged cover 1210 can be opened for insertion of a flexible pouch for self-contained PCR into the instrument between the hinged cover 1210 and the chassis cover 1220. The chassis cover 1220 lies over the internal components of the instrument 1200 and may define a receptacle for positioning a flexible pouch such as the one illustrated in FIG. 14A in the instrument, wherein the receptacle may be coextensive with a portion of the pouch. As will be explained in greater detail below, the receptacle may be configured to receive the flexible pouch in the instrument and align the flexible pouch so that various components of the instrument can interact with the flexible pouch. Likewise, the receptacle may include openings and the like so that the internal components of the instrument can contact the flexible container. Likewise, the hinged cover 1210 may include openings and the like so that external components of the instrument can interact with the flexible container. Above the covers 1210 and 1220, the instrument 1200 includes the wiper system 1000, which includes the drive motor 1030 and the wiper head that were previously described, and camera/fluorimeter 1250 and a mount 1260 for collection of fluorimetric data. As in the previous examples, the wiper system can be moved up and down as indicated by arrows 1020 through a hole 1240 in the base 1080 and through one or more holes in the hinged cover 1210 in order to contact the pouch.

In addition, in the illustrated embodiment, the wiper system may be translated side-to-side, illustratively on rails 1230, so that the wiper system 1000 can contact different regions of a pouch inserted into the instrument 1200. In one embodiment, the wiper system 1000 may be translated so that the wiper 1100 can interact with different portions of the pouch. For instance, as will be explained in greater detail below, the wiper system 1000 may be used for in-pouch sample preparation and first-stage PCR steps. In an alternative embodiment, the wiper system 1000 may be held stationary and the pouch may be moved so that the wiper can contact different portions of the pouch. It is understood, however, that this arrangement is illustrative, and other arrangements of moving and aligning wipers, heaters, and sample containers are contemplated. It is understood that any combination of wipers, heaters, and pouches may be placed on movable elements and that when translation of wipers, heaters, pouches, and the like is discussed, such movement may be replaced with opposite translation of the wiper, heater, or pouch, working in concert with that element, in any embodiment where such opposite translation is consistent with the arrangement of other elements. In some embodiments, rotary motion of the pouch and other instrument elements is also contemplated.

Referring now specifically to FIG. 12B, the covers 1210 and 1220 are removed so that the interior of the instrument 1200 can be seen more clearly. The interior of the instrument 1200 illustratively includes a heater assembly 1270 that can be translated back and forth by a translator as shown by arrow 1294, for example, on rails 1292. The heater assembly 1270 includes a first heater element 1286 and a second heater element 1287. In the illustrated embodiment, the heater assembly may be mechanically coupled to a translator that illustratively includes a drive motor 1296 and drive member (e.g., a threaded screw) 1298. Heater assembly 1270 may be translated back and forth, for example, on rails 1292 so that the heaters 1286 and 1287 can interact with different regions of a pouch installed in the instrument. However, it is understood that a motor and rails are illustrative only, and that other linear and non-linear translators may be used. As was discussed in detail above in reference to FIGS. 6-9C, the heater assembly may be positioned so that portions of a blister (e.g., a first-stage PCR blister) can be under temperature control of first heater element 1286 and a second heater element 1287 at the same time, similar to that shown in FIGS. 6-8. Likewise, an entire blister may be controlled by one heater at a time, and the blister (e.g., a first-stage PCR blister or a second-stage PCR blister) can be thermocycled by moving the heater assembly 1270 back and forth with the translator so that a selected blister is repeatedly under temperature control of the first heater 1286 and then the second heater 1287, etc. One will appreciate that while the illustrated embodiment includes a heater that can move, the same effect(s) can be accomplished by translating the pouch relative to the heaters instead of moving the heater assembly and that this motion can be along linear, arcilinear, or rotational paths, for example.

Heaters 1286 and 1287 may be Peltier devices, resistance heaters, induction heaters, electromagnetic heaters, thin film heaters, printed element heaters, positive temperature coefficient heaters, or other heaters as are known in the art. One will appreciate that heater types may also be combined in a single unit (e.g., a heater unit may include a Peltier device with a resistive heater on the front and/or backside of the Peltier to help with maintaining a fixed temperature and/or to increase the efficiency and speed of heating and cooling). While the term "heater" is used to refer to elements 1286 and 1287, it is understood that other temperature control elements or combinations of elements may be used to adjust the temperature of the sample. Unlike heaters typically included in a PCR device that are provided to thermocycle between an annealing and a denaturation temperature, heaters 1287 and 1286 may be held at a fixed temperature or may be thermocycled in a limited temperature range (e.g., between an annealing temperature and an elongation temperature). For instance, as explained in detail above in reference to FIGS. 6-9C, a sample may be thermocycled by moving the contents of a liquid-filled blister between two static temperature zones. In one example, heater 1287 may be provided at a suitable denaturation temperature, illustratively 94° C., and heater 1286 may be provided at a suitable annealing temperature, illustratively 60° C., although other illustrative denaturation and annealing temperatures may be used, as are known in the art. Also, three or more heaters may be desirable for certain protocols.

In one embodiment, one or both of heaters 1286 and 1287 may include a Peltier element. While heaters 1286 and 1287 may not be thermocycled, it may, for instance, be desirable to include a Peltier element in one or both of heater 1286 and 1287. Unlike a typical resistance heater, Peltier elements can actively cool as well as heat samples. For example, in moving a sample from a denaturation temperature (e.g., 94° C.) to an annealing temperature (e.g., 60° C.), the sample has to be cooled down to the annealing temperature. This will happen by radiation/conduction, but these processes are relatively slow. For rapid thermocycling, it may be preferable, for example, to actively cool the sample with Peltier device with the "cool" side of the Peltier set to 60° C. and the "hot" side, where excess heat may illustratively be pumped and disposed of through a heat sink, may be set to a higher temperature.

Instrument 1200 also includes a computer 1299 that may be configured to control one or more of the wiper 1100, the heaters 1286 and 1287, thermocycling parameters (e.g., movement of the wiper, temperatures of the heaters, alignment of the wiper and heaters with the sample container, etc.), fluid movement in the sample container, etc. Likewise, the computer 1299 may be configured for data acquisition and analysis from the instrument 1200, such as from optical system 1250. Each of these components is connected electrically, illustratively via cable 1291, although other physical or wireless connections are within the scope of this invention. It is understood that computer 1299 may be housed within instrument 1200 or may be external to instrument 1200. Further, computer 1299 may include built-in circuit boards that control some or all of the components, and may also include an external computer, such as a desktop or laptop PC, to receive and display data from the instrument 1200. An interface, illustratively a keyboard interface, may be provided including keys for inputting information and variables such as temperatures, cycle times, etc. Illustratively, a display may also be provided. The display may be an LED, LCD, or other such display, for example.

Figure 13A:
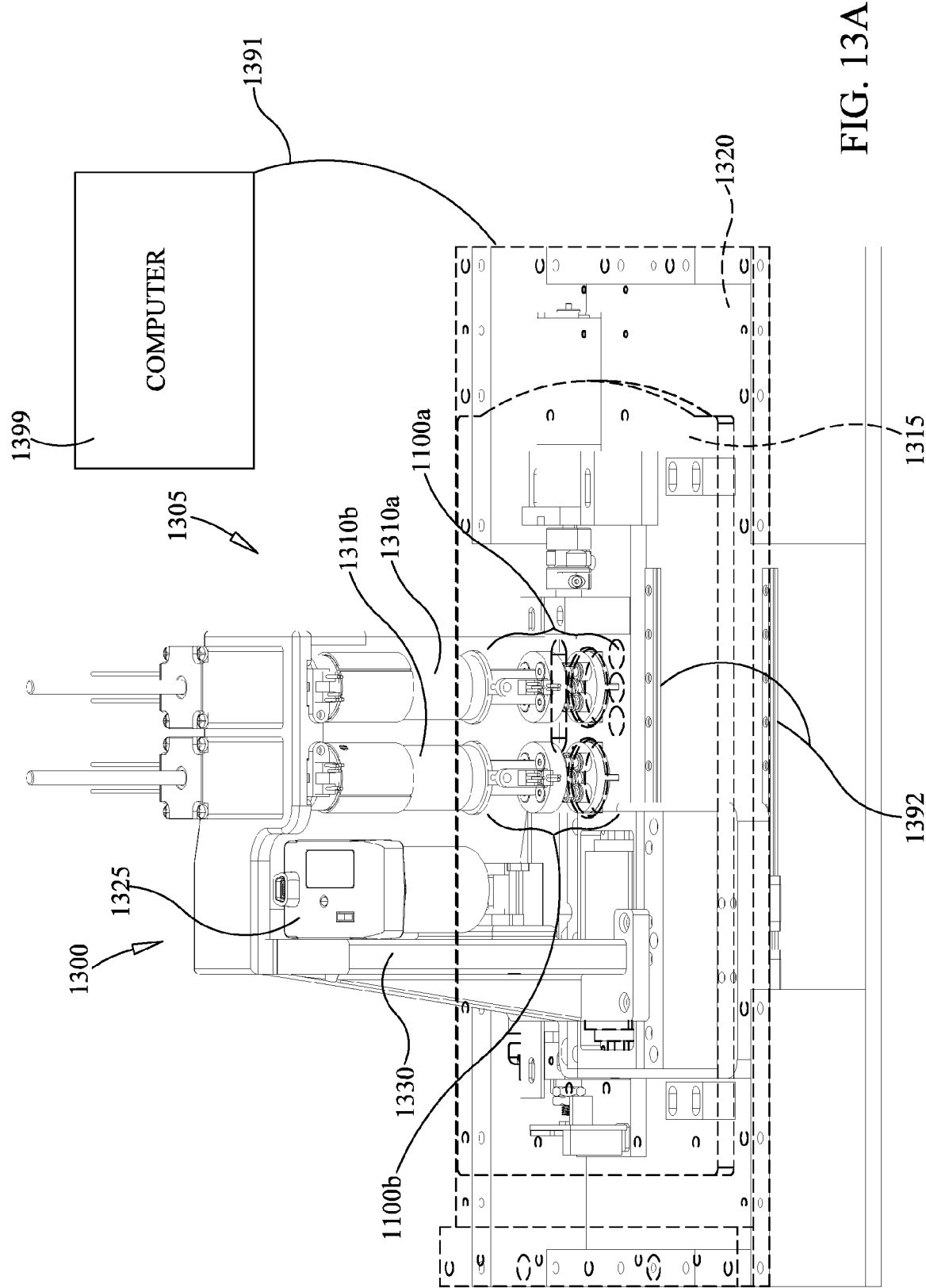
FIGS. 13A and 13B illustrate another thermocycling instrument that incorporates a wiper system and a heater that includes at least two temperature zones, according to one embodiment of the present disclosure.
Figure 13B:
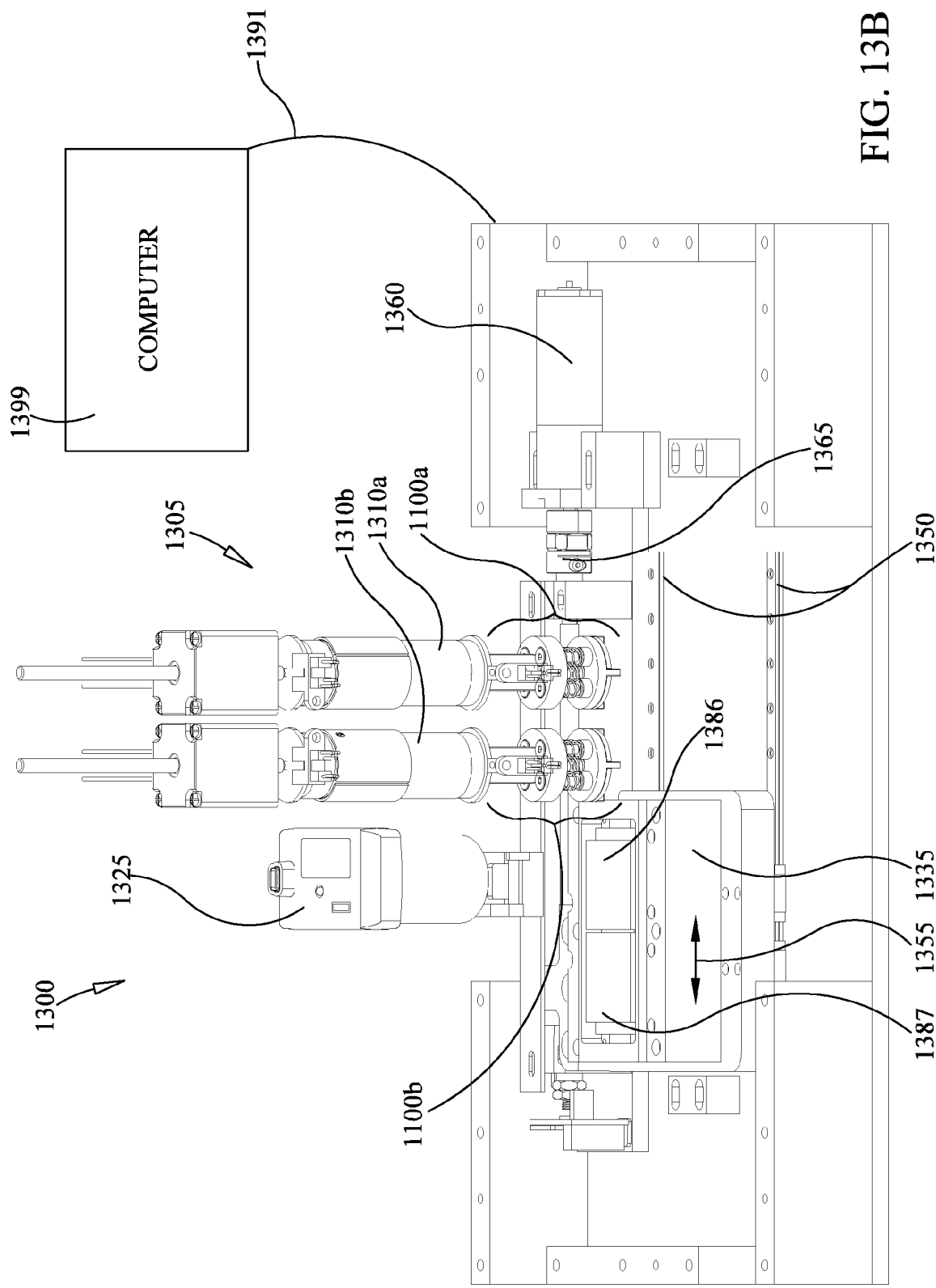

Referring now to FIGS. 13A and 13B, another instrument 1300 is illustrated. Instrument 1300 is similar in many respects to instrument 1200, except instrument 1300 includes a wiper system 1305 with two mixer/wipers. Thus, in one embodiment, there may be no need to translate the wipers horizontally so that the wiper/mixer can interact with different portions of a pouch installed in the instrument 1300.

The instrument 1300 includes the wiper system 1305, which includes first and second wiper motors 1310a and 1310b and first and second wiper heads 1100a and 1100b. The instrument also includes first and second covers 1315 and 1320, a camera 1325 and a camera support 1330. Referring now to FIG. 13B, the instrument 1300 further includes a heater system 1335 that can be translated horizontally 1355 on rails 1350, and first and second heater elements 1386 and 1387. While the term "heater" is used to refer to elements 1386 and 1387, it is understood that other temperature control elements or combinations of elements may be used to adjust the temperature of the sample. The heater system 1335 is mechanically coupled to a drive motor 1360 and a drive member 1365 for translation of the heater system. Illustratively, heater 1386 may be provided at a temperature in a range of about 90-95° C. and heater 1387 may be provided at a temperature in a range of about 55-65° C., although other temperatures and arrangements are possible.

Instrument 1300 also includes a computer 1399 that may be configured to control one or more of the wipers 1100a and 1100b, the heaters 1386 and 1387, thermocycling parameters (e.g., movement of the wiper, temperatures of the heaters, alignment of the wiper and heaters with the sample container, etc.), fluid movement in the sample container, etc. Likewise, the computer 1399 may be configured for data acquisition and analysis from the instrument 1300, such as from optical system 1325. Each of these components is connected electrically, illustratively via cable 1399, although other physical or wireless connections are within the scope of this invention. It is understood that computer 1399 may be housed within instrument 1300 or may be external to instrument 1300. Further, computer 1399 may include built-in circuit boards that control some or all of the components, and may also include an external computer, such as a desktop or laptop PC, to receive and display data from the instrument 1300. An interface, illustratively a keyboard interface, may be provided including keys for inputting information and variables such as temperatures, cycle times, etc. Illustratively, a display may also be provided. The display may be an LED, LCD, or other such display, for example.

Referring now to FIGS. 14A and 14B and FIGS. 15A-15F, an embodiment of a flexible pouch or chemistry card that may be used in instruments 1200 and 1300 is described (FIG. 14A) and a sequence of operations that may be performed by instruments 1200 and 1300 for sample preparation, first-stage PCR, and second-stage PCR are described FIGS. 15A-15F.

The illustrative flexible pouch 1400 of FIG. 14A comprises a substantially planar region 1402 that includes a number of zones or blisters where sample preparation, nucleic acid amplification, and detection can occur. In one embodiment, the pouch 1400 may be fabricated from a number of layers of material (layers of the same material or layers of different types of material) that are sealed together to form the pouch 1400. In FIG. 14B a cutaway illustrating the layers along the line B-B is shown. The illustrative pouch includes a first film layer 1490, a pressure sensitive adhesive layer 1492, a card layer 1494, a second pressure sensitive adhesive layer 1496, and a second film layer 1498. In one illustrative example, the blister areas in the pouch 1400 can be formed by making appropriate cutouts in the card layer 1494. Alternatively, the blister areas of the pouch can be formed by laminating or welding film layers (e.g., film layers 1490 and 1498) together leaving open spaces between the layers that serve as liquid blisters with or without the card layer. One will appreciate that other configurations are possible. It is understood that while the illustrative blister areas are flexible, the card layer 1494 optionally may be less flexible and may be rigid, and still be part of a flexible sample container. Thus, it is understood that a "flexible pouch" need only be flexible in certain zones. Fill channels 1440-1460 and channels connecting the blister areas 1465-1485 may be formed by making appropriate cutouts in the either the first or second pressure sensitive adhesive layers 1492 and 1496, or by providing channels in the card layer 1494. Alternatively or in addition, flow channels between the blister areas can be formed by adding another film layer above film layer 1490 or below film layer 1498 and welding the layers together, leaving open blister areas and channels between the layers.

While other materials may be used, illustratively, the film layers of pouch 1400 may be formed from a flexible plastic film or other flexible material similar to the pouch 510 described in FIG. 1. For instance, pouch 1400 may be fabricated from materials such as, but not limited to, such as polyester, polyethylene terephthalate (PET), polycarbonate, polypropylene, polymethylmethacrylate, combinations, mixtures, and laminated layers thereof that can be made by any process known in the art, including extrusion, plasma deposition, and lamination. Similar materials (e.g., polycarbonate) may be used for the card layer 1494. Other materials, including metal foils or plastics with aluminum lamination, may also be used. Other barrier materials are known in the art that can be sealed together to form the blisters and channels. If plastic film may be used, the layers may be bonded together, illustratively by heat sealing. Illustratively, the material has low nucleic acid binding capacity. If fluorescence detection is used, optically transparent material may be used in the appropriate areas of the pouch (e.g., in the vicinity of the second-stage array).

Turning back to FIG. 14A, the illustrative pouch 1400 includes a sample preparation blister 1405 where a sample containing nucleic acids to be amplified and analyzed is introduced into the pouch 1400. The pouch further includes a first-stage PCR blister 1410, a volumetric well 1415 for measuring a portion of the product from first-stage PCR prior to second-stage PCR, and an array of reaction wells 1430 for second-stage PCR. The volumetric well 1415 may also be fluidly coupled to a reagent blister 1425, where reagents for second-stage PCR are introduced, and a mixing blister 1420. A sample for second-stage PCR may be prepared by repeatedly mixing the contents of volumetric well 1415 between blisters 1420 and 1425. The second-stage array 1430 may also be fluidly connected to a waste receptacle 1435. Alternatively, blister 1410 may be used for both sample preparation and first-stage PCR and blister 1405 may be used as a waste receptacle for, for example, sample preparation waste(s). Means for introducing sample and reagents into the pouch 1400 are not illustrated in FIG. 14A, but one will appreciate that a device similar in form to fitment 590 of FIG. 1 can be fitted to pouch 1400 and used for introduction of sample and reagents into the pouch 1400. Likewise, a sealable port (not shown) may be provided for introduction of sample into the pouch 1400 and one or more sealable ports may be provided for introduction of a liquid reagent or a hydration buffer. In addition, the pouch 1400 may include dehydrated (e.g., freeze dried) reagents in a fitment or a similar structure that may be hydrated with a suitable hydration buffer prior to use of the pouch.

Figure 15A:
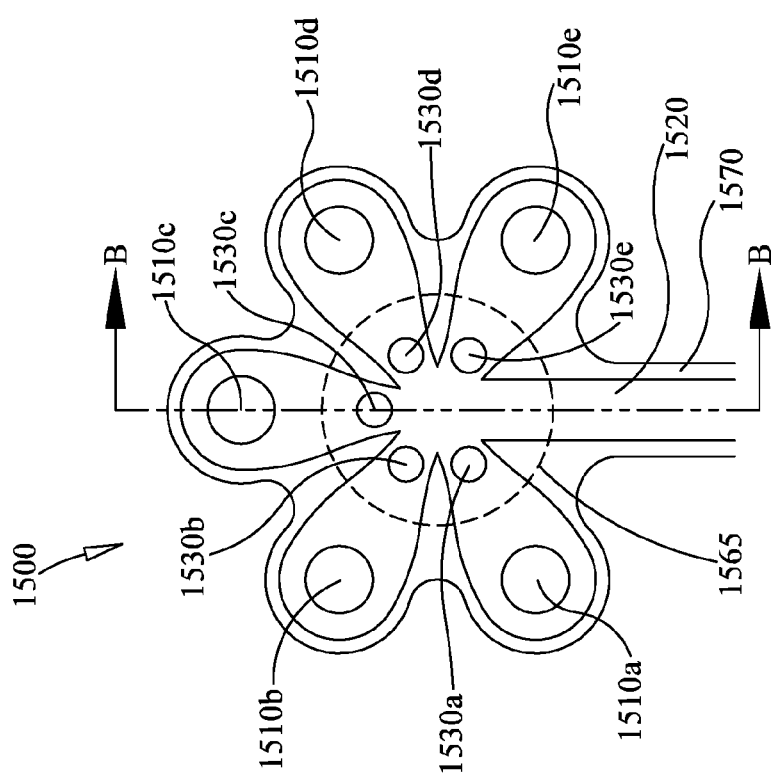
FIG. 15A is a schematic illustration of a second-stage PCR array that may be included in the pouch of FIG. 14A.

Referring now to FIG. 15A, an array 1500 of wells that may be used for second-stage PCR is illustrated in greater detail. Array 1500 may be a standalone array or it may be included as part of a wider array, such as part of array 1430. Array 1500 includes individual wells 1510a-1510e. Each of wells 1510a-1510e may be used for a second-stage PCR reaction. In the illustrated embodiment, the wells 1510a-1510e are fluidly connected to a fill channel 1520; holes 1530a-1530e are formed in the fill channel for filling each of the well. In one embodiment, the wells 1510a-1510e can be sealed off from the fill channel 1520 and from each other (i.e., cross-talk between the well can be prevented) by applying a seal (e.g., a heat seal) or pressure in or around the region illustrated at 1565. Thus, the single seal 1565 closes off wells 1510a-1510e from fill channel 1520 and from each other. The cross-sectional structure of the array 1500 and the flow path for filling the wells is illustrated below in FIGS. 15B and 153. And while array 1500 is illustrated with five wells 1510a-1510e associated with the fill channel 1520, one will appreciate that more or fewer reaction wells can be associated with a fill channel and that multiple fill channels can be fluidly connected to multiple clusters of wells. Multiple arrays 1500 may be used in combination to create larger arrays.

Figure 15C:
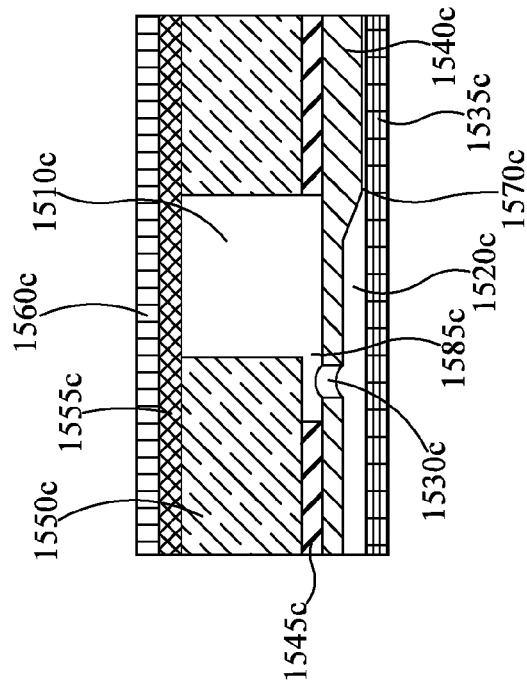
FIG. 15C is a cutaway view of the array of FIG. 15A illustrating one well of the array and an alternate system for filling the well.
Figure 15B:
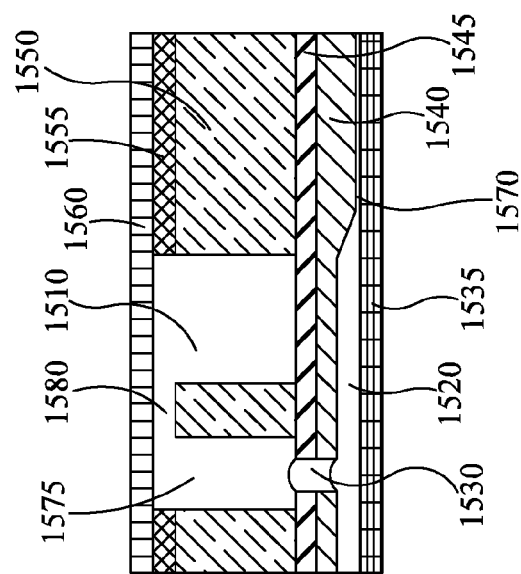
FIG. 15B is a cutaway view of the array of FIG. 15A along the line B-B illustrating one well of the array and a series of channels for filling the well.

Referring now to FIGS. 15B and 15C, cross-sectional views are illustrated along the line B-B of FIG. 15A. The cross-sectional views of two different embodiments of well filling systems are shown. The portion of the array 1500 illustrated in cross section in FIGS. 15B and 15C is made of layers similar to those shown in FIG. 14B; it should be noted that the array 1500 may be included as part of the pouch 1400 shown in FIG. 14A. The array 1500 is fabricated from a first film layer 1535, a second film layer 1540, an adhesive layer 1545, a card layer 1550 in which a well 1510 of the array may be formed, a second adhesive layer 1555, and a third (outside) film layer 1560.

In FIG. 15B, the fill channel 1520 may be formed by leaving a gap between the first and second film layers 1535 and 1540 where liquid can flow. FIG. 15C shows a similar fill channel 1520c formed by leaving a gap between the first and second film layers 1535c and 1540c. The fill channels may be defined by weld lines 1570 or 1570c that seal the first and second film layers together around the array. An example of how these welds 1570 may be applied is shown in FIG. 15A. In FIG. 15B, the fill hole 1530 may be formed by making selective cutouts in the second film layer 1540 and in the first adhesive layer. In FIG. 15C, the fill hole 1530c may be formed by making a selective cutout in the second film layer 1540c.

In FIG. 15B, a well filling channel that flows around and over the well 1510 for filling well 1510 may be formed by making a cutout 1575 in the card layer and a cutout 1580 in the adhesive layer 1555, although other ways of forming these channels are possible. The design of the well filling channel of FIG. 15B may, for instance, help to suppress cross-talk between wells because the flow path is convoluted. Likewise, because the fill channel 1520 and the fill hole 1530 are formed between two film layers 1535 and 1540, the fill hole 1530 and the array 1500 can be sealed, illustratively with a heat seal device or by pressure, illustratively by a bladder that inflates against the array 1500. In FIG. 15C, the well filling channel flows directly into the well 1510c and may be formed by making a cutout 1585c in the first adhesive layer 1545c that fluidly connects the fill hole 1530c to the well 1510c. It is expected that the filling design of FIG. 15C will also generally suppress cross-talk between wells. However, the design of FIG. 15C may be sealed, illustratively, with a heat seal device, which may provide better sealing than pressure alone. In one embodiment, wells of a second-stage array (e.g., well 1510) may be under a partial vacuum to facilitate drawing fluid from the fill channel 1520 into the well 1510. In another embodiment (not shown), wells of a second-stage array may include an exit hole and a downstream waste receptacle to allow air and excess fluid to escape so that fluid can flow from the fill channel 1520 and into the well 1510 without having to maintain the pouch and the array under vacuum.

Figure 16A:
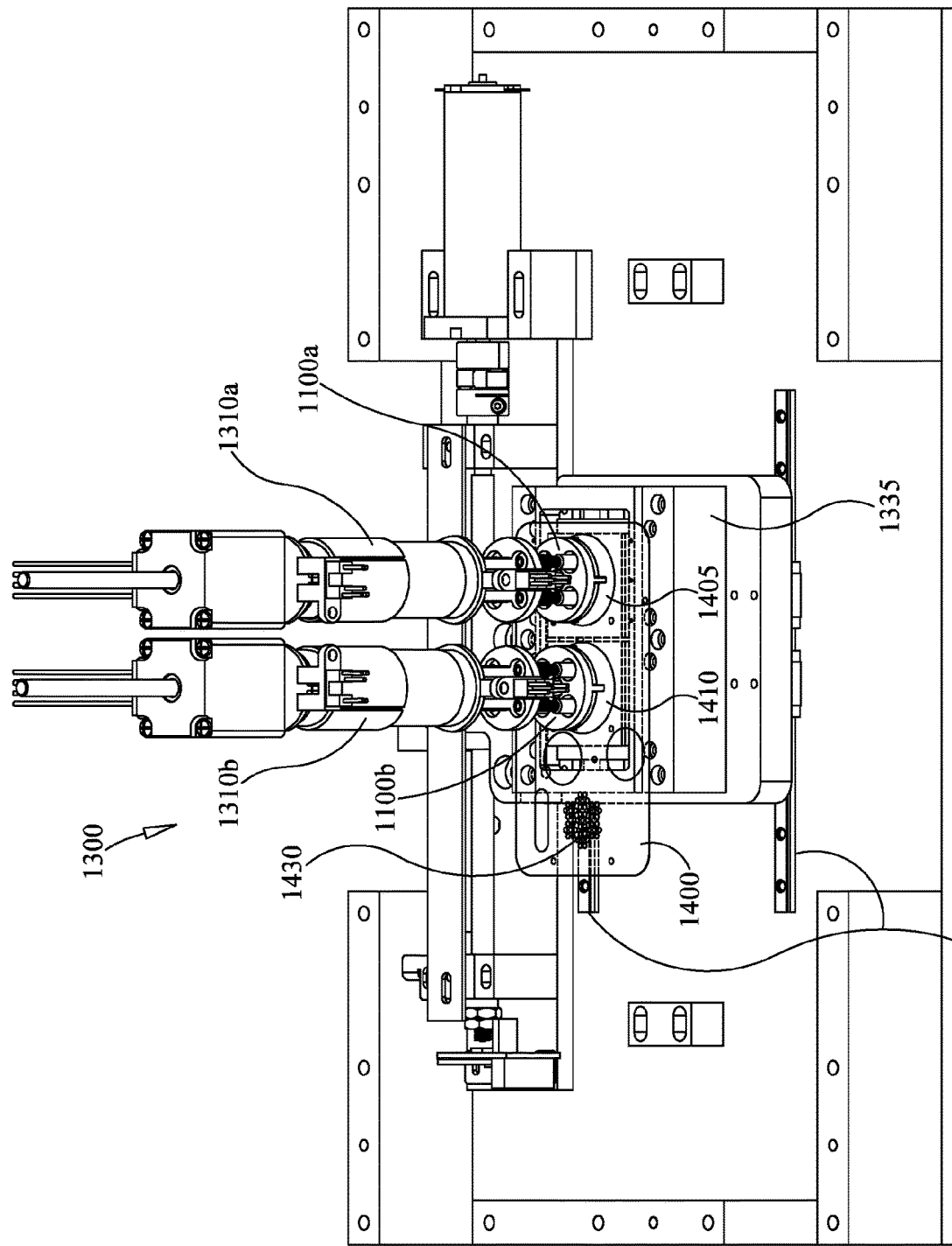
FIGS. 16A-16F illustrate an example of a series of manipulations for preparation and amplification of nucleic acids that may be performed by an instrument of FIGS. 13A and 13B with a pouch of FIG. 14A.
Figure 16B:
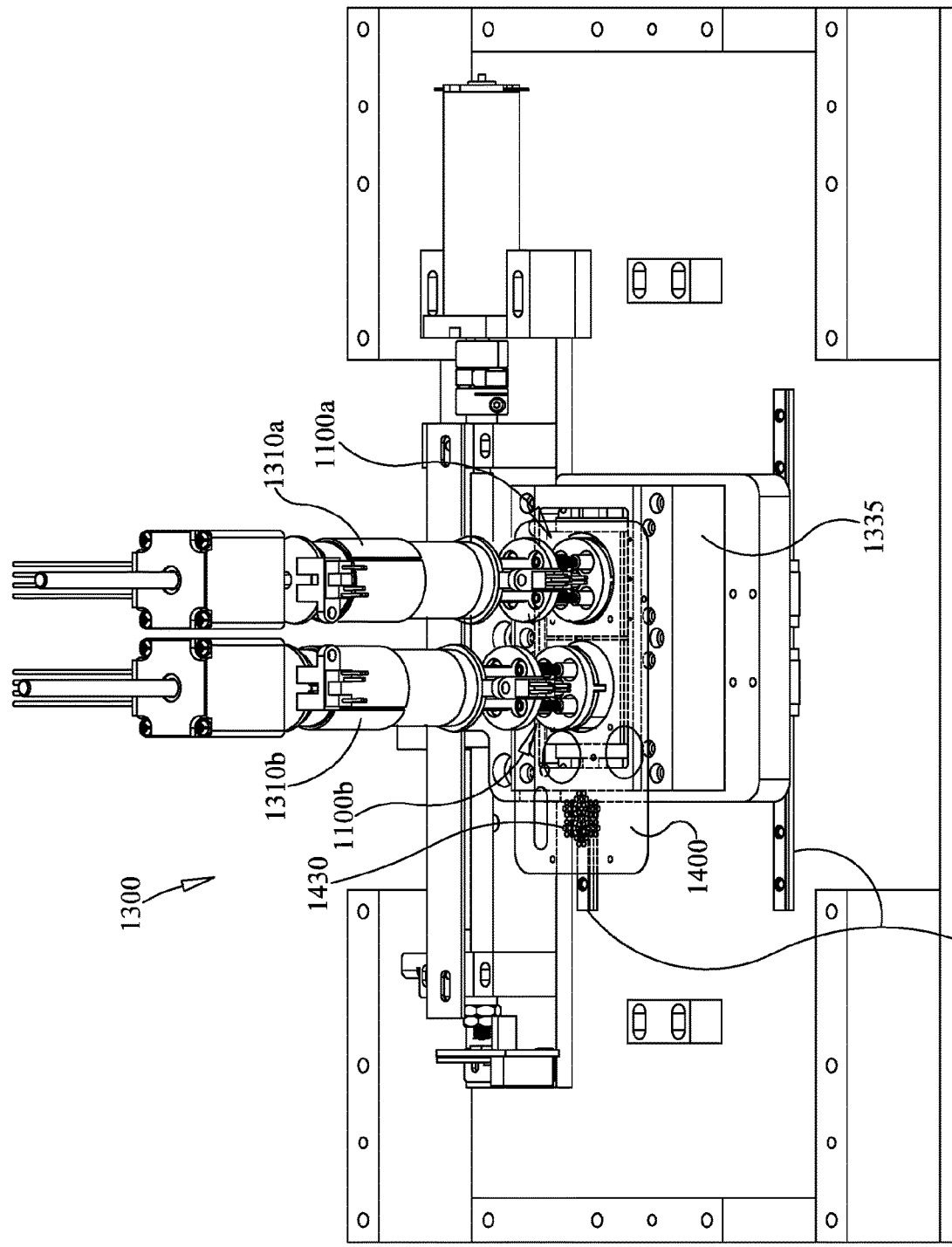

Referring now to FIGS. 16A-16F, an illustrative sequence of operations that may be performed by instrument 1300 using pouch 1400 for sample preparation, first-stage PCR, and second-stage PCR are described. Note that the covers 1315 and 1320 depicted in FIG. 13A have been removed for clarity, but they would normally be in place while the instrument is in operation and the pouch 1400 would be illustratively inserted between the outer and inner covers for positioning the pouch relative to the wipers, heaters, and the like. In FIG. 16A it will be understood that a sample has been added to pouch 1400 and the pouch has been positioned in the instrument 1300. However, in some embodiments, the instrument may be configured for injection of the sample into the pouch when the pouch is in the instrument. As will be discussed in greater detail below, a sample may be introduced in to blister 1405 via fill channel 1440, which is illustrated in FIG. 14A. In a first step, heater assembly 1335 may be translated so that a heater element is in contact with blister 1405 for heated and cooled sample preparation. In this view, heater elements 1386 and 1387 are not visible, but, for instance, heater element 1386 may be positioned so that the heater assembly 1335 is translated along rails 1392 so that the sample can be heated for cell lysis, cooled (e.g., to about 5-10° C.) by heater 1387 for nucleic acid recovery with magnetic beads, cooled (e.g., to about 5-10° C.) by heater 1387 for magnetic bead washing steps, and heated (e.g., to about 50-60° C.) by heater element 1386 for elution from the magnetic beads. In FIG. 16B, wiper head 1100a may be lowered until the wiper blades (not shown) contact blister 1405. The wiper head 1100a may then be rotated with motor 1310a; the combination of heat and agitation may be sufficient to efficiently lyse most cell and virus types. However, while a mixing apparatus is depicted for lysis, it is appreciated that the mixing apparatus may be replaced with other means for lysis, such as, but not limited to, a sonication device, a bead beater motor, a freeze/thaw mechanism, a paddle beater, laser lysis, slip plate hammer mechanism, hammer drill beater mechanism, a homogenizer, a combination thereof, or another cell lysis apparatus known in the art. It is also understood that sample prep may be omitted or performed ahead of time, and this step may be omitted.

Figure 32A:
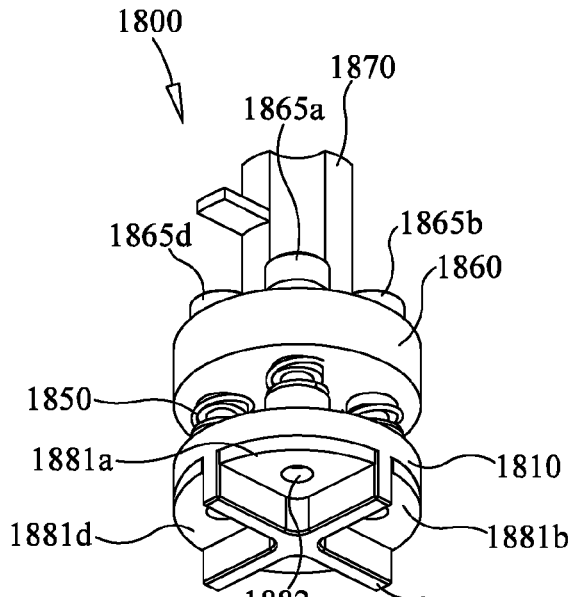
FIGS. 32A-32C illustrate a wiper head with a magnet system according to one embodiment of the present disclosure.

Referring now to FIG. 32A, an embodiment of a wiper head 1800 that may be used for recovery of nucleic acids from a lysate is illustrated. Wiper head 1800 is similar to wiper head 1100 except wiper head 1800 includes a magnet system that can be used for selectively isolating the magnetic beads that may be used in some embodiments described herein for recovering nucleic acids from a cell lysate. The proximal end of the wiper head 1800 includes a wiper body 1810 with wiper blades 1849. The wiper head 1800 also includes outer spring members 1850, an upper body 1860, and pins 1865a-1865d (pin 1865c not shown) that couple the upper portion of the wiper head to the lower portion. In one embodiment, the wiper head may be configured such that the spring members 1850 and the pins 1865a-1865d can regulate the amount pressure that the wiper head 1810 and wiper blades 1849 can exert on a fluid-filled blister.

Figure 33:
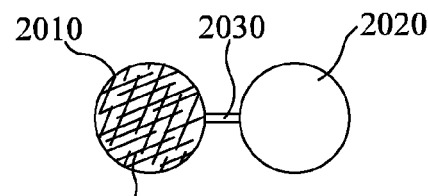
FIG. 33 illustrates a pair a reaction blisters according to one embodiment of the present disclosure.
Figure 33A:
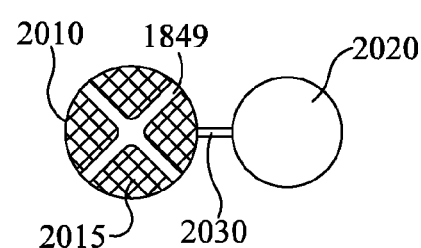
FIGS. 33A-33C illustrate the reaction blisters of FIG. 33 as they interact with the wiper head of FIGS. 32A-32C.
Figure 32B:
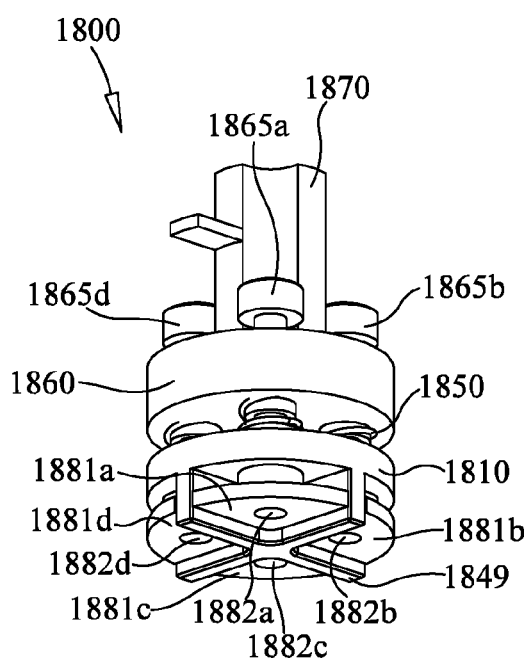
Figure 33B:
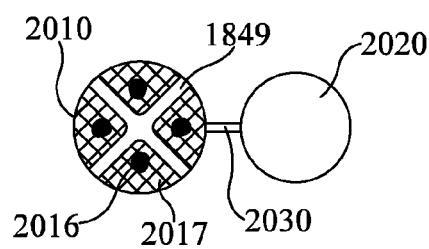
Figure 33C:
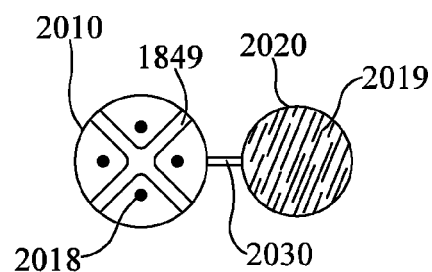

The illustrated wiper body 1810 also includes pressure members 1881a-1881d (pressure member 1881c not shown) disposed in the quadrants between the wiper blades 1849 that can be deployed downward in one aspect to place pressure on a fluid-filled blister (see, e.g., FIG. 32B) and can be deployed further downward in another aspect to squeeze the fluid contents of a blister to another blister (see, e.g., blister 2020 in FIG. 33C). In the illustrated example, the pressure members 1881a-1881d may be deployed by lowering the wiper head 1800 past the point that the wiper blades 1849 contact the blister; continuing to lower the wiper head 1800 can compress the wiper blades 1849 up and/or press the pressure members 1881a-1881d down until the magnets 1882a-1882d can gather the magnet beads or even further until the pressure members 1881a-1881d are pressed flat against the blister to compress fluid out of the blister.

Referring further to FIG. 32A in combination with FIGS. 32B-32C and FIGS. 33-33C, a series of views of the wiper head 1800 the magnet system of magnets 1882a-1882d and how they act on a fluid-filled blister are illustrated. FIG. 33 illustrates a pair of blisters 2010 and 2020 with an interconnecting fluid channel 2030 that may be included in a sample card similar to pouch 1400. In one embodiment, blisters 2010 and 2020 may be similar to the sample preparation blister 1405 and first-stage blister 1410 that are included in pouch 1400 of FIG. 14A. In another embodiment, blister 2010 may be a sample preparation blister, blister 2020 may be a waste receptacle, and the card may include another blister (not shown) for first-stage PCR. In FIG. 33, blister 2010 is shown to contain a slurry of cell lysate and magnetic beads schematically illustrated at 2015. The magnetic beads may comprise a silica-coated magnetic material or the like that is capable of binding to and isolating nucleic acids from a cell lysate. An illustrative process for magnetic bead recovery of nucleic acids from a lysate is discussed in detail elsewhere herein, for example, in reference to FIG. 1 and such a process may be used in this and other embodiments herein.

Figure 32C:
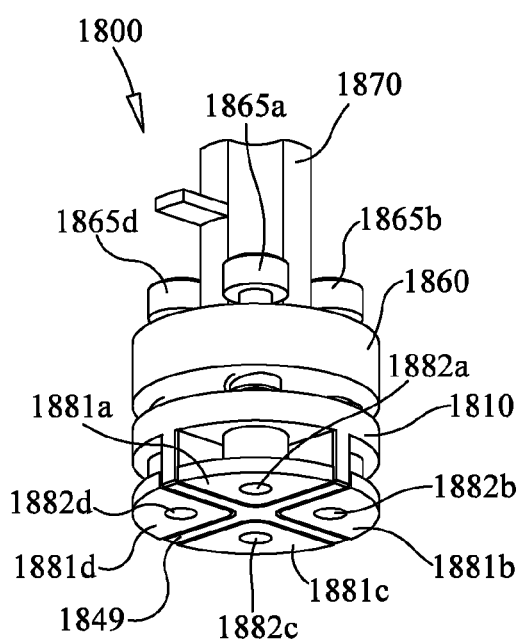

Referring now to FIGS. 32A and 33A, a first state of the wiper head 1800 and how the wiper blade 1849 may interact with blister 2010 is illustrated. In the first state, the wiper blade 1849 may be pressed into the blister 2010 such that rotation of the wiper head 1800 may mix the slurry 2015, for instance, for exposure of the magnetic beads to the lysate. FIGS. 32B and 33B illustrate a second state where the head 1800 has, for example, been lowered further so that the so that the pressure members 1881a-1881d are closer to the blister 2010 so that the magnets 1882a-1882d can begin to gather the magnetic beads. The partially gathered magnetic beads are shown at 2016 and the partially cleared slurry is schematically shown at 2017. As the pressure members and the magnets are moved closer to the blister, the magnetic beads can be consolidated by, for example, rotating the wiper head back and forth in a small arc (e.g., in a range of about +/−5-20°). Once the magnetic beads are fully captured by the magnets and are fully consolidated, the wiper head 1800 may be fully lowered so that the pressure members 1881a-1881d press the blister 2010 flat to squeeze the lysate through channel 2030 into blister 2020. This is illustrated in FIGS. 32C and 33C. The captured magnetic beads are shown at 2018 and the waste lysate is shown at 2019. The steps illustrated in FIGS. 32A-32C and 33-33C may be repeated for washing the beads 2018 and subsequent elution of the captured nucleic therefrom.

Figure 16C:
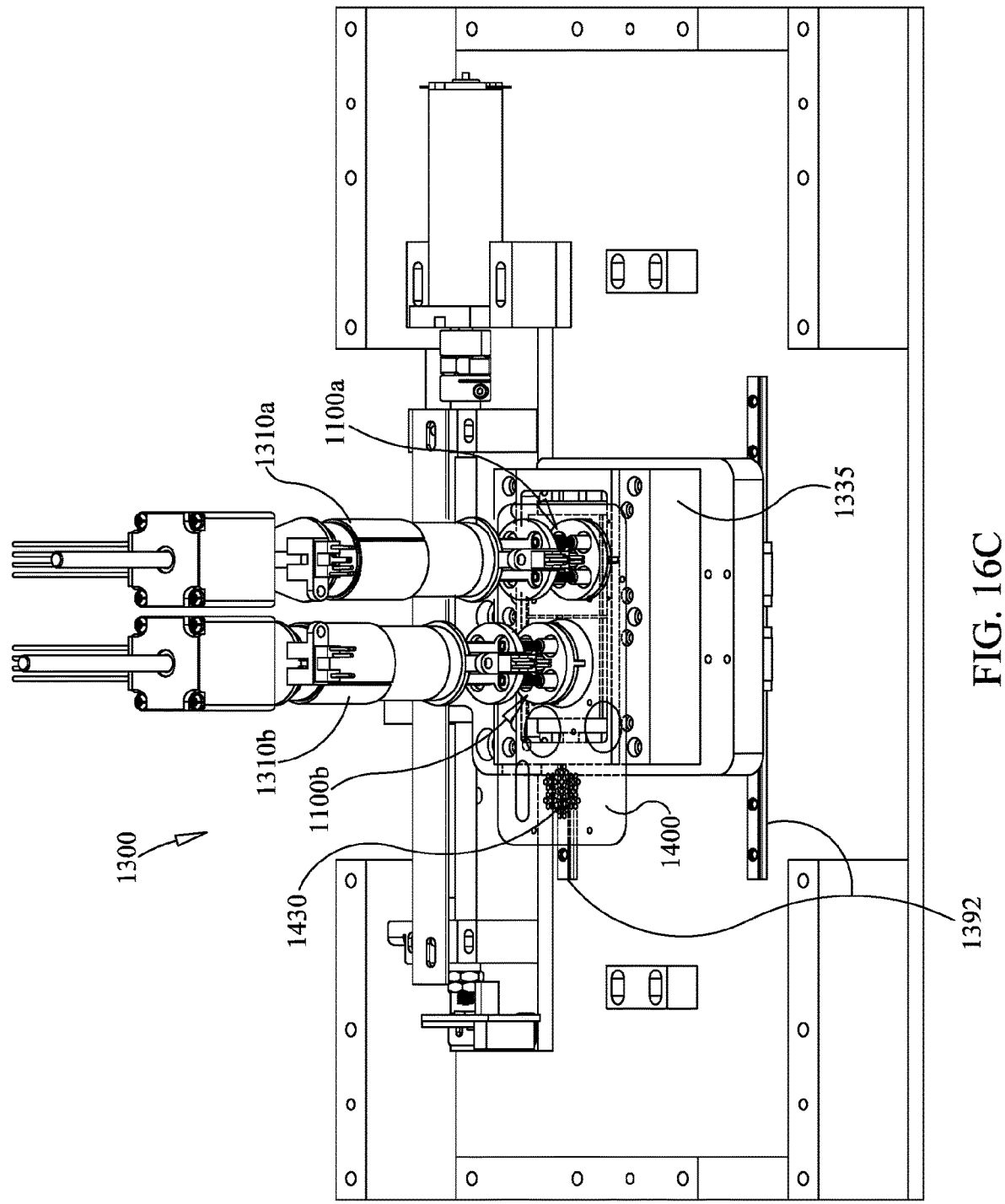
Figure 16D:
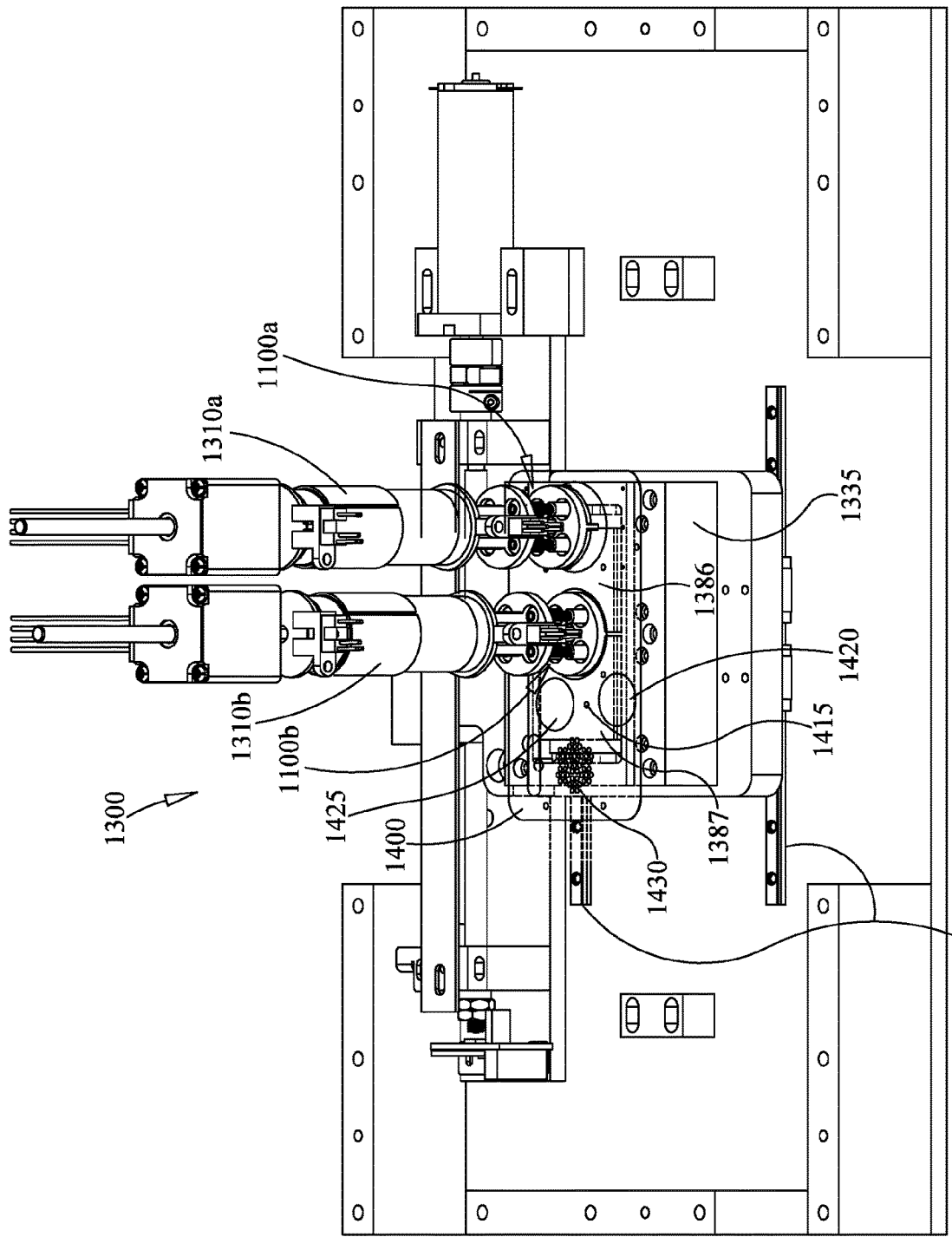

Referring again to FIGS. 16A-16F, following lysis and nucleic acid recovery, the recovered nucleic acids may be moved to blister 1410 for first-stage PCR. This is illustrated in FIG. 16C where wiper head 1100a has been lowered so that the pressure members of the wiper head can flatten (as shown in, for example, FIG. 11B) against the blister so that the wiper head can plunge at least a portion of the contents of blister 1405 to blister 1410. At about the same time (i.e., before, simultaneously, or after), heater assembly 1335 may be repositioned for so that blister 1410 may be under temperature control of both of heaters 1386 and 1387, as described in relation to FIG. 6. This is depicted in FIG. 16D. Also in FIG. 16D, wiper head 1100b is lowered until the wiper blades (not shown) contact blister 1410. In an alternative embodiment with one mixer, the pouch could be translated or the mixer could be translated so that the mixing head 1100 could contact various blisters of the pouch. With the heaters 1386 and 1387 and the wiper head 1100b in place, first-stage PCR may be accomplished by lowering the mixing head 1100 so that the wiper blades divide the first-stage PCR into separate and discrete volumes and rotating the wiper head to move the contents of blister 1410 between the two heaters 1386 and 1387, as previously described in reference to FIGS. 6-9C. In an alternative embodiment, first-stage PCR thermocycling may be accomplished by translating heater assembly 1335 or the pouch 1400 back and forth along rails 1392 so that the contents of the blister 1410 are repeatedly under temperature control of heater 1386 (e.g., denaturation), then heater 1387 (e.g., annealing), then heater 1386 (e.g., elongation and denaturation), etc.

In one embodiment, thermocycling by translation of the heater assembly 1335 or the pouch 1400 may be combined with the mixing action of the wiper head 1100 illustrated, for example, in FIG. 8C. For instance, mixing using the wiper head 1100 can be combined with thermocycling by translation of the heater assembly 1335 to mix the contents of blister 1410 to increase temperature uniformity of the fluid in the blister. Likewise, mixing the fluid in the blister can be combined with thermocycling by translation of the heater assembly 1335 to increase the effective diffusion rate to improve the chemistry of PCR. In one aspect, the wiper head may be rotated at a constant speed while, for example, the heater assembly is translated back and forth or the wiper head may, for example, be rotated at intervals timed to correspond to the transition of the blister being under control of heater 1387 and then heater 1386.

Following first-stage PCR in blister 1410, a portion of the amplified nucleic acids may be moved to the volumetric well 1415 and mixed with second-stage PCR reagents (polymerase, dNTPs, etc.) by mixing between blisters 1420 and 1425. Mixing may be accomplished with a bladder system similar to the bladder system 808 of FIG. 2 or another pressure applying system. In some embodiments, it may be desirable to prepare the sample for second-stage PCR with heat. This is not depicted in FIGS. 16A-16F, but heater assembly 1335 can be positioned for such a step by moving heater 1386 adjacent to blisters 1415, 1420, and 1425 if a true hot start is desired. It is also understood that second-stage PCR reagents may be provided in each second-stage well.

Figure 16E:
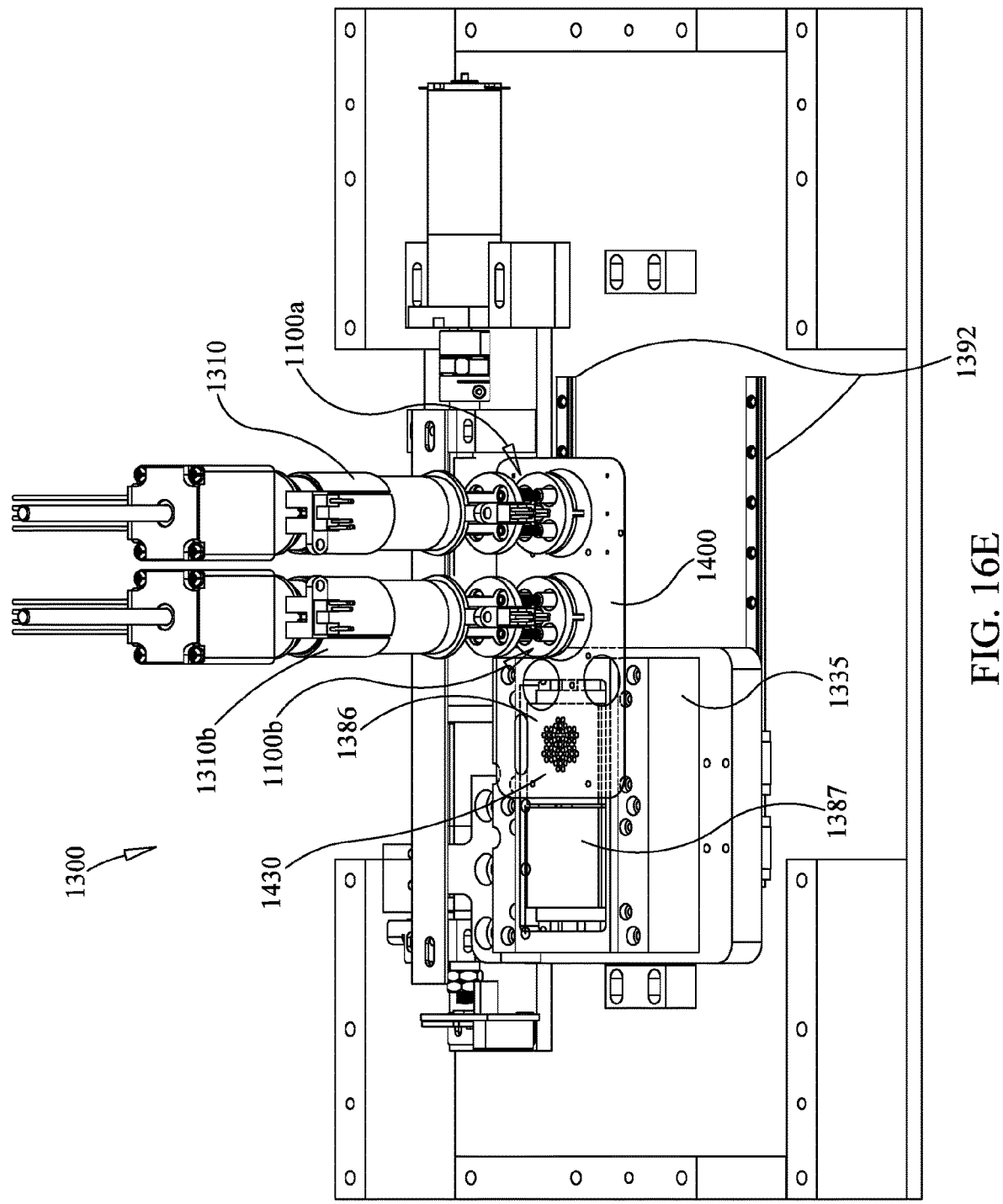
Figure 16F:
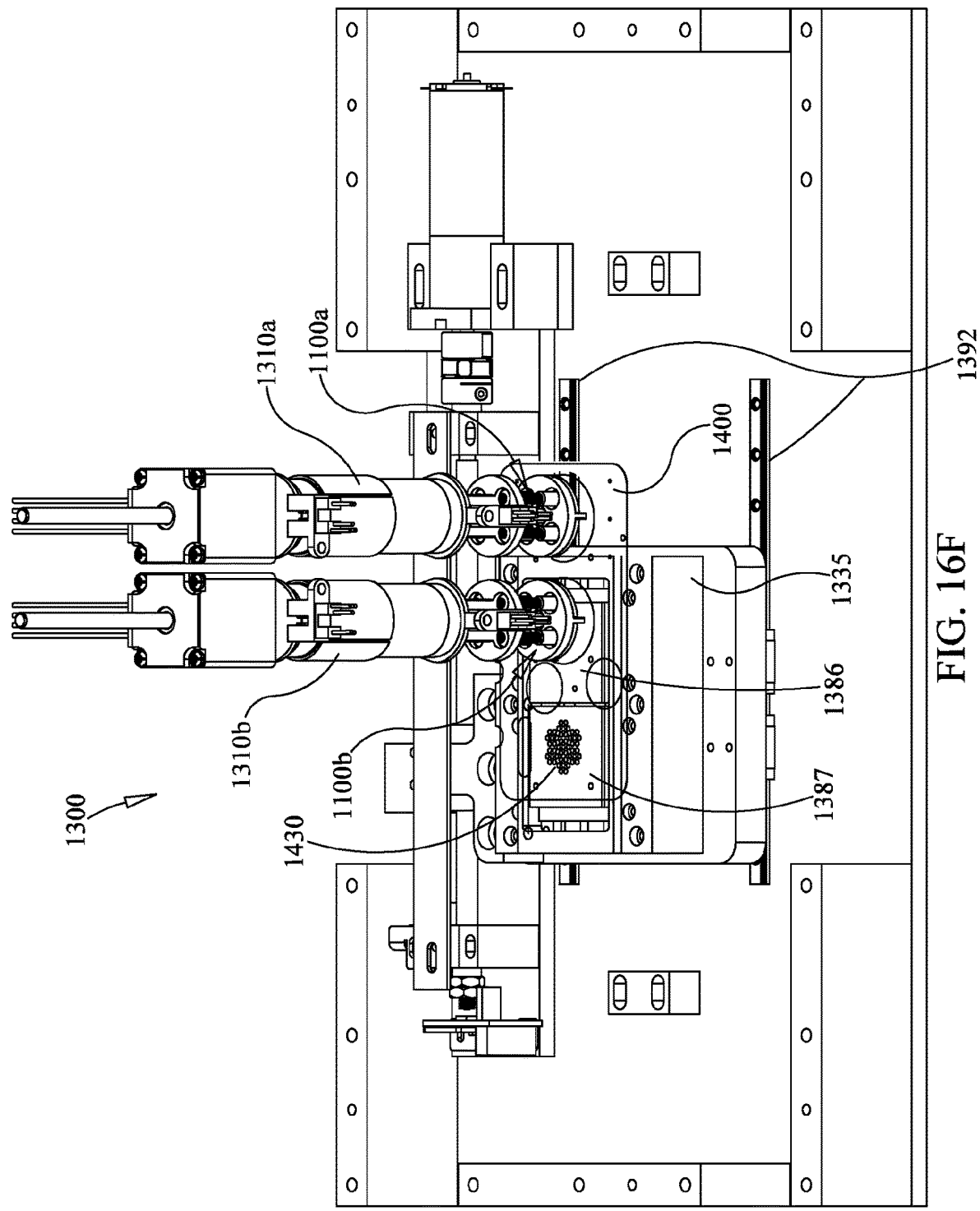

Following preparation of the sample for second-stage PCR in blisters 1415, 1420, and 1425, the sample may be moved to the array 1430 for second stage PCR. As depicted in FIGS. 16E and 16F, thermocycling for second-stage PCR may be accomplished by translating heater assembly 1335 relative to the array 1430 so that the array and the contents of the individual wells are under temperature control of heater 1386 (e.g., denaturation), then heater 1387 (e.g., annealing), then heater 1386 (e.g., elongation and denaturation), etc. It is not depicted in these views, but a pressure applying means (e.g., an inflatable bladder, such as a clear, flexible bladder configured to apply pressure to a blister while allowing simultaneous or substantially simultaneous fluorescent measurement) may be positioned over the array to seal the contents of the individual well in the wells and prevent cross-talk between the wells. Likewise, such a pressure applying means can also improve contact between the array and the heaters and, thus, increase the efficiency of heat transfer. It is understood that the wells may be sealed by other means, such as heat sealing. It is not depicted in these views, but nucleic acid amplification in the array 1430 may be monitored with an optical array like camera 1325 depicted in FIGS. 13A and 13B.

FIGS. 16A-16F depict instrument 1300, but one will appreciate that the operations performed in these views could also be performed on instrument 1200 or a similar instrument. Likewise, the operations depicted in these views are performed with pouch 1400, but this is merely exemplary insofar as the operations depicted in these views could be performed with other pouch types and configurations.

Figure 17:
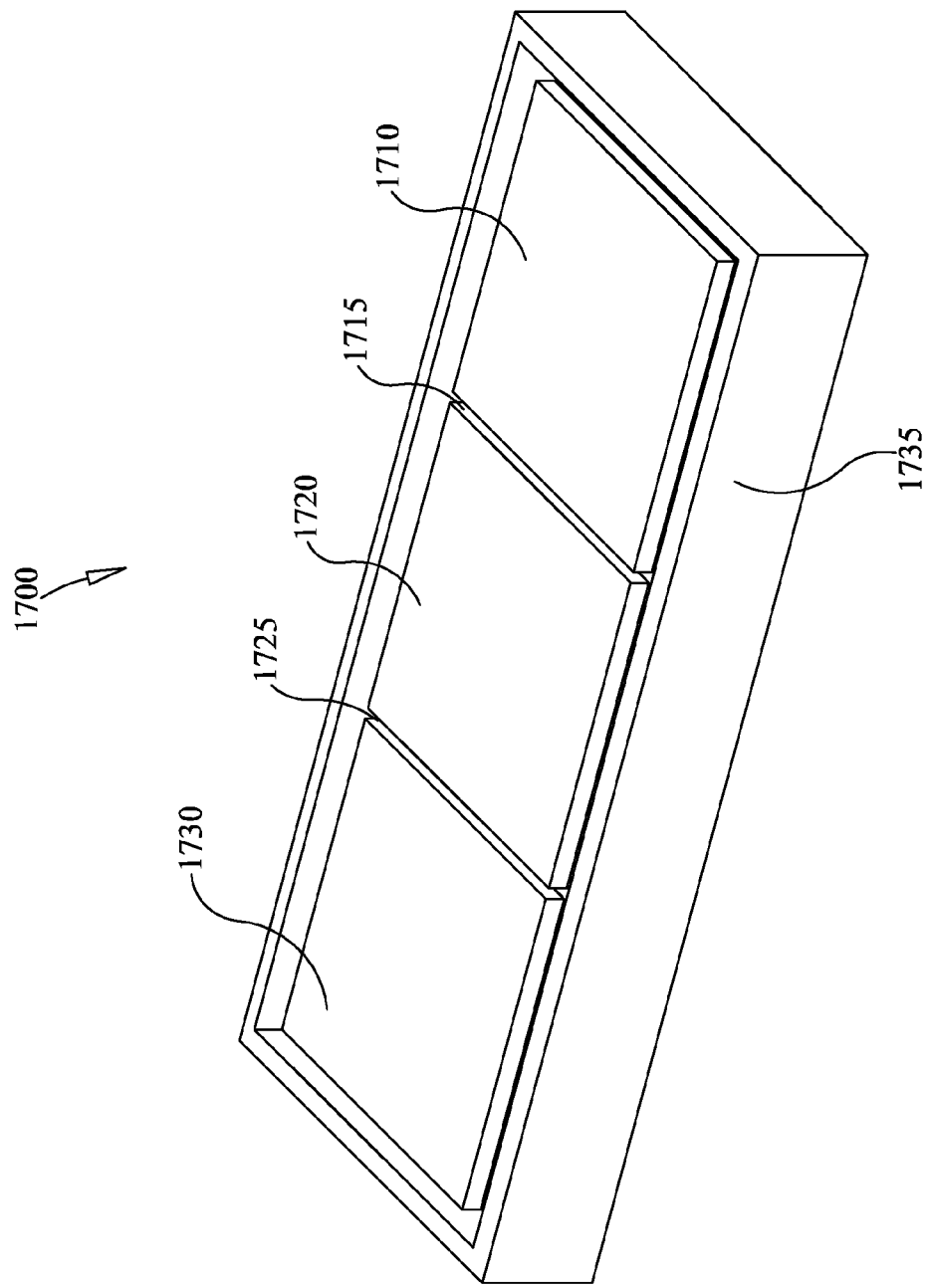
FIG. 17 schematically illustrates a heater system that may be included in the thermocycling instruments of FIGS. 12A and 12B and 13A and 13B.

Referring now to FIG. 17, an alternative embodiment of a heater assembly 1700 is illustrated. While instruments 1200 and 1300 of FIGS. 12B and 13B depict heaters assemblies 1270 and 1335 with two heater elements, heater assembly 1700 includes three heater elements 1710, 1720, and 1730 that are housed in housing 1735. In one embodiment, heaters 1710 and 1730 are set to the same temperature (e.g., a denaturation temperature in a range of about 90° C.-110° C.) and heater 1720 may be set to an intermediate temperature (e.g., about 55° C. to about 65° C.), illustratively, for annealing. In one embodiment, thermocycling of the fluid contents of a blister (e.g., blister 1410 or array 1430 of FIG. 14) may use all three heaters. For example, a blister to be thermocycled may be started at heater 1710 for denaturation, the heater assembly 1700 may then be translated so that the blister may be under temperature control of heater 1720 for annealing, the heater assembly 1700 may then be translated so that the blister may be under temperature control of heater 1730 for elongation/denaturation, and then the process may be repeated with the heater assembly translating the opposite direction. Thermocycling with three heaters instead of two may, for example, provide greater temperature uniformity and reduce so called 'edge effects' where the portions of a blister on the leading edges spend less time at a given temperature. Because the heater assembly 1700 allows for transitions from denaturation to annealing to denaturation in each direction, it is believed that all portions of a blisters will receive more equal exposure to a given temperature. In another embodiment, the three heaters may be set at three different temperatures, illustratively, an annealing temperature, an elongation temperature, and a denaturation temperature.

Heaters 1710, 1720, and 1730 may be Peltier devices, resistance heaters, induction heaters, electromagnetic heaters, thin film heaters, printed element heaters, positive temperature coefficient heaters, or other heaters as are known in the art. In one embodiment, heater 1720 may include a Peltier element. As discussed above in reference to heaters 1286 and 1287, while heater 1720 may not be thermocycled, it may, for instance, be desirable to include a Peltier element. Unlike a typical resistance heater, Peltier elements can actively cool as well as heat samples. In another embodiment, either one or both of heaters 1710 or 1730 may also include a Peltier element. For instance, one or both of heaters 1710 or 1730 may be positioned to participate in steps such as, but not limited to, heated/cooled sample prep, hot start, and the like that may benefit from the fine temperature control and active cooling provided by a Peltier element. Illustratively, insulating spacers 1715 and 1725 may be provided between heaters 1710 and 1720 and 1720 and 1730, respectively. Any suitable insulating material may be used, including foam, plastic, rubber, air, vacuum, glass, or any other suitable material illustratively of low conductivity. In embodiments where heaters 1710, 1720, and 1730 are held at a generally constant temperature, run time and energy usage may be substantially reduced.

Referring again to FIG. 14A, two alternative sequences for filling the pouch, preparing a sample, performing first-stage PCR, and performing second-stage PCR are described. In a first method, sample preparation and first-stage PCR are performed in separate blisters. This is referred to herein as the "three zone method." In a first step, a sample is injected into blister 1405 via fill channel 1440. In one embodiment, cells, viruses, and the like are lysed in blister 1405 using the wiping system described in detail elsewhere herein. Alternatively, cell lysis may be accomplished with an alternative lysis device such as, but not limited to, a sonication device or a bead beater or by chemical lysis. Lysis may be aided by heating the sample (e.g., to about 70-90° C.) with one or more heater elements of the heater assembly described in detail elsewhere herein. Following lysis, the sample may be cooled with a thermoelectric cooler element (i.e., a Peltier element) to a temperature in a range of about 0° C. to about 20° C. (e.g., about 10-15° C.) to aid in binding to magnetic beads. Other cooler elements include, but are not limited to, fluid or gas heat exchange elements, fan cooled heat sinks, heat pipes, condensation units, and the like.

Magnetic beads may be injected into blister 1405 via fill channel 1440 in order to recover nucleic acids from the lysate, which may be prior to or subsequent to lysis. Illustratively, the magnetic beads and the lysate may be mixed cold (e.g., in a range of about 0-10° C., illustratively by adjusting the temperature of one of the heaters). Once the magnetic beads and the lysate have been thoroughly mixed for a sufficient time, the magnetic beads may be gathered in blister 1405 with a magnet illustratively provided in the instrument and the spent lysate may be sent to liquid waste via channel 1445. Then wash buffer may be injected via fill channel 1440. The wash buffer and the magnetic beads may be mixed cold (e.g., in a range of about 0-10° C.). The magnetic beads may be gathered again and the spent wash buffer may be flushed to liquid waste via channel 1445. The wash cycle may be repeated at least one more time. Following the wash, elution buffer (plus first-stage PCR primers) may be injected into blister 1405 via fill channel 1440. The elution buffer (plus first-stage PCR primers) and the magnetic beads may be mixed hot (e.g., at about 70-90° C.), illustratively, under control of one or more heaters.

For first-stage PCR, PCR master mix (e.g., a polymerase, dNTPs, and other amplification components known in the art) may be injected into blister 1410 via fill channel 1450. The PCR master mix may be heated (e.g., to about 57° C.) prior to introduction of the eluate from the magnetic beads. In blister 1405, the magnetic beads may be gathered again and the eluate may be sent to blister 1410 via channel 1465.

First-stage PCR may be performed in blister 1410 with rotary movement with blister 1410 under temperature control of two heaters as described in detail elsewhere herein. Alternatively, first-stage PCR thermocycling may be performed by translating the heater assembly or the pouch 1400 so that blister 1410 may be under control of one heater and then another. The channels into and out of blister 1410 are closed, illustratively with hard seals, during first stage PCR. In some embodiments, it may be possible to speed up first-stage PCR in the pouch by employing a volume reduction protocol. For instance, a volume reduction protocol may include performing several cycles (e.g., 5-10) of PCR with an initial volume (e.g., ~100 μL) in blister 1410, purging approximately half the volume of blister 1410, performing several more cycles of PCR (e.g., 5-10), and again purging approximately half the volume of blister 1410. Volume reduction can reduce the cycle time for a PCR reaction because smaller volumes of liquid have less thermal mass and can be thermocycled more quickly than larger volumes.

Following a sufficient number of cycles of first-stage PCR (e.g., 20-30 cycles), a small sample (e.g., ~1-5 μL) of first-stage PCR may be sent to dilution well 1415. Channel 1470 may be opened; channels 1475-1485 are closed. The sample for second-stage PCR may be prepared by injecting the second-stage PCR master mix into blister 1425 via channel 1460. Seals are closed on channels 1470 and 1485; seals are opened on channels 1475 and 1480. Blisters 1420 and 1425 and well 1415 may be heated. The sample in well 1415 may be mixed with the master mix by mixing between blisters 1425 and 1420 and well 1415 to dilute first-stage PCR product for second-stage PCR. Channel 1485 is then opened so that the second-stage PCR mix can be transferred into the second-stage PCR array 1430. In another embodiment, the pouch 1400 may include one or more additional dilution wells and sets of mixing blisters downstream from well 1415 and blisters 1425 and 1420 and upstream from array 1430. For example, in some embodiments with concentrated first-stage PCR primers or with highly concentrated product, it may be desirable to dilute the first-stage primers and product to a degree greater than can be achieved with one dilution well. The mixture for second-stage PCR may be heated for a physical 'hot-start' prior to injection into the second-stage PCR array 1430. Thermocycling for second-stage PCR in array 1430 may illustratively be accomplished by translating the heater assembly back and forth as previously described.

In the second method, sample preparation and first-stage PCR are performed in the same blister. This is referred to herein as the "two zone method." In a first step, a sample may be injected into blister 1410 via fill channel 1450. In one embodiment, cells, viruses, and the like are lysed in blister 1410 using the wiping system described in detail elsewhere herein. Alternatively, cell lysis may be accomplished with an alternative lysis device such as, but not limited to, a sonication device or a bead beater or chemical lysis. Lysis may be aided by heating the sample to an elevated temperature (e.g., about 70-90° C.) with one or more heater elements of the heater assembly described in detail elsewhere herein. Following lysis, the sample may optionally be cooled with a thermoelectric cooler element (i.e., a Peltier element) to a reduced temperature (e.g., a temperature below ambient temperature such as, but not limited to, ~0-10° C.).

Magnetic beads may be injected into blister 1410 via fill channel 1450 in order to recover nucleic acids from the lysate. Magnetic beads are injected into blister 1410 via fill channel 1450. The magnetic beads and the lysate may be mixed cold (e.g., at a temperature in a range of about 0-10° C.). Once the magnetic beads and the lysate have been thoroughly mixed for a sufficient time, the magnetic beads may be gathered in blister 1410 with a magnet and the spent lysate may be sent to blister 1405 (i.e., the liquid waste blister in this example) liquid waste via channel 1465. Then wash buffer may be injected into blister 1410 via fill channel 1450. The wash buffer and the magnetic beads may be mixed cold (e.g., at a temperature in a range of about 0-10° C.). The magnetic beads are gathered again and the spent wash buffer may be flushed to blister 1405. The wash cycle may be repeated one or more times, if desired. The magnetic beads may be collected into the upstream half of blister 1410, and sent to waste blister 1405 via channel 1465.

For first-stage PCR, the wiper system may be set and elution buffer (plus primers) may be injected into channel 1450 and may be held at an elevated temperature (e.g., about 57° C.). At the same time, first-stage PCR master mix may be injected into channel 1455 and optionally held at an elevated temperature (e.g., about 57° C.) if a true hot-start may be desired. First-stage PCR master mix may be mixed with primers and template in blister 1410 and first-stage PCR may be performed as described above.

Following first-stage PCR, the magnetic beads are gathered and in embodiments where dilution is desired, a small sample (e.g., 1-5 µL) of the first-stage PCR product may be transferred to the dilution well 1415. Channel 1470 is opened; channels 1475-1485 are closed. The sample for second-stage PCR may be prepared by injecting the second-stage PCR master mix into blister 1425 via channel 1460. Seals are closed on channels 1470 and 1485; seals are opened on channels 1475 and 1480. Blisters 1420 and 1425 and well 1415 are heated. The sample in well 1415 may be mixed with the master mix by mixing between blisters 1425 and 1420 and well 1415 to dilute first-stage PCR product for second-stage PCR. Channel 1485 is then opened so that the second-stage PCR mix can be transferred into the second-stage PCR array 1430. Thermocycling for second-stage PCR in array 1430 may be accomplished by translating the heater assembly, by use of a Peltier, or by other means as previously described.

When fluorescent detection is desired, an optical array (see e.g., camera systems 1250 and 1325 of FIGS. 12A and 13A) may be provided. An optical array may include a light source, illustratively a filtered LED light source, filtered white light, or illumination, and a camera. The camera illustratively has a plurality of photodetectors each corresponding to a second-stage well in array 1430 of pouch 1400. Alternatively, the camera may take images that contain all of the second-stage wells, and the image may be divided into separate fields corresponding to each of the second-stage wells. Depending on the configuration, the optical array may be stationary, or the optical array may be placed on movers attached to one or more motors and moved to obtain signals from each individual second-stage well. It is understood that other arrangements are possible.

Example 1: High Density PCR

In one example, it is known that standard commercial immunofluorescence assays for the common respiratory viruses can detect seven viruses: adenovirus, PIV1, PIV2, PIV3, RSV, Influenza A, and Influenza B. A more complete panel illustratively would include assays for other viruses including: coronavirus, human metapneumovirus, rhinovirus, and non-HRV enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The FilmArray® Respiratory Panel (BioFire Diagnostics, LLC of Salt Lake City, Utah) includes Adenovirus, Coronavirus HKU1, Coronavirus NL63, Coronavirus 229E, Coronavirus OC43, Human Metapneumovirus, Human Rhinovirus/Enterovirus, Influenza A, Influenza A/H1, Influenza A/H3, Influenza A/H1-2009, Influenza B, Parainfluenza Virus 1, Parainfluenza Virus 2, Parainfluenza Virus 3, Parainfluenza Virus 4, and Respiratory Syncytial Virus. In addition to these viruses, the FilmArray® Respiratory Panel includes three bacteria: *Bordetella pertussis, Chlamydophila pneumoniae,* and *Mycoplasma pneumoniae*. The high density array 581 is able to accommodate such a panel in a single pouch 510. Other panels are available for the FilmArray®, each assaying for at least 20 pathogens.

Example 2: Fast PCR

A prototype instrument using the pouch and heater configuration of FIGS. 6-8 was used to amplify DNA. A 75 µl sample comprising 10,000 copies of a 110 bp synthetic DNA molecule and a 10× higher primer (5 µM each primer) and DNA polymerase (2 U/µL) concentrations (as compared to standard PCR concentrations, as taught in US 2015-0118715, already incorporated by reference), with dNTPs at 0.45 mM and 5 mM Mg++. 1× LCGreen was used for detection. It is understood that the reaction mixture is illustrative only. Depending on cycling times, enhanced primer and polymerase concentrations may be beneficial. See U.S. Patent App. No. 2015-0118715, already incorporated by reference, for more information on enhanced primer and polymerase concentrations. For example, for cycling times of less than 20 sec, it is desirable to have at least 0.5 µM polymerase and at least 1 µM of each primer in a multiplex reaction or 2 µM of each primer in a single-plex reaction. Heater 986 was set to 90° C. and heater 987 was set to 57° C. This mixture was sealed into blister 549 and run with wiper 989 rotating at a speed of one full rotation every 10 sec. It is understood that the rotational speed corresponds to cycle time.

As a control, PCR chemistry reactions (with boosted primer and polymerase concentrations) were cycled in a standard block thermocycler between 96° C. and 60° C. as fast as the hardware would allow (1 second holds, 48 seconds per cycle). To compare the efficiency of amplification for the two systems, identical PCR reactions were amplified in each instrument over a "cycle course" of 5, 10, 15 and 20 cycles. After the first-stage PCR, these reactions were diluted 100-fold into a nested second-stage PCR reaction and amplified in a Roche LC480 real time PCR instrument.

Figure 19:
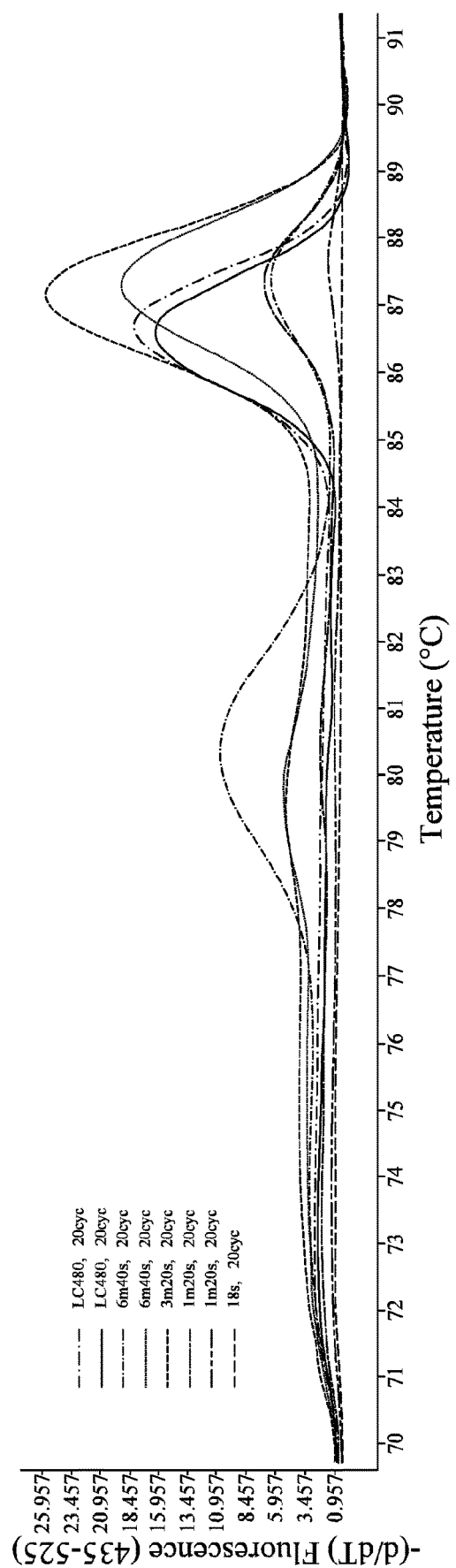
FIG. 19 shows results of amplification using a prototype of the instrument of FIGS. 6-8 in comparison to amplification using a standard plate-based thermocycler.
Figure 20:
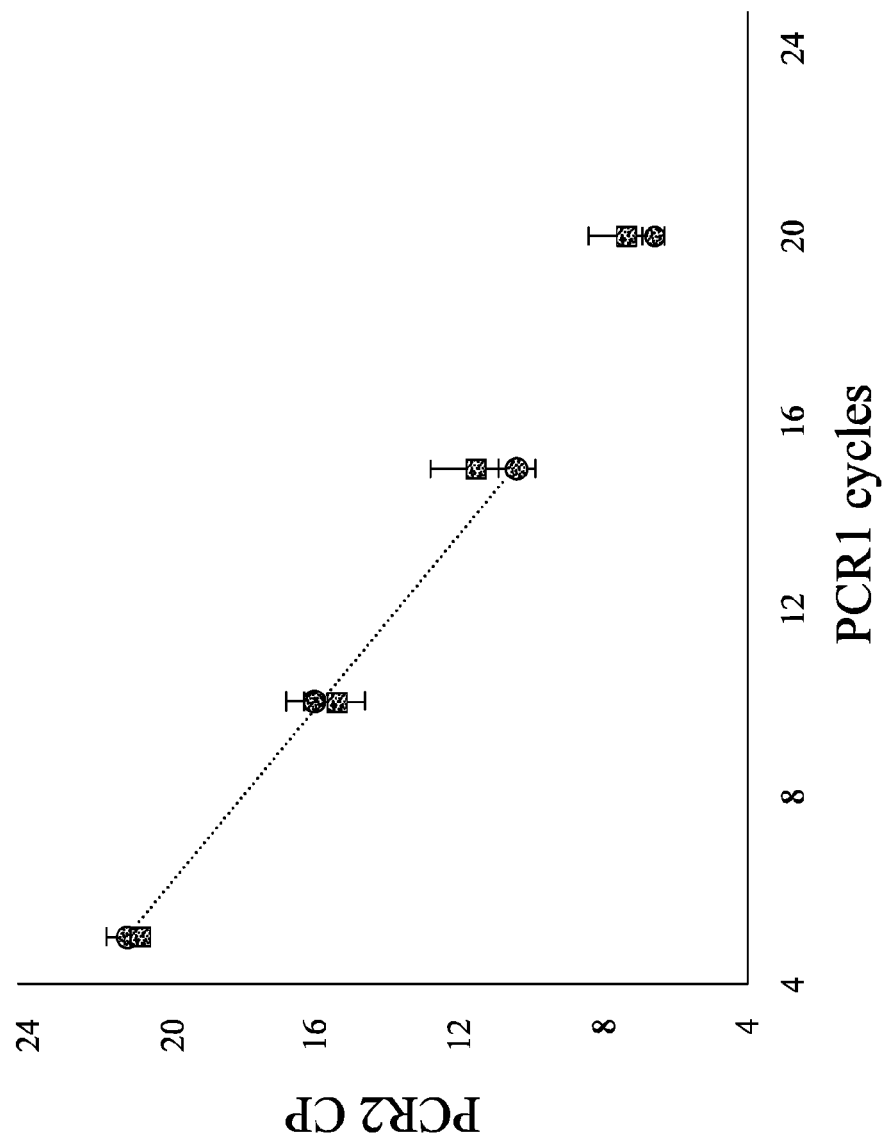
FIG. 20 shows a graph of the second-stage PCR Cp that results from running different numbers of cycles for first-stage PCR in a block thermocycler (circle) and the prototype wiper blade setup (square).

FIGS. 19-20 show results of the PCR in the prototype instrument of FIGS. 6-8. In FIG. 19, melting curves for the first stage reactions in the wiper system at different speeds are compared to melting curves for amplification in the LC480. FIG. 20 shows the results of the cycle course. Amplification in the prototype of FIGS. 6-8 and in the LC480 block thermocycler overlap and are fit by lines with $R^2$ values>0.99). In FIG. 20, the slopes of these lines show the relative efficiency of one cycle in the LC480 compared to one cycle in the prototype. The efficiency of the block cycler (slope of 1.08) is slightly greater than that of the wiper blade system (0.93) indicating slightly less than the full efficiency of a block thermocycler, in approximately 3 min, 20 sec.

Example 3: Three Temperature PCR Using Two Temperature Zones

As discussed above, some PCR protocols use three temperatures, a first temperature for annealing, a somewhat higher temperature for extension that is illustratively chosen based on enzyme activity, and a third highest temperature for denaturation. While FIG. 18 shows an embodiment that uses three heaters 930, 931, 932, in some embodiments it may be desirable to thermocycle larger volumes quickly. Illustratively, it may be desirable to thermocycle first-stage PCR through three temperatures, wherein a heater such as heater assembly 988 may not be able to heat and cool the contents of blister 564 as rapidly as desired.

In one such embodiment, it may be desirable to use a three-step PCR protocol in first-stage PCR in the pouch 510 of FIG. 1. As discussed above, first-stage heater 886 of FIG. 2 is positioned to heat and cool the contents of blister 564 for first-stage PCR. In one embodiment, heater 887 may be provided to control the temperature of the contents of blister 548, where heaters 886 and 887 are controlled together and cycle together. In another embodiment, heaters 886 and 887 may be under separate control, illustratively heater 887 may be provided to maintain a suitable annealing temperature, while blister 886 may be provided to maintain a suitable denaturation temperature, although it is understood that this is illustrative only and that the heaters may be reversed. Other configurations are possible. Two temperature PCR using two heating zones is discussed more fully in U.S. Patent Application No. 2014-0038272, herein incorporated by reference in its entirety.

In one embodiment, Peltier heaters or heaters such as those disclosed in U.S. patent application Ser. No. 15/099, 721, herein incorporated by reference, may be used for heaters 887, 888 and other heaters discussed herein, although other heaters or heater assemblies as are known in the art may be used to obtain three-temperature cycling in two temperature zones, provided that the temperature of these heaters is adjustable. In one embodiment, active control of these heaters is desirable.

Figure 21:
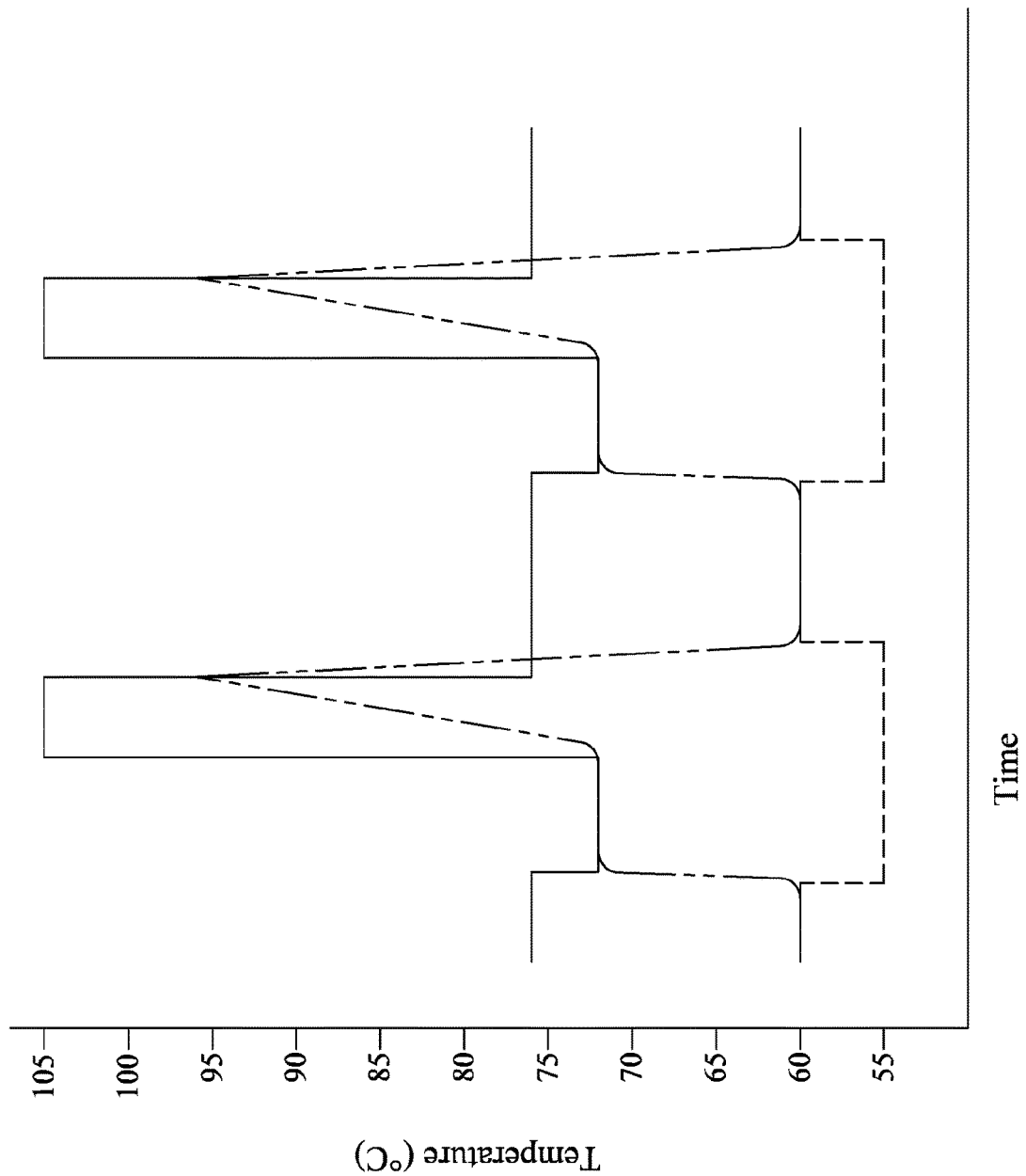
FIG. 21 shows a heating profile for a three-temperature PCR protocol using two heaters. The extension/denaturation heater temperature is shown as a solid line, the annealing heater temperature is shown as a dashed line, and the sample temperature is shown as a dotted line.

One example is illustrated in FIG. 21, wherein the dotted line illustrates the temperature of the sample. In this example, where heater 887 may be used for the annealing temperature, the temperature of heater 887 may be set at the desired annealing temperature, illustratively 60° C., although it is understood that this temperature is illustrative only and that other annealing temperatures may be used, depending on the length and GC content of the primers. When the sample is moved into blister 548, the sample may be held in blister 548 until the entire sample reaches the annealing temperature. In some illustrative protocols, it may be desirable to hold the sample in blister 548 for a period of time after the sample reaches the annealing temperature. In another illustrative embodiment, as illustrated in FIG. 21 by the dashed line, heater 887 may be held at a temperature a few degrees below the annealing temperature, illustratively 2 to 20 degrees below the annealing temperature (the "low annealing temperature"), illustratively 55° C., although other temperatures may be suitable. When the sample is moved from blister 564, which is under control of heater 886 and is substantially hotter than the annealing temperature, the sample may be cooled down to the annealing temperature more quickly because heater 887 is below the annealing temperature. Optionally, movement of bladder 848 may mix the fluid sample in blister 548 to obtain a more uniform temperature within blister 548. Once the sample fluid has been in blister 548 for a length of time that substantially all of the fluid is at or near the annealing temperature, heater 887 may be adjusted to the annealing temperature, as shown by the dashed lines ( - - - ) in FIG. 21. A hold, illustratively for 2 sec to 5 sec may allow for proper annealing, although a hold may be unnecessary, depending on the chemistry used. The sample may then be moved to blister 564. Once the sample has exited blister 548, as shown in FIG. 21, the temperature of heater 887 may then be adjusted back to the low annealing temperature to be ready for the next cycle. It is understood that many heaters take more time to cool than to heat, and it may be faster to cool heater 887 when blister 546 is empty and there is minimal thermal load on heater 887.

In one example, a suitable extension temperature is chosen, illustratively 72° C., although other extension temperatures may be suitable, depending on amplicon length, GC content, and choice of polymerase. As shown by the solid line (-) in FIG. 21, while the sample is still in blister 548, heater 886 may be adjusted to a temperature that is a few degrees above the extension temperature, illustratively 2 to 10 degrees above the extension temperature (the "high extension temperature"). Once the sample fluid has been in blister 564 for a length of time that substantially all of the fluid is at or near the extension temperature, heater 887 may be adjusted from the high extension temperature to the extension temperature, as shown by the solid line in FIG. 21. As discussed above with respect to blister 548, optional movement of bladder 864 may mix the fluid sample in blister 564 to obtain a more uniform temperature within blister 564. A hold, illustratively for 0 sec to 5 sec may allow for proper extension, depending on the protocol. After this hold, heater 886 may then be adjusted to or a few degrees above the denaturation temperature to denature the nucleic acids. It is understood that if heater 886 is adjusted to a temperature above the denaturation temperature, the fluid sample may reach denaturation more quickly. Again, optional movement of bladder 864 may mix the fluid sample in blister 564 to obtain a more uniform temperature within blister 564. Once the sample has been denatured, optionally with or without a hold at the denaturation temperature, the sample may be moved back to blister 548, the temperature of heater 886 may be adjusted to the high extension temperature, which may be more efficient to obtain without the sample in blister 564, and the cycle repeated a sufficient number of times for amplification. If this is first-stage PCR, it is understood that a reduced number of cycles may be desirable, the number of cycles sufficient for enrichment of the targets, whereas if this is second-stage or single-stage, one may desire to thermocycle to or past plateau phase.

Three temperature cycling may be performed using standard PCR chemistry at a standard PCR cycling protocol, illustratively 20 seconds per cycle or longer. If desired, extreme PCR chemistry using enhanced concentrations of polymerase or primer may be added, and faster thermocycling protocols may be used, as disclosed in U.S. Patent Publication No. 2015-0118715, herein incorporated by reference. It is understood that enhanced concentrations of polymerase or primer may result in formation of increased primer-dimer and other non-specific amplification products, unless cycle time is reduced, and that the greater the concentration of polymerase or primer used, the faster the cycle times, where the polymerase and primer may be increased with roughly proportional reductions in cycle time. Cycle times of ten seconds or less should be possible.

Example 4: Fast Multiplex PCR

A prototype instrument using the pouch and heater configuration similar to that of FIGS. 6-8 was used for multiplexed amplification of DNA in a sample. The templates were a mix of natural and synthetic templates—the templates were a synthetic amplicon with a length of 105 bp (referred to internally as 'mephisto'), a synthetic amplicon with a length of 164 bp (referred to internally as 'Baal3'), a S. cerevisiae sequence (natural, amplicon length 364 bp, referred to internally as 'beer'), M13 (natural, amplicon length 264 bp), and MS2 (natural, amplicon length 309 bp). 150 µl and 75 µl samples were prepared comprising 1000 copies of each template, forward and reverse primers unique to each template (5 µM each primer), DNA polymerase (2 U/µL), dNTPs at 0.45 mM, and 5 mM Mg++. 1× LCGreen was used for detection. It is understood that the reaction mixture is illustrative only and that other mixes may be used. These mixtures were sealed into a blister (e.g., blister 549) in 150 µl and 75 µl aliquots. For the 150 µl reactions, the first heater (e.g., heater 986) was set to 103° C. and the second heater (e.g., heater 987) was set to 55° C. For the 75 µl reactions, the first heater (e.g., heater 986) was set to 102° C. and the second heater (e.g., heater 987) was set to 55° C. These reactions were thermocycled according to the procedure described in, for example, FIGS. 6-8 with the wiper blade(s) 949 in contact with the blister and with the wiper head 989 rotating at a speed of one full rotation every 8 sec (e.g., cycles of rotation of 180°, hold for 4 seconds, rotate 180°, hold for 4 seconds, etc., or rotate 90°, hold for 2 seconds, rotate 90°, hold for 2 seconds, etc., wherein the rotation time was negligible). It is understood that the rotational speed corresponds to cycle time, with each full revolution representing one cycle. Also, while holds after each quarter turn are used in this example, such is illustrative only and continuous rotation is contemplated. After the first-stage PCR, these reactions were diluted 100-fold into a nested second-stage PCR reaction and amplified in a Roche LC480 real time PCR instrument.

Figure 22:
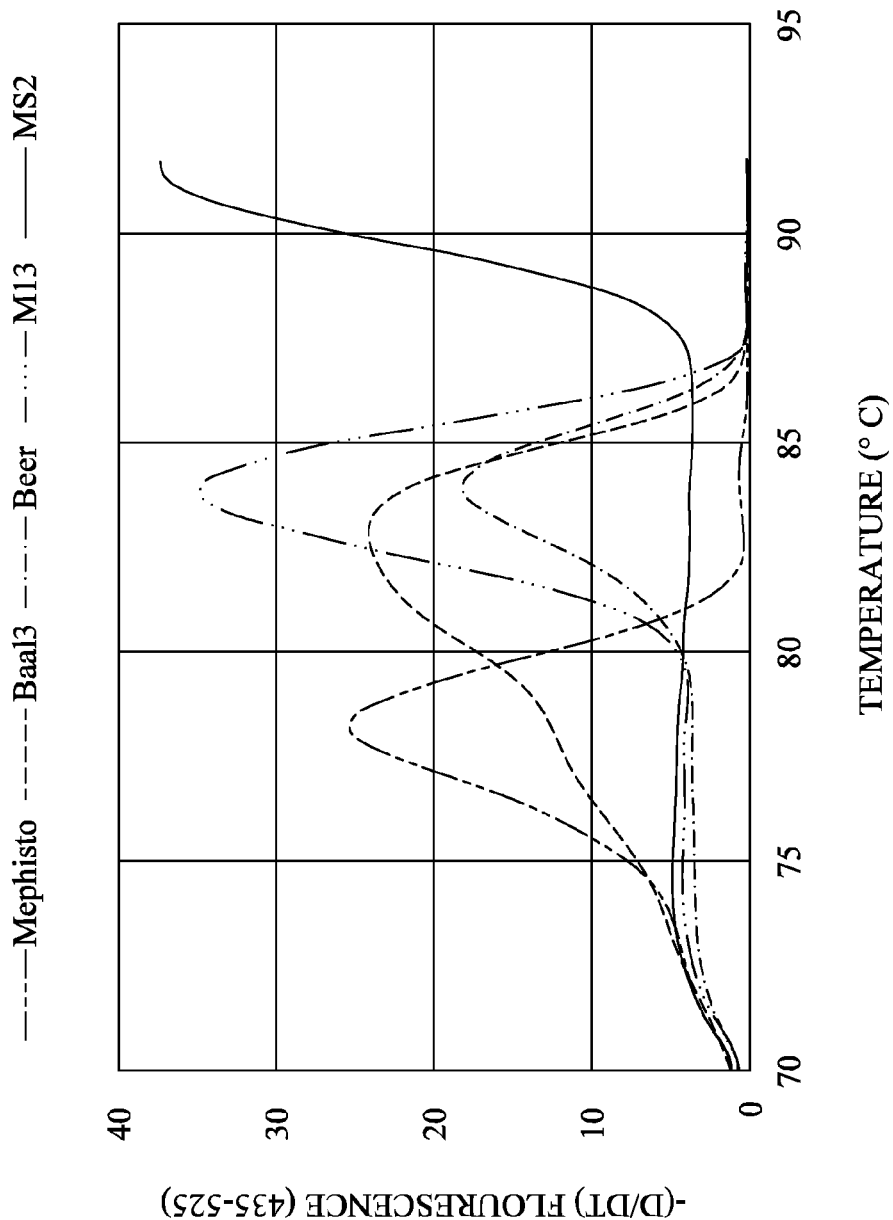
FIG. 22 shows DNA melting curves for multiplexed amplification using a prototype instrument similar to the instrument of FIGS. 6-8 or FIGS. 12A-13B for first-stage amplification. Following first-stage amplification, the amplification product was diluted and amplified for second-stage PCR and melting in a Roche LC480 real time PCR instrument.

FIG. 22 shows results of a melting experiment in second-stage PCR showing that all of the first-stage PCR reactions were successful. All of the templates were amplified in first-stage PCR and second-stage PCR and all of the products melted at their expected temperature. This demonstrates that the prototype system can be used for multiplex first-stage PCR.

Example 5: Fast PCR

In this Example, a synthetic DNA template (mephisto) was amplified for first-stage PCR in an LC480 instrument according to standard PCR protocols. The amplification product from the first-stage reaction was diluted 1:100 with a second-stage amplification mixture (e.g., unique forward and reverse primers (5 µM each primer), DNA polymerase (2 U/µL), dNTPs at 0.45 mM, 5 mM Mg++, and 1× LCGreen dye for detection) and injected into a 5-well array similar to array 1430 of FIG. 14A or array 1500 of FIG. 15A. The volume of each well of the array is approximately 0.5 µL. The samples were thermocycled for second-stage PCR in a prototype instrument similar to the instruments shown in FIGS. 12A-13B. The array was thermocycled with a two element heater similar to heater assemblies 1270 and 1335 with a first heater set at 96° C. and a second heater set at 60° C. Second-stage PCR was carried out on the array according to the procedure discussed in reference to FIGS. 16A-16F, and specifically with reference to FIGS. 16E and 16F. The array with the second-stage PCR sample was thermocycled for 40 cycles at 8 sec./cycle (4 sec. at 96° C., 4 sec. at 60° C., etc.).

Figure 23:
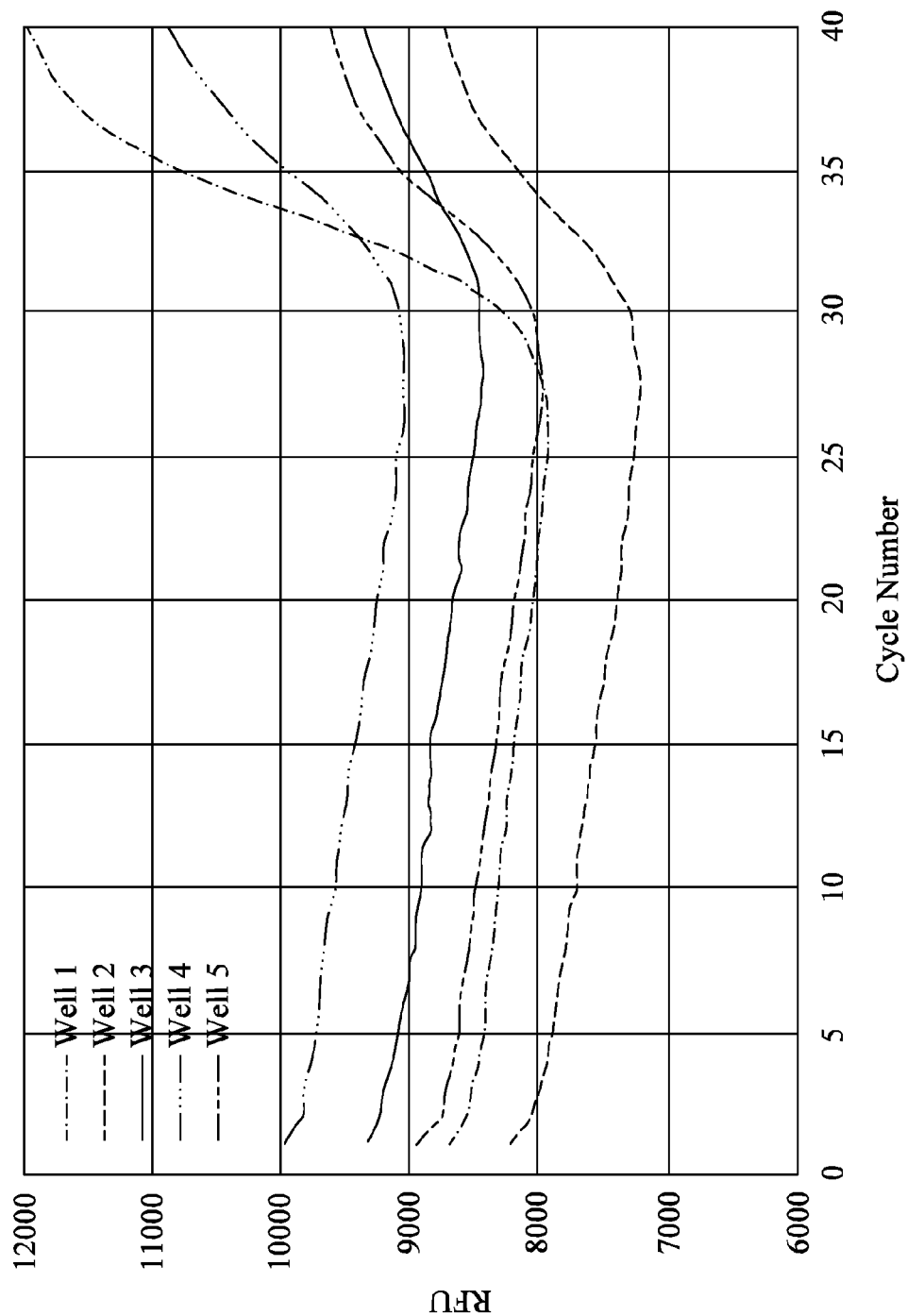
FIG. 23 shows real-time DNA amplification data for a second-stage single-plex DNA amplification reaction. A Roche LC480 real time PCR instrument was used for first-stage PCR; the amplification product from first-stage PCR was diluted, mixed with a second-stage PCR master mix, and injected into an array similar to array 1430 of FIG. 14A for second-stage amplification. Thermocycling for amplification was performed using a procedure similar to the second-stage PCR procedure described in reference to FIGS. 16E and 16F.
Figure 24:
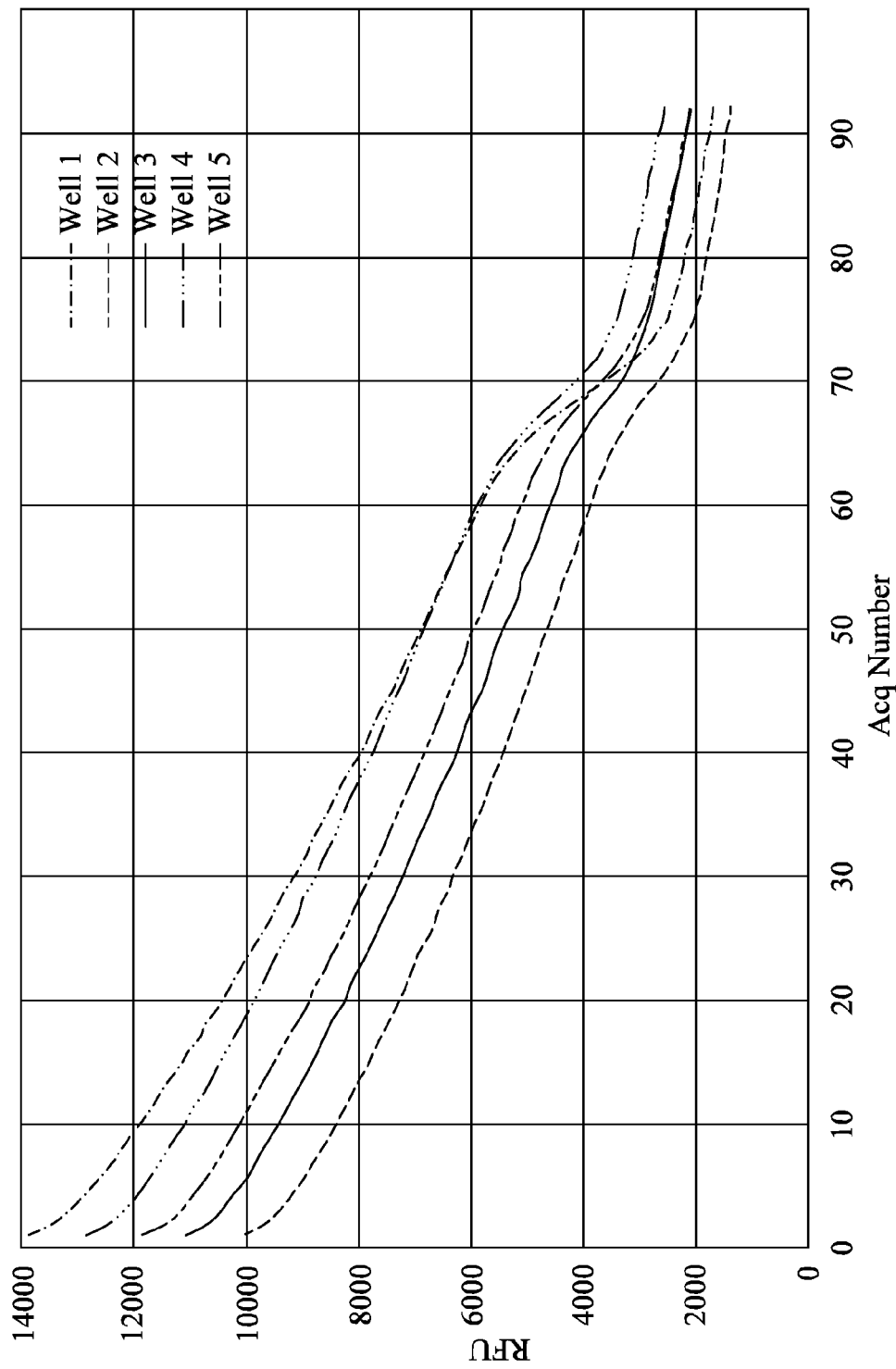
FIG. 24 shows DNA melting curves for second-stage amplification of FIG. 23.

FIGS. 23 and 24 illustrate the results of the second-stage PCR reaction. FIG. 23 shows the change in fluorescence in each of the wells of the array as a function of cycle number and FIG. 24 shows a melting curve for DNA product (if present) in each of the wells of the array. FIGS. 23 and 24 show that the reaction was most successful for well 1 of the array (FIG. 23) and that the product had a melting transition at the expected temperature for the mephisto product (FIG. 24). This Example illustrates that second-stage PCR can be successfully carried out by a two temperature heater unit with the heater transitioning the array from temperature to temperature by moving the heater assembly relative to the array. One will appreciate that thermocycling may also be accomplished by moving the array relative to the heater elements by, for example, laterally translating the sample container or the receptacle that positions the sample container in the instrument.

Example 6: Fast First-Stage and Second-Stage PCR

In this Example, a synthetic DNA template (mephisto) was amplified for first-stage PCR and second-stage PCR in a reaction container similar to pouch 1400 illustrated in FIG. 14A. For first-stage PCR, ~75,000 copies of the template DNA, forward and reverse primers unique to the template (5 µM each primer), DNA polymerase (2 U/µL), and dNTPs at 0.45 mM, and 5 mM Mg++ were combined and 75 µL were injected into and sealed in a blister (e.g., blister 1410) for the first stage PCR reaction. The reaction container was placed in an instrument similar to instrument 1300 for PCR amplification.

For first-stage PCR, the first heater (e.g., heater 1387) was set to 58° C. and the second heater (e.g., heater 1386) was set to 106° C. The heater assembly (e.g., heater assembly 1335) was positioned so that the temperature of approximately one half the reaction blister could be controlled by the first heater and the temperature of the remainder could be controlled by the second heater. The contents of the reaction blister were thermocycled in the instrument according to the procedure described in, for example, FIGS. 6-8 with the wiper blade(s) (e.g., wiper blades 1149) in contact with the blister and with the wiper head (e.g., wiper head 1100) rotating with a cycle time of 8 sec (e.g., cycles of rotation of 90°, hold for 2 seconds, rotate 90°, hold for 2 seconds, etc.). It is understood that the rotational speed corresponds to cycle time, with one full rotation being equivalent to one cycle.

Following 20 cycles of first-stage PCR in the first-stage PCR reaction blister (e.g., blister 1410), a portion of the first-stage PCR reaction (e.g., ~1 µL) was moved to a volume measuring well (e.g., volumetric well 1415) and mixed with second-stage PCR reagents (DNA polymerase (2 U/µL), dNTPs at 0.45 mM, 2 mM Mg++, and 1× LC Green for detection) by mixing between two larger volume blisters of the pouch (e.g., blisters 1420 and 1425). It is understood that the level of dilution may be adjusted by altering the volume of the volume measuring well or by altering the volume of the diluting reagents (illustratively a polymerase, dNTPs, and a suitable buffer; although other components may be suitable, particularly for non-PCR amplification methods) added to the sample from first-stage PCR. If desired, this mixture of the sample and second-stage PCR master mix may be pre-heated in the volumetric well 1415 and blisters 1420 and 1425 prior to movement to second-stage array for second-stage amplification. Such preheating and separation of the primers from the master mix may obviate the need for a hot-start component (antibody, chemical, or otherwise) in the second-stage PCR mixture.

Following preparation of the sample for second-stage PCR in, for example, volumetric well 1415 and blisters 1420 and 1425, the sample may be moved to an array similar to array 1430 for second stage PCR. Each of the wells of the array is pre-loaded with specific forward and reverse PCR primers. Primers were spotted in the wells of the array at either 2.5 µM or 5 µM. The wells of the array are filled by flooding the array with the second-stage PCR master mix. The wells of the array may be heat sealed and/or sealed by inflating a clear, flexible bladder over the array to seal off access to the fill channels. Excess second-stage PCR master mix may also be purged from the array by inflating the clear, flexible bladder over the array. In this case, the clear, flexible bladder was inflated to a pressure of approximately 20 psi. As depicted in FIGS. 16E and 16F, thermocycling for second-stage PCR may be accomplished by translating heater assembly 1335 back and forth under the array so that the array and the contents of the individual wells are under temperature control of the second heater (e.g., heater 1386 for denaturation), then the first heater (e.g., heater 1387 for annealing and elongation), then the second heater (for denaturation again), etc. In this Example, the second heater was set to 102° C. with a hold at the second heater of 2 sec. and the first heater was set at 65° C. with a hold of 6 sec. The second-stage reaction was thermocycled for a total of 30 cycles. Nucleic acid amplification and DNA melting in the array were monitored with a camera similar to camera 1325 depicted in FIGS. 13A and 13B.

Figure 25:
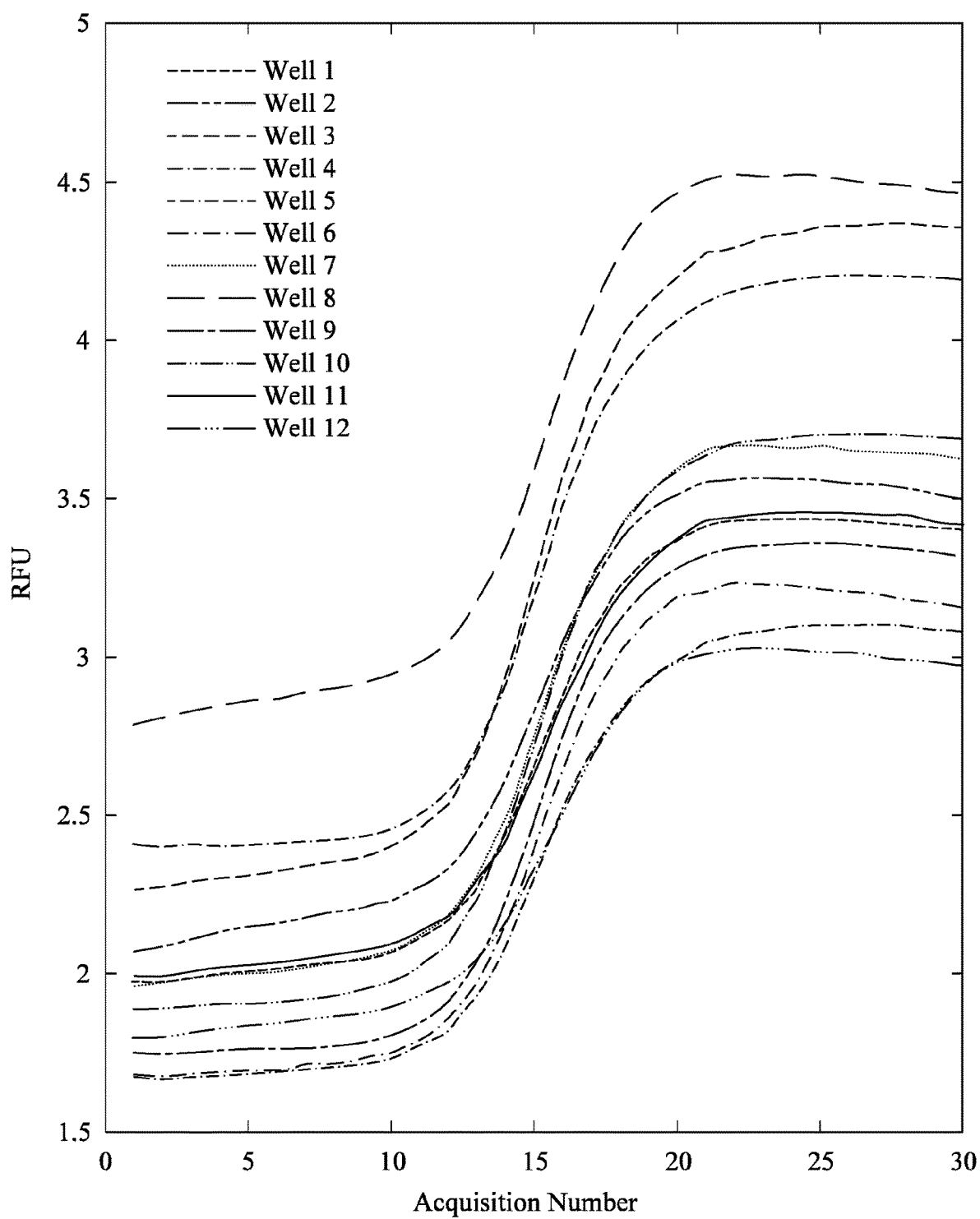
FIGS. 25-27 depict the results of first-stage and second-stage amplification using an instrument similar to the instrument depicted in FIGS. 13A and 13B.
Figure 26:
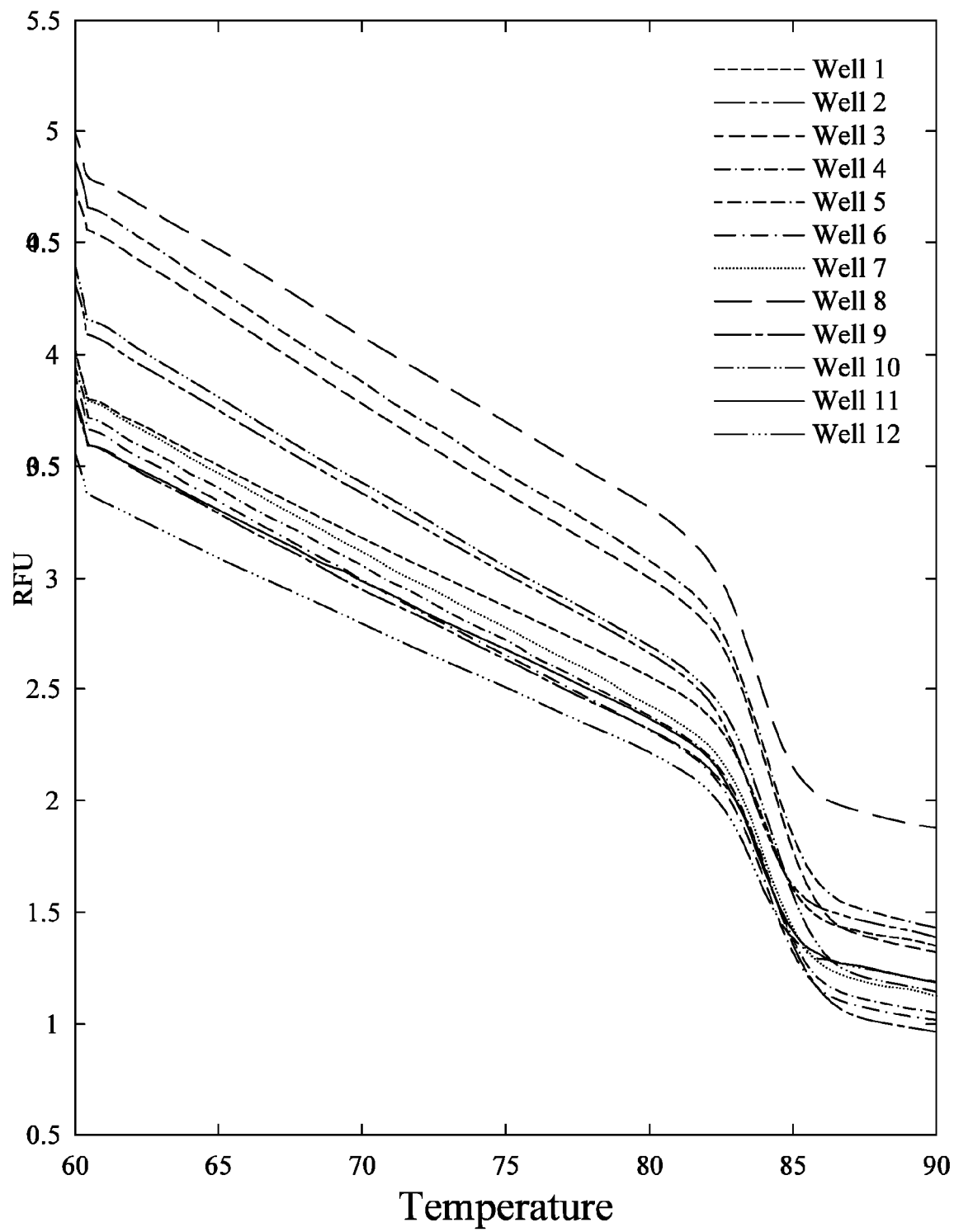
Figure 27:
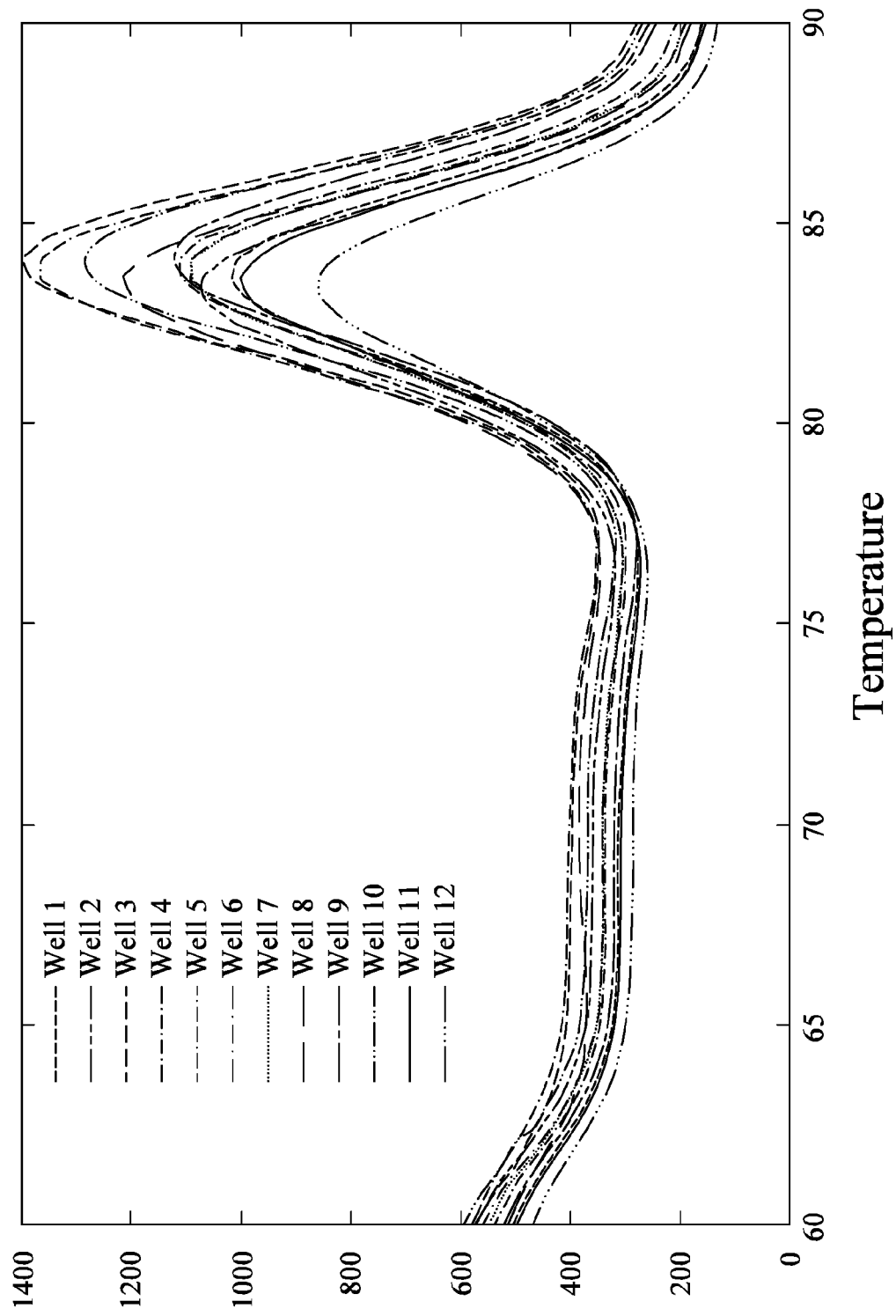

FIGS. 25-27 depict the results of the second-stage PCR reaction. FIG. 25 depicts the increase in fluorescence in the wells of the array as a function of cycle number. As can be seen, DNA amplification occurred in all wells of the array. Likewise, a similar time course (e.g., crossing point) for amplification was observed in each of the wells. FIGS. 26 and 27 depict the results of a melting experiment to ensure that the product being amplified is the correct product. FIG. 26 is a raw melting curve and FIG. 27 depicts a negative first derivative (dF/dt) of the melting curve. As can be seen in FIGS. 26 and 27, the product in all of the wells has a melting transition at essentially the same temperature. The melting transition for all of the well occurs at approximately 84° C., which is the anticipated melting temperature for this particular synthetic amplicon.

Example 7: Temperature Calibration and Thermocycling Speed in the Second-Stage PCR Array Referring now to FIGS. 28-31, results are illustrated of a series of experiments designed to test the temperature response of the fluid in the well(s) of an array similar to array 1430 or array 1500. In the experiments, a small thermocouple was inserted into one or more wells of the array and sealed between the film layers. For thermocycling, the array was filled with aqueous PCR buffer, inserted into an instrument similar to instrument 1200 or 1300, and subjected to thermocycling according to the protocol described with respect to FIGS. 16E and 16F. For these experiments, a clear, flexible bladder in the instrument was inflated over the array to approximately 20 PSI. These experiments show the temperature response of the fluid in the array with different dwell times at the high and low temperature heaters; regardless of the dwell time in the illustrated examples, the transition time of the heaters (e.g., high temp to low temp or low tem to high temp) is rapid relative to the dwell time. These data and other data not shown are being used to develop a temperature model that includes the set points of the heaters, the dwell time at each temperature, and the thermal response of the array and the fluid therein so that users can reliably set high and low target temperatures for the fluid in the array for thermal cycling and amplification of various templates with various primer sets.

Figure 28:
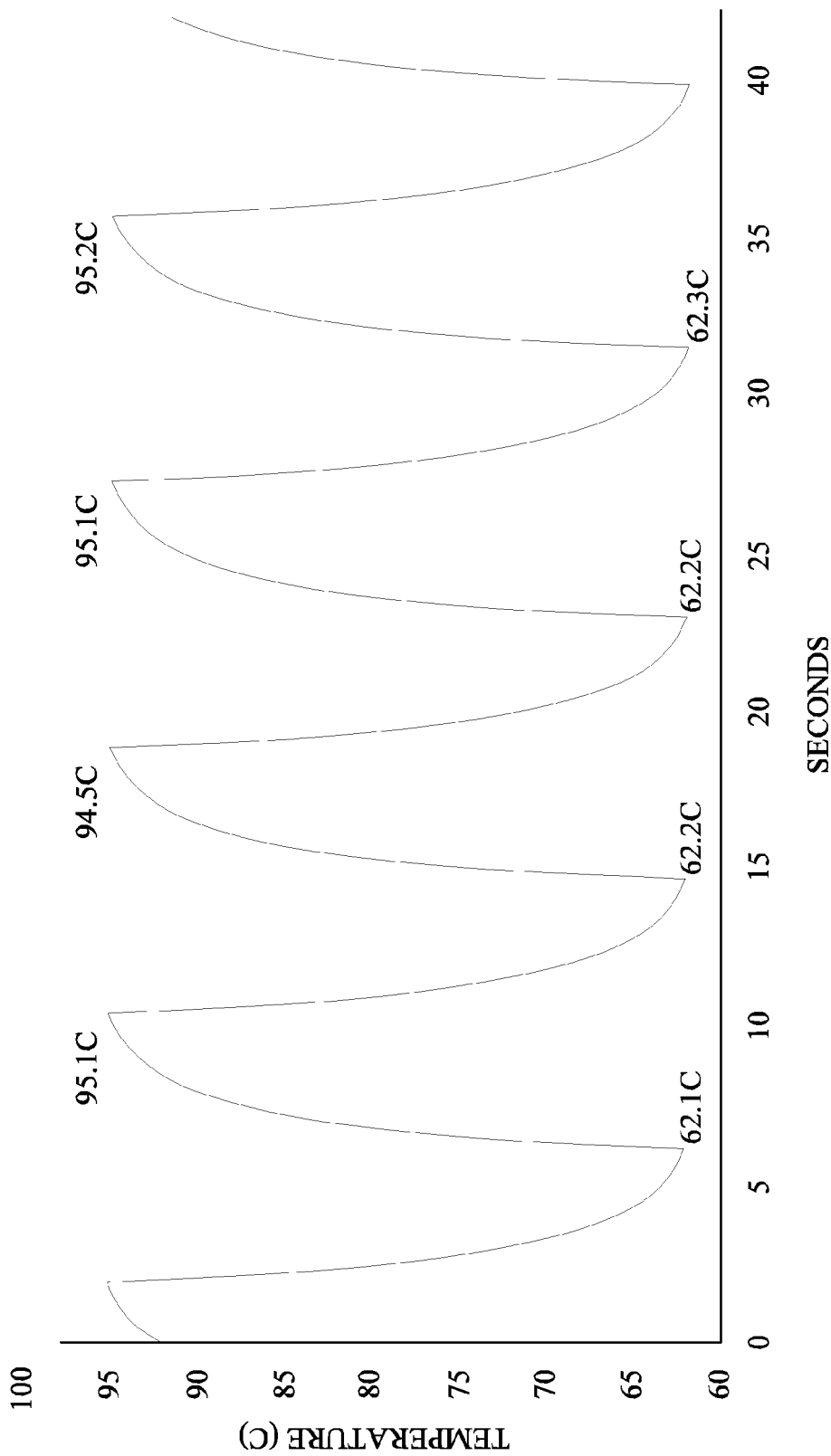
FIGS. 28-31 illustrate the results of a series of experiments designed to test the temperature response of fluid in the well(s) of an array similar to array 1430 or array 1500 with a thermocycling procedure similar to the procedure illustrated in FIGS. 16E and 16F.

In the experiment illustrated in FIG. 28, the target end point temperatures were 95° C. and 62° C. The heaters were set at 98° C. and 62° C. with 4 second hold times (i.e., dwell times) at each temperature zone. The target end point temperatures were 95° C. and 62° C. Because this experiment includes a relatively long hold time, the set points for the heaters and the target temperatures are relatively close together. As can be seen in FIG. 28, the fluid in the well(s) (~0.5 µL) could be thermocycled between ~95° C. and ~62° C. with these heater set points, hold times, and the translating heater protocol described elsewhere herein.

Figure 29:
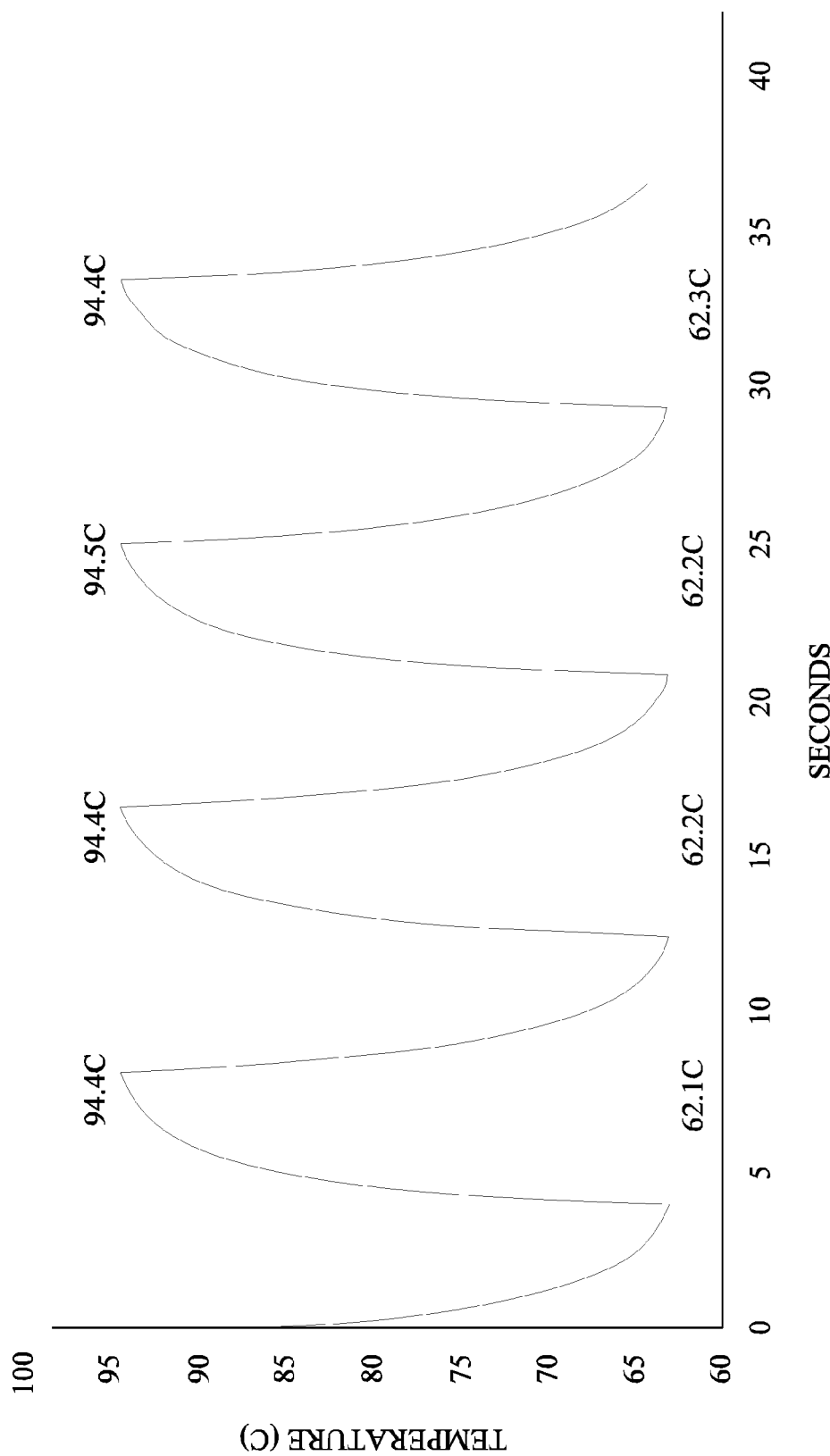

In the experiment illustrated in FIG. 29, the heaters were set at 97° C. and 62° C. with 4 second hold times at each temperature zone. The target end point temperatures being aimed for in this experiment were 94° C. and 62° C. As can be seen in FIG. 29, the fluid in the well(s) (~0.5 µL) could be thermocycled between ~94° C. and ~63° C. with these heater set points, hold times, and the translating heater protocol.

Figure 30:
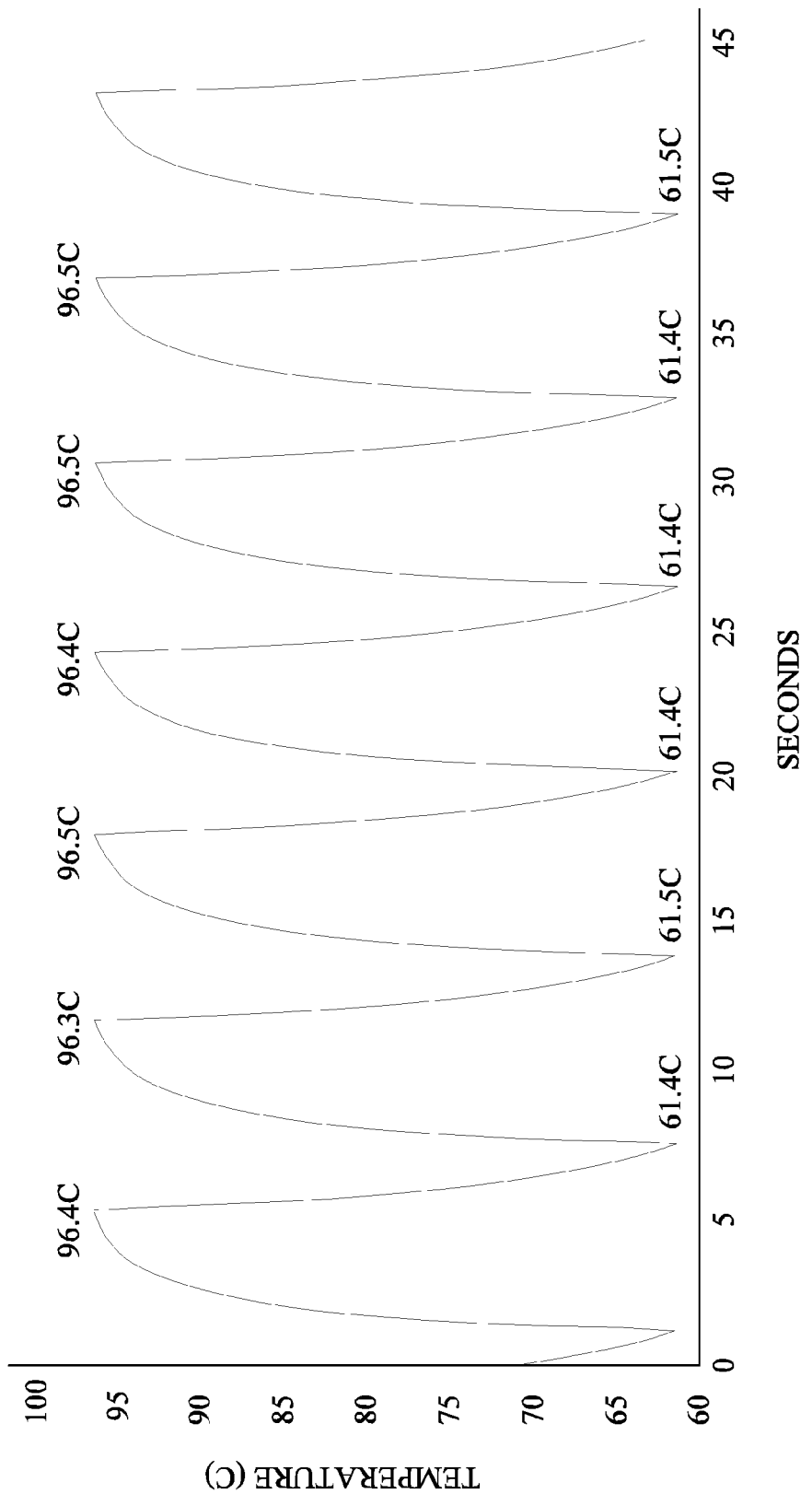

In the experiment illustrated in FIG. 30, the heaters were set at 99° C. and 56° C. with 2 second hold times at each temperature zone. The target end point temperatures were 96° C. and 61° C. As can be seen in FIG. 30, the fluid in the well(s) (~0.5 µL) could be thermocycled ~96° C. and ~61° C. with these heater set points, hold times, and the translating heater protocol.

Figure 31:
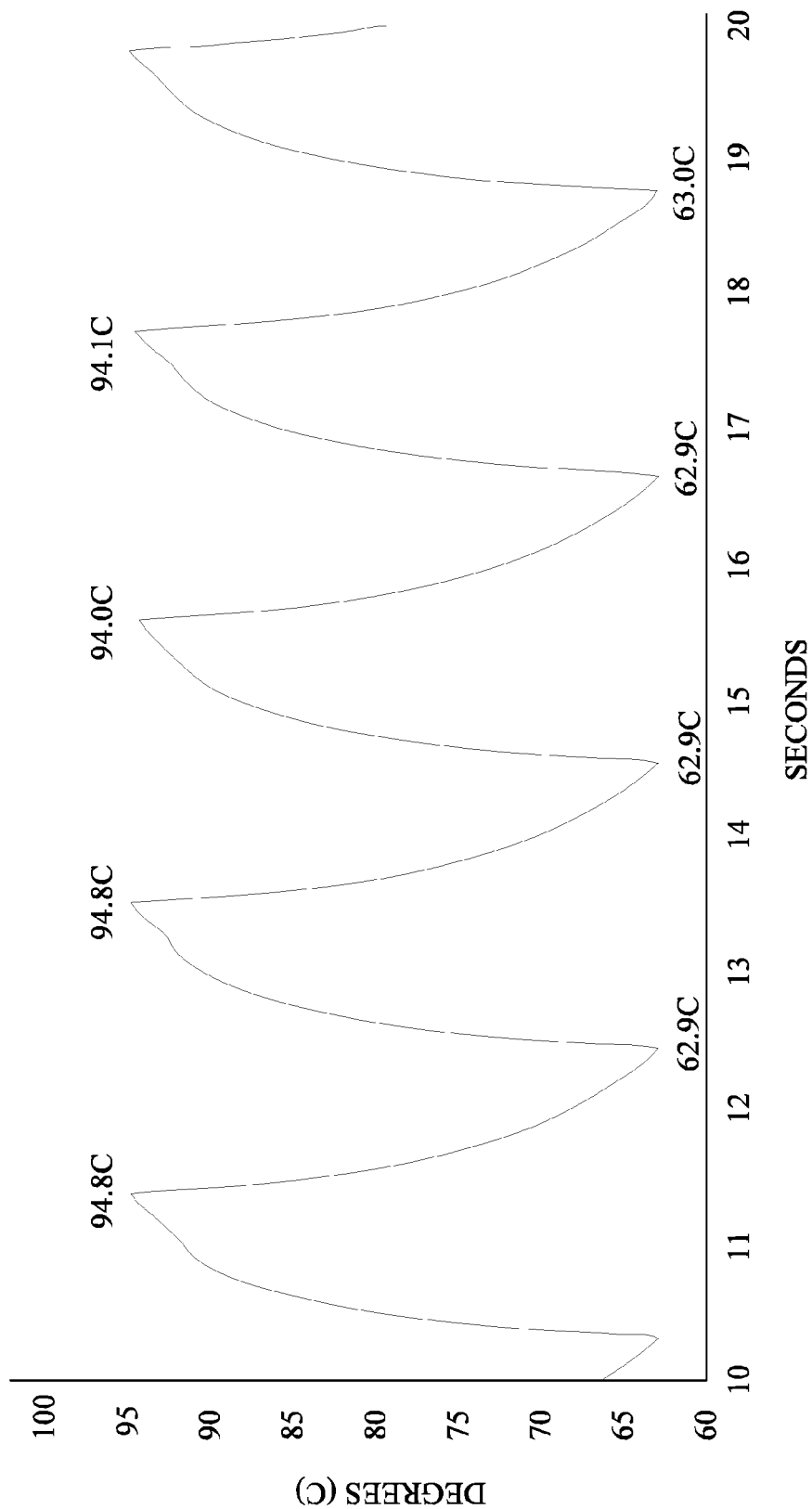

In the experiment illustrated in FIG. 31, the heaters were set at 108° C. and 52° C. with 1 second hold times at each temperature zone. The target end point temperatures were 95° C. and 63° C. As can be seen in FIG. 31, the fluid in the well(s) (~0.5 µL) could be thermocycled between ~95° C. and ~63° C. with these heater set points and the translating heater protocol even with hold times as low as 1 second. As described in, for example U.S. Pat. Pub. No. 2015/0118715 and U.S. Pat. Pub. No. 2016/0289736, which were incorporated herein above in their entireties, adjustments in chemistry, wherein polymerase and primer concentration are increased, can permit the polymerase chain reaction to proceed at rates compatible with 8 second, 4 second, 2 second, or shorter cycle times.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

What is claimed is:

1. A method for performing PCR, comprising:
   (a) providing a PCR mixture in a sample vessel, the sample vessel having a volume and the PCR mixture having a volume;
   (b) thermocycling the volume of the PCR mixture in the volume of the sample vessel for a first number of cycles, each of the first number of cycles having a first cycle time;
   (c) reducing the volume of the sample vessel to a second volume of the sample vessel thereby reducing the volume of the PCR mixture to a second volume of the PCR mixture, the second volume of the sample vessel being smaller than the volume of the sample vessel and the second volume of the PCR mixture being smaller than the volume of the PCR mixture,
   wherein the sample vessel is compressible, and the reducing step is performed by compressing the sample vessel to the second volume of the sample vessel to expel a portion of the sample from the sample vessel; and
   (d) thermocycling the second volume of the PCR mixture for a second number of cycles in the second volume of the sample vessel, each of the second number of cycles having a second cycle time, the second cycle time being shorter than the first cycle time.

2. The method of claim 1, further comprising:
   (e) reducing the second volume of the PCR mixture in the sample vessel to a third volume, the third volume of the PCR mixture being smaller than the second volume of the PCR mixture; and
   (f) thermocycling the third volume of the PCR mixture for a third number of cycles in the sample vessel, each of the third number of cycles having a third cycle time, the third cycle time being shorter than the second cycle time.

3. The method of claim 1, wherein the sample vessel is in contact with a first temperature zone and a second temperature zone, and one or more of the thermocycling steps includes moving the sample between the first and second temperature zones.

4. The method of claim 3, further comprising moving a first portion of the PCR mixture to a second portion of the sample vessel while moving a second portion of the PCR mixture to a first portion of the sample vessel such that the first and second portions of the PCR mixture are under control of the first and second temperature zones simultaneously, wherein the first temperature zone is hotter than the second temperature zone.

5. The method of claim 1, wherein the sample vessel is configured to contact a first temperature zone and a second temperature zone, and the thermocycling step includes alternatingly contacting the sample vessel with the first temperature zone and then the second temperature zone.

6. The method of claim 1, wherein the sample vessel is heated by a heater that thermocycles between two or more temperatures, the heater cycling at the first cycle time in step (b) and at the second cycle time at step (d).

7. The method of 1, wherein the first number of cycles is 2 to 10 cycles.

8. The method of claim 1, wherein the second volume of the PCR mixture in the second volume of the sample vessel is 5%, 10%, 15%, 20%, 25%, 30%, 35%, 40%, 45% or 50% smaller than the volume of the PCR mixture in the volume of the sample vessel.

9. The method of claim 1, wherein (i) the second volume of the PCR mixture in the second volume of the sample vessel is 50% smaller than the volume of the PCR mixture in the volume of the sample vessel and (ii) the second cycle time is 25% to 50% shorter than the first cycle time.

10. The method of claim 1, wherein the reducing step comprises reducing the volume of the PCR mixture in the sample vessel 2 to 5 times and reducing the cycle time after each volume reduction.

11. The method of claim 1, wherein the sample vessel is part of a closed sample container having at least one additional fluidly connected sample vessel therein.

12. A method for performing PCR, comprising:
   (a) providing a PCR mixture in a compressible sample vessel, the sample vessel having a volume and the PCR mixture having a volume;
   (b) thermocycling the volume of the PCR mixture in the volume of the sample vessel for a first number of cycles, each of the first number of cycles having a first cycle time;
   (c) compressing the sample vessel, thereby reducing the volume of the sample vessel to a second volume of the sample vessel and expelling a portion of the sample from the sample vessel, thereby reducing the volume of the PCR mixture to a second volume of the PCR mixture, the second volume of the sample vessel being smaller than the volume of the sample vessel and the second volume of the PCR mixture being smaller than the volume of the PCR mixture; and
   (d) thermocycling the second volume of the PCR mixture for a second number of cycles in the second volume of the sample vessel, each of the second number of cycles having a second cycle time, the second cycle time being shorter than the first cycle time.

* * * * *